United States Patent
Kilburn et al.

(10) Patent No.: US 11,466,027 B2
(45) Date of Patent: Oct. 11, 2022

(54) MODULATORS OF THE NMDA RECEPTOR

(71) Applicant: H. Lundbeck A/S, Valby (DK)

(72) Inventors: John Paul Kilburn, Valby (DK); Erhad Ascic, Valby (DK); Mauro Marigo, Valby (DK); Laurent David, Valby (DK)

(73) Assignee: H. Lundbeck A/S, Valby (DK)

( * ) Notice: Subject to any disclaimer, the term of this patent is extended or adjusted under 35 U.S.C. 154(b) by 214 days.

(21) Appl. No.: 16/916,769

(22) Filed: Jun. 30, 2020

(65) Prior Publication Data

US 2021/0002292 A1 Jan. 7, 2021

(30) Foreign Application Priority Data

Jul. 3, 2019 (DK) .............................. PA201900821

(51) Int. Cl.
*C07D 495/04* (2006.01)
(52) U.S. Cl.
CPC ................................. *C07D 495/04* (2013.01)
(58) Field of Classification Search
CPC .................................................. C07D 495/04
USPC ......................................................... 514/301
See application file for complete search history.

(56) References Cited

U.S. PATENT DOCUMENTS

| | | | |
|---|---|---|---|
| 5,026,700 | A | 6/1991 | Harrison et al. |
| 7,754,896 | B2 | 7/2010 | Azzaoui et al. |
| 11,358,971 | B2 | 6/2022 | Kilburn et al. |
| 2014/0336108 | A1 | 11/2014 | Guo et al. |
| 2021/0047342 | A1 | 2/2021 | Kilburn et al. |

FOREIGN PATENT DOCUMENTS

| | | |
|---|---|---|
| EP | 0 581 106 A1 | 2/1994 |
| EP | 1 708 998 A1 | 10/2006 |
| WO | WO 95/21612 A2 | 8/1995 |
| WO | WO 96/40097 A1 | 12/1996 |
| WO | WO 97/46511 A1 | 12/1997 |
| WO | WO 98/56752 A1 | 12/1998 |
| WO | WO 2004/048386 A2 | 6/2004 |
| WO | WO 2005/070886 A1 | 8/2005 |
| WO | WO 2006/030031 A1 | 3/2006 |

OTHER PUBLICATIONS

Urwyler et al., Journal of Medicinal Chemistry (2009), 52(16), 5093-5107.*
U.S. Appl. No. 16/916,681, filed Jun. 30, 2020, Pending.
PCT/EP2020/068522, Oct. 2, 2020, International Search Report and Written Opinion.
PCT/EP2020/068513, Oct. 2, 2020, International Search Report and Written Opinion.
PA 201900821, Oct. 9, 2019, Danish Search Report.
PA 201900822, Oct. 9, 2019, Danish Search Report.
International Search Report and Written Opinion dated Oct. 2, 2020 in connection with Application No. PCT/EP2020/068522.
International Search Report and Written Opinion dated Oct. 5, 2020 in connection with Application No. PCT/EP2020/068513.
Danish Search Report dated Oct. 9, 2019 in connection with Application No. PA 201900821.
Danish Search Report dated Oct. 9, 2019 in connection with Application No. PA 201900822.
Heresco-Levy et al., Controlled trial of D-cycloserine adjuvant therapy for treatment-resistant major depressive disorder. J Affect Disord. Jul. 2006;93(1-3):239-43. doi: 10.1016/j.jad.2006.03.004. Epub May 4, 2006.
Olden et al., Pilot Study of a Telehealth-Delivered Medication-Augmented Exposure Therapy Protocol for PTSD. J Nerv Ment Dis. Feb. 2017;205(2):154-160. doi: 10.1097/NMD.0000000000000563.
Peyrovian et al., The glycine site of NMDA receptors: A target for cognitive enhancement in psychiatric disorders. Prog Neuropsychopharmacol Biol Psychiatry. Jun. 8, 2019;92:387-404. doi: 10.1016/j.pnpbp.2019.02.001. Epub Feb. 6, 2019.
Urwyler et al., Drug design, in vitro pharmacology, and structure-activity relationships of 3-acylamino-2-aminopropionic acid derivatives, a novel class of partial agonists at the glycine site on the N-methyl-D-aspartate (NMDA) receptor complex. J Med Chem. Aug. 27, 2009;52(16):5093-107. doi: 10.1021/jm900363q.
Zhou et al., Targeting N-methyl-D-aspartate receptors for treatment of neuropathic pain. Expert Rev Clin Pharmacol. May 2011;4(3):379-88. doi: 10.1586/ecp.11.17.
International Search Report and Written Opinion dated Mar. 2, 2022 in connection with Application No. PCT/EP2021/085681.
Greenfield et al., Synthesis and biological activities of aryl-ether-, biaryl-, and fluorene-aspartic acid and diaminopropionic acid analogs as potent inhibitors of the high-affinity glutamate transporter EAAT-2. Bioorg Med Chem Lett. Nov. 15, 2005;15(22):4985-8.
Maolanon et al., Subtype-specific agonists for NMDA receptor glycine binding sites. ACS Chem Neurosci. Aug. 16, 2017;8(8):1681-1687. Epub May 30, 2017.
Nakada et al., Novel acyl coenzyme A (CoA): diacylglycerol acyltransferase-1 inhibitors: synthesis and biological activities of diacylethylenediamine derivatives. Bioorg Med Chem. Apr. 1, 2010;18(7):2785-95. Epub Feb. 4, 2010.
Slattery et al.,Using the rat forced swim test to assess antidepressant-like activity in rodents. Nat Protoc. May 3, 2012;7(6):1009-14.

* cited by examiner

*Primary Examiner* — Niloofar Rahmani
(74) *Attorney, Agent, or Firm* — Wolf, Greenfield & Sacks, P.C.

(57) ABSTRACT

The present invention is directed to novel modulators of the NMDA receptor. Separate aspects of the inventions are directed to pharmaceutical compositions comprising said compounds and uses of the compounds to treat neurological disorders or neuropsychiatric disorders such as depression.

19 Claims, 2 Drawing Sheets

MODULATORS OF THE NMDA RECEPTOR

CROSS-REFERENCE TO RELATED APPLICATION

This application claims priority to Danish Application No. PA201900821, filed Jul. 3, 2019, the entire contents of the aforementioned application is hereby incorporated herein by reference.

FIELD OF THE INVENTION

The present invention is directed to compounds which are modulators of the NMDA receptor, pharmaceutical compositions comprising the compounds, and their use in treatment of neurological disorders or neuropsychiatric disorders such as depression, in particular major depressive disorder (MDD) and treatment-resistant depression (TRD).

BACKGROUND OF THE INVENTION

The World Health Organization estimates 350 million people will be affected with Major Depressive Disorder (MDD) and has projected that depression will constitute the largest health burden on society worldwide by 2030. A rough working estimate of prevalence is that depression affects ⅕th of the population at some point, affecting women in a higher proportion than men (5-9% and 2-3% incidence respectively in the US, representing an overall incidence of 6.6%). The North-American Center for Disease Control has reported that from 2005-2008, 8.9% of the US population was prescribed an antidepressant during any given month, antidepressants being also prescribed for anxiety, pain, and other non-mood disorders [Murray et al., Global Burden of Disease Study. Lancet. May 17, 1997; 349(9063):1436-1442].

Antidepressants are marketed and thus known to the skilled person. Examples of different types of antidepressant are but not limited to selective serotonin reuptake inhibitors (SSRIs), Serotonin-norepinephrine reuptake inhibitors (SNRIs), Monoamine oxidase inhibitors (MAOIs), and Tricyclic antidepressants. Typical limitation of known antidepressants are delayed onset of efficacy and low remission rates after multiple courses of pharmacotherapy, and for some antidepressants severe side-effects [Jick et al., Antidepressants and the risk of suicidal behaviors. Jama. Jul. 21, 2004; 292(3): 338-343].

In recent years, modulators of the N-Methyl-D-Aspartate (NMDA) receptors have received more attraction in treatment MDD, in particular treatment resistant depression (TRD). Especially, ketamine, an antagonist of the NMDA receptor, is used for treating MMD due to its antidepressant effect and fast onset. However, MDD treatment with ketamine has the drawbacks of psychometric side effects and requirement of intravenous administration.

NMDA receptors are tetrameric ligand-gated ion channels which are also involved in essential physiological processes such as synaptic plasticity and development. NMDA receptors are heterotetramers comprising two GluN1 subunits and two GluN2/GluN3 subunits. This means that they assemble as either diheteromeric or triheteromeric receptors. The majority of native NMDA receptors consist of two GluN1 subunits and two GluN2 subunits. Activation of the NMDA receptors requires simultaneous binding at two different binding sites. Glutamate, the major excitatory neurotransmitter in the central nervous system, binds to the GluN2 subunits and glycine binds to the GluN1 and GluN3 subunits.

Another known modulator of the NMDA receptor is D-cycloserine, which is a partial glycine site agonist. D-cycloserine has been intensively studied due to its neuroactive properties and potential utility in treatment of depression and depression disorders such as MDD [Heresco-Levy, U., Javitt, D. C., Gelfin, Y., Gorelik, E., Bar, M., Blanaru, M., Kremer, I., 2006. Controlled trial of d-cycloserine adjuvant therapy for treatment-resistant major depressive disorder. J. Affect. Disord. 93, 239-243] and PTSD [Olden, M., Wyka, K., Cukor, J., Peskin, M., Altemus, M., Lee, F. S., Finkelstein-Fox, L., Rabinowitz, T., Difede, J., 2017. Pilot study of a telehealth-delivered medication augmented exposure therapy protocol for PTSD. J. Nerv. Ment. Dis. 205, 154-160]. However, treatment of D-cycloserine suffers from frequent complaints of psychopathological stimulation such as anxiety, euphoria, agitation, feeling stimulated, dizziness/drowsiness, fatigue, headache, and gastrointestinal disturbance [Schade, S., Paulus, W., 2016. D-Cycloserine in neuropsychiatric diseases: a systematic review. Int. J. Neuropsychopharmacol] Urwyler et al., J. Med. Chem. 2009, 52, 5093-5107 discloses 3-acylamino-2-amonipropionic acid derivatives with affinity for the glycine site of the NMDA receptor.

Despite the longstanding interest in the field, there is evidently still an unmet need as regards developing efficient, well tolerated and active drugs for the treatment of depression and depression disorders such as MDD. A compound which is a modulator of the NMDA receptor with affinity for the glycine site may fulfil such unmet needs.

SUMMARY OF THE INVENTION

With this background, it is an object of the invention to provide compounds which are modulators of the NMDA receptor with affinity to the glycine site. In a first aspect of the invention is provided a compound of Formula I, or a pharmaceutically acceptable salt thereof, wherein:

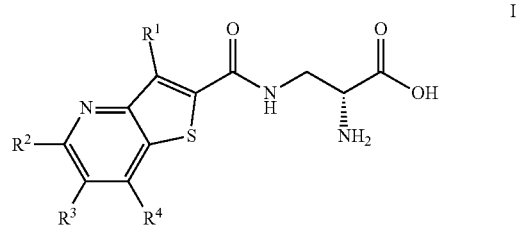

$R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $NR^aR^b$, $SR^cR^d$, $OR^6$, L-($OR^6$), and $R^7$;

$R^a$ and $R^b$ are independently selected from the group consisting of hydrogen and $C_{1-4}$ alkyl;

$R^c$ and $R^d$ are independently selected from the group consisting of hydrogen and $C_{1-4}$ alkyl;

$R^6$ is selected from the group consisting of hydrogen, $C_{1-4}$ alkyl, $C_{1-4}$ haloalkyl, $C_{1-4}$ hydroxyalkyl, and $C_{1-4}$ hydroxyhaloalkyl;

L represents a $C_{1-3}$ alkylene; and $R^7$ is selected from the group consisting of $C_{3-6}$ cycloalkyl, phenyl, 4, 5, or 6 membered heterocycle, and 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F.

In a further aspect is provided a pharmaceutical composition comprising a compound of formula I or a pharmaceutically acceptable salt thereof, and one or more pharmaceutically acceptable carrier or diluents.

In a further aspect is provided a method for the treatment of depression comprising the administration of a therapeutically effective amount of a compound of formula I, or acceptable salt thereof, or a pharmaceutical composition to a patient in need thereof.

In a further aspect is provided a compound of formula I, or a pharmaceutically acceptable salt thereof for use as a medicament comprising a compound of formula I, or a pharmaceutically acceptable salt thereof.

In a further aspect is provided a compound of formula I, or a pharmaceutically acceptable salt thereof, or a pharmaceutical composition for use in the treatment of depression.

In a further aspect is provided a use of a compound of formula I, or a pharmaceutically acceptable salt thereof, or a pharmaceutical composition for the manufacture of a medicament for use in the treatment of depression These and other aspects of the invention will become apparent upon reference to the following detailed description. It should be understood that the various aspects, embodiments, implementations and features of the invention mentioned herein may be claimed separately, or in any combination.

All references, including publications, patent applications and patents, cited herein are hereby incorporated by reference in their entirety and to the same extent as if each reference were individually and specifically indicated to be incorporated by reference and were set forth in its entirety.

Headings and sub-headings are used herein for convenience only and should not be construed as limiting the invention in any way.

Y-axis: Baseline-normalized power (dB); X-axis: bar to the left: 10% captisol; bar to the right: 20 mg/kg compound 1e.

Significance level for post-hoc comparison (relative to the vehicle group) is indicated: *<0.05.

Figure 2:
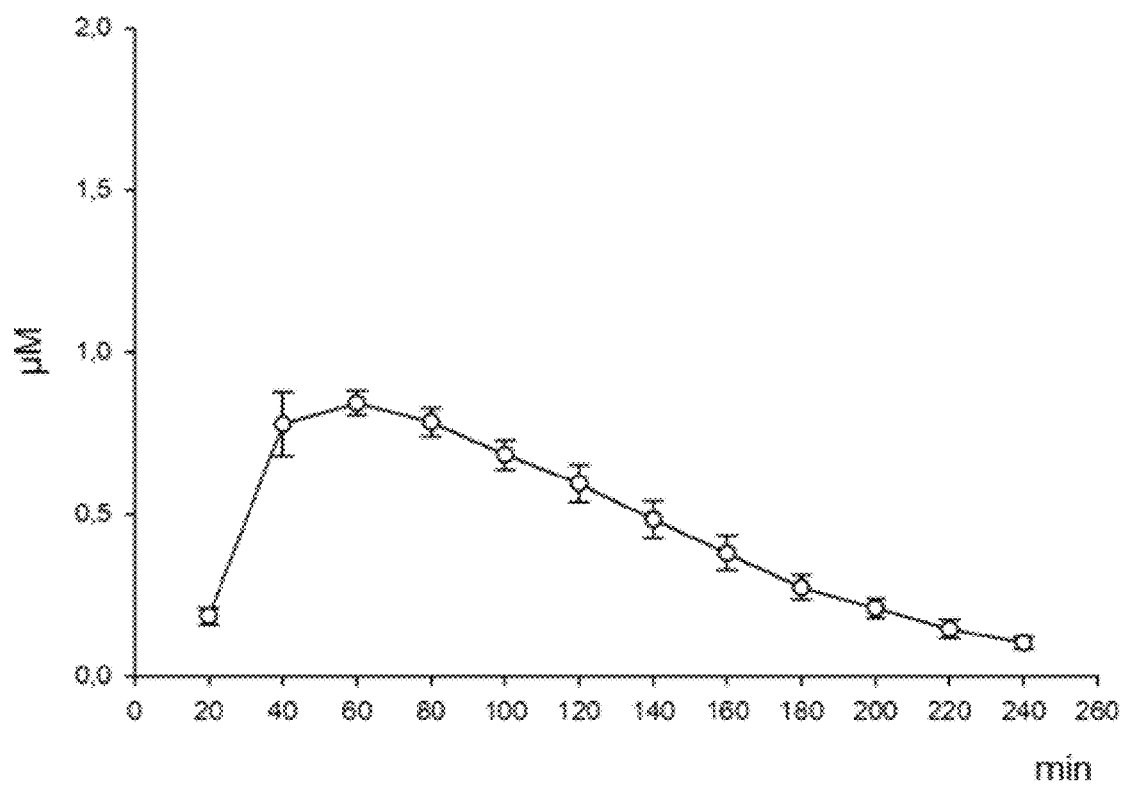

FIG. 2: Relationship between the concentration of compound 1e in the rat ventral hippocampus after systemic administration as a function of time according to example 4.

X-axis: time (minutes); Y-axis: concentration of tested compound (µM) in the rat ventral hippocampus; O: compound 1e.

DETAILED DESCRIPTION OF THE INVENTION

The inventors have identified new compounds that has affinity for the glycine site of the NMDA receptor as seen in table 2.

Figure 1:
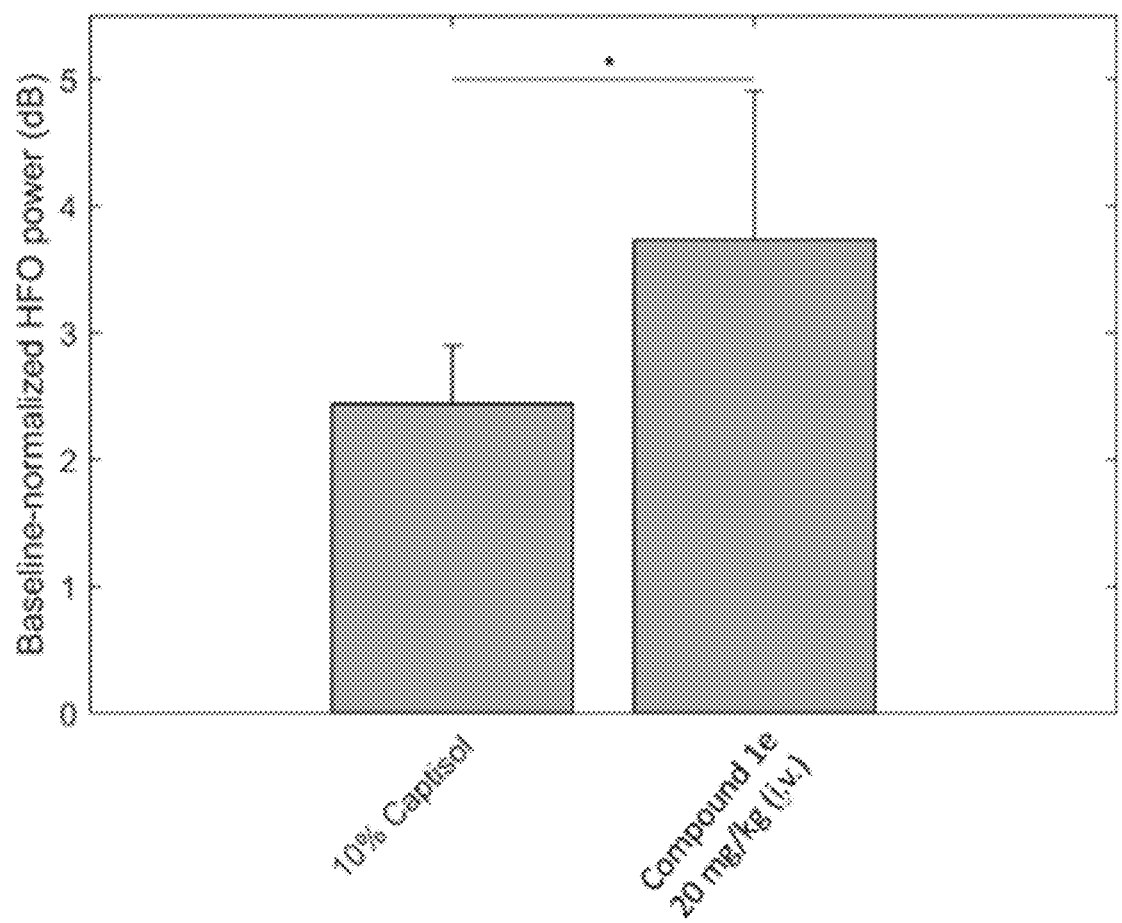
FIG. 1: Effects of compound 1e in Resting state Electroencephalography (rsEEG) obtained in the Nucleus accumbens according to example 3.

The inventors observed that the administration of compound 1e dosed at 20 mg/kg showed significant effects in rsEEG as shown in FIG. 1.

The inventors observed that considerable extracellular levels of the compound of the invention were observed in the rat ventral hippocampus after systemic administration, as shown in FIG. 2.

1. Definitions

As used herein, the terms "alkyl" refers to a linear (i.e. unbranched) or branched saturated hydrocarbon having from one up to eight carbon atoms, inclusive. Examples of such groups include, but are not limited to methyl, ethyl, 1-propyl, 2-propyl, 1-butyl, 2-butyl, 2-methyl-2-propyl, 2-methyl-1-butyl, n-hexyl, n-heptyl and n-octyl.

In some instances, the number of carbon atoms in a hydrocarbyl substituent (e.g., alkyl or cycloalkyl) is indicated by the prefix "$C_{x-y}$", wherein x is the minimum and y is the maximum number of carbon atoms in the substituent. Thus, for example, "$C_{1-3}$ alkyl" refers to an alkyl substituent containing from 1 to 3 carbon atoms.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

As used in the context of the present invention, the terms "halo" and "halogen" are used interchangeably and refer to an atom of the group consisting of F, Cl, I and Br.

As used herein, the term "alkoxy" refers to a moiety of the formula —OR', wherein R' indicates alkyl as defined above. In particular "$C_{1-4}$ alkoxy" refers to such moiety wherein the alkyl part has 1, 2, 3 or 4 carbon atoms. Examples of "$C_{1-4}$ alkoxy" include, but are not limited to methoxy, ethoxy, n-butoxy and tert-butoxy.

The term "haloalkyl" as used herein, means an alkyl group, as defined herein, in which one, two, three, four, five, six, seven, or eight hydrogen atoms are replaced by a halogen.

As used herein, the term "fluoroalkyl" refers to a straight chained or branched saturated hydrocarbon having from one to six carbon atoms inclusive substituted with one or more fluorine atoms. Examples include, but are not limited to, trifluoromethyl, pentafluoroethyl, 1-fluoroethyl, and 1,2-difluoroethyl.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyhaloalkyl," as used herein, means at least one —OH group, is appended to the parent molecular moiety through a haloalkyl group, as defined herein.

Similarly, the term "hydroxyfluoroalkyl," as used herein, means at least one —OH group, is appended to the parent molecular moiety through a fluoroalkyl group, as defined herein.

As used herein, the term "cyano", refers to a CN group appended to the parent molecule through the carbon atom of the CN group.

The term "heteroaryl," as used herein, refers to an aromatic monocyclic ring. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered aromatic monocyclic rings have three double bonds. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl.

The term "cycloalkyl," as used herein, refers to a carbocyclic ring system containing three to ten carbon atoms, zero heteroatoms and zero double bonds. The cycloalkyl may be monocyclic or bicyclic, wherein the two rings are bridged, fused, or spirocyclic. Representative examples of cycloalkyl include, but are not limited to, cyclopropyl, cyclobutyl, cyclopentyl, cyclohexyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

In the present context, the term an NMDA receptor partial glycine agonist is intended to indicate a compound that binds to and activates the NMDA receptor through the orthosteric glycine binding site and elicits partial efficacy relative to glycine.

In the present context, the term "therapeutically effective amount" of a compound is intended to indicate an amount sufficient to cure, alleviate or partially arrest the clinical manifestations of a given disease (e.g. depression) and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, e.g. by constructing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease (e.g. depression) from which the patient is suffering, such as administration of the active compound to alleviate the symptoms or complications, to delay the progression of the depression, to alleviate or relief the symptoms and complications, and/or to cure or eliminate the depression. The patient to be treated is preferably a mammal, in particular a human being. In the present context, "disease" can be used synonymous with disorder, condition, malfunction, dysfunction and the like.

2. Embodiments of the Invention

In the following, embodiments of the invention are disclosed. The first embodiment is denoted E1, the second embodiment is denoted E2 and so forth.

E1. compound of Formula I, or a pharmaceutically acceptable salt thereof, wherein:

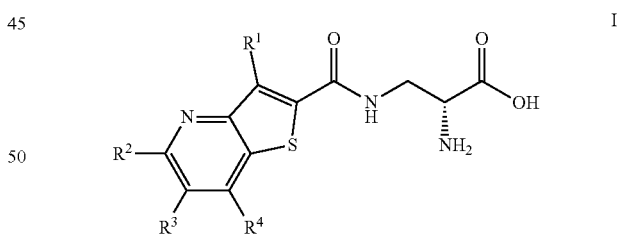

$R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $NR^aR^b$, $SR^cR^d$, $OR^6$, L-($OR^6$), and $R^7$;

$R^a$ and $R^b$ are independently selected from the group consisting of hydrogen and $C_{1-4}$ alkyl;

$R^c$ and $R^d$ are independently selected from the group consisting of hydrogen and $C_{1-4}$ alkyl;

$R^6$ is selected from the group consisting of hydrogen, $C_{1-4}$ alkyl, $C_{1-4}$ haloalkyl, $C_{1-4}$ hydroxyalkyl, and $C_{1-4}$ hydroxyhaloalkyl;

L represents a $C_{1-3}$ alkylene; and $R^7$ is selected from the group consisting of $C_{3-6}$ cycloalkyl, phenyl, 4, 5, or 6 membered heterocycle, and 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F.

E2. The compound according to embodiment E1, or a pharmaceutically acceptable salt thereof, wherein:

$R^1$ is selected from the group consisting of a hydrogen, halogen, and $C_{1-4}$ alkyl;

$R^2$ is selected from the group consisting of hydrogen, halogen, and $C_{1-4}$ alkyl;

$R^3$ is selected from the group consisting of hydrogen, halogen, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $OR^6$, and $R^7$;

$R^6$ is selected from the group consisting of $C_{1-4}$ alkyl, and $C_{1-4}$ haloalkyl; and $R^7$ is selected from the group consisting of a $C_{3-6}$ cycloalkyl and phenyl, wherein said cycloalkyl and phenyl is independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F.

E3. The compound according to any one of embodiments E1 to E2, or a pharmaceutically acceptable salt thereof, wherein $R^1$ is hydrogen.

E4. The compound according to any one of embodiments E1 to E3, or a pharmaceutically acceptable salt thereof, wherein $R^1$ is $C_{1-3}$ alkyl (e.g. ethyl).

E5. The compound according to any one of embodiments E1 to E4, or a pharmaceutically acceptable salt thereof, wherein $R^2$ is hydrogen.

E6. The compound according to any one of embodiments E1 to E5, or a pharmaceutically acceptable salt thereof, wherein $R^3$ is selected from the group consisting of hydrogen, $C_{1-4}$ alkyl, and halogen.

E7. The compound according to any one of embodiments E1 to E6, or a pharmaceutically acceptable salt thereof, wherein $R^3$ is selected from the group consisting of hydrogen, fluoro, and methyl.

E8. The compound according to any one of embodiments E1 to E7, or a pharmaceutically acceptable salt thereof, wherein $R^3$ is hydrogen.

E9. The compound according to any one of embodiments E1 to E8, or a pharmaceutically acceptable salt thereof, wherein $R^1$, $R^2$, and $R^3$ are hydrogen.

E10. The compound according to any one of embodiments E1 to E9, or a pharmaceutically acceptable salt thereof, wherein $R^4$ is $C_{1-4}$ alkyl.

E11. The compound according to any one of embodiments E1 to E10, or a pharmaceutically acceptable salt thereof, wherein $R^4$ is methyl.

E12. The compound according to any one of embodiments E1 to E9, or a pharmaceutically acceptable salt thereof, wherein $R^4$ is $C_{1-4}$ fluoroalkyl.

E13. The compound according to any one of embodiments E1 to E9, or a pharmaceutically acceptable salt thereof, wherein $R^4$ is halogen.

E14. The compound according to any one of embodiments E1 to E9, or a pharmaceutically acceptable salt thereof, wherein $R^4$ is phenyl unsubstituted or substituted with $C_{1-3}$ alkyl.

E15. The compound according to any one of embodiments E1 to E9, or a pharmaceutically acceptable salt thereof, wherein $R^4$ is $C_{1-4}$ alkoxy.

E16. The compound according to embodiment E15, or a pharmaceutically acceptable salt thereof, wherein $R^4$ is selected from the group consisting of isopropoxy, ethoxy, and methoxy.

E17. The compound according to any one of embodiments E1 to E9, or a pharmaceutically acceptable salt thereof, wherein $R^4$ is selected from the group consisting of $C_{1-4}$ alkyl, $C_{1-4}$ fluoroalkyl, $C_{3-6}$ cycloalkyl, $C_{1-4}$ hydroxyalkyl, $C_{1-4}$ alkoxy, $NR^aR^b$, $SR^cR^d$, halogen, and phenyl unsubstituted or substituted with ethyl.

E18. The compound according to any one of embodiments E1 to E9, or a pharmaceutically acceptable salt thereof, wherein $R^4$ is selected from the group consisting of methyl, ethyl, isopropyl, fluoromethyl, difluoromethyl, trifluoromethyl, hydroxymethyl, isopropoxy, ethoxy, methoxy, cyclopropyl, fluoro, bromo, dimethylamino, methylthio, and ethylphenyl.

E19. The compound according to embodiment E1, wherein the compound is selected from the group consisting of:

(R)-2-amino-3-[[7-thieno[3,2-b]pyridine-2-carbonyl]amino]propanoic acid;

(R)-2-amino-3-[(7-ethylthieno[3,2-b]pyridine-2-carbonyl)amino]propanoic acid;

(R)-2-amino-3-[[7-(difluoromethyl)thieno[3,2-b]pyridine-2-carbonyl]amino]propanoic acid;

(R)-2-amino-3-[(7-cyclopropylthieno[3,2-b]pyridine-2-carbonyl)amino]propanoic acid;

(R)-2-amino-3-[(7-methylthieno[3,2-b]pyridine-2-carbonyl)amino]propanoic acid;

(R)-2-amino-3-[(7-isopropylthieno[3,2-b]pyridine-2-carbonyl)amino]propanoic acid;

(R)-2-amino-3-[[7-(2-ethylphenyl)thieno[3,2-b]pyridine-2-carbonyl]amino]propanoic acid;

(R)-2-amino-3-[(7-methoxythieno[3,2-b]pyridine-2-carbonyl)amino]propanoic acid;

(R)-2-amino-3-[[7-(trifluoromethyl)thieno[3,2-b]pyridine-2-carbonyl]amino]propanoic acid;

(R)-2-amino-3-[(7-ethoxythieno[3,2-b]pyridine-2-carbonyl)amino]propanoic acid;

(R)-2-amino-3-[(7-isopropoxythieno[3,2-b]pyridine-2-carbonyl)amino]propanoic acid;

(R)-2-amino-3-[(7-bromothieno[3,2-b]pyridine-2-carbonyl)amino]propanoic acid;

(R)-2-amino-3-[(7-hydroxymethylthieno[3,2-b]pyridine-2-carbonyl)amino]propanoic acid;

(R)-2-amino-3-[[7-(fluoromethyl)thieno[3,2-b]pyridine-2-carbonyl]amino]propanoic acid;

(R)-2-amino-3-[(6-fluoro-7-methyl-thieno[3,2-b]pyridine-2-carbonyl)amino]propanoic acid; and (R)-2-amino-3-[(6,7-dimethylthieno[3,2-b]pyridine-2-carbonyl)amino]propanoic acid; or a pharmaceutically acceptable salt thereof.

E20. The compound according to embodiments E1, wherein the compound is (R)-2-amino-3-[(7-methylthieno[3,2-b]pyridine-2-carbonyl)amino]propanoic acid, or a pharmaceutically acceptable salt thereof.

E21. A pharmaceutical composition comprising a compound, or a pharmaceutically acceptable salt thereof, according to any one of embodiments E1 to E20 and one or more pharmaceutically acceptable carriers or diluents.

E22. A compound or a pharmaceutically acceptable salt thereof according to any one of embodiments E1 to E20 for use as a medicament.

E23. A compound, or a pharmaceutically acceptable salt thereof, or a pharmaceutical composition according to any one of embodiments E1 to E21 for use in the treatment of depression.

E24. The compound or a pharmaceutical composition according to embodiment E23, wherein the depression is selected from the group consisting of major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

E25. The compound or a pharmaceutical composition according to embodiment E24, wherein the depression is major depressive disorder E26. The compound or a pharmaceutical composition according to embodiment E24, wherein the depression is treatment-resistant depression E27. A compound, or a pharmaceutically acceptable salt thereof, or a pharmaceutical composition according to any one of embodiments E1 to E21 for use in the treatment of a condition selected from suicidal ideation, bipolar disorder (including bipolar depression), obsessive compulsive disorder and status epilepticus.

E28. The compound, or a pharmaceutically acceptable salt thereof, or a pharmaceutical composition according to embodiment E27 for use in the treatment of suicidal ideation.

E29. A method for the treatment of depression comprising the administration of a therapeutically effective amount of a compound or a pharmaceutically acceptable salt thereof, or a pharmaceutical composition according to any one of embodiments E1 to E21 to a patient in need thereof.

E30. The method for the treatment of depression according to embodiment E29, wherein the depression is selected from the group consisting of major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

E31. The method for treatment of depression according to any one of embodiments E29 to E30, wherein the depression is major depressive disorder E32. The compound or a pharmaceutical composition according to any one of embodiments E29 to E30, wherein the depression is treatment-resistant depression.

E33. A method for treating a condition selected from suicidal ideation, bipolar disorder (including bipolar depression), obsessive compulsive disorder and status epilepticus, comprising the administration of a therapeutically effective amount of a compound or a pharmaceutically acceptable salt thereof, or a pharmaceutical composition according to any one of embodiments E1 to E21 to a patient in need thereof.

E34. The method for treating suicidal ideation comprising the administration of a therapeutically effective amount of a compound or a pharmaceutically acceptable salt thereof, or a pharmaceutical composition according to any one of embodiments E1 to E21 to a patient in need thereof.

E35. Use of a compound or a pharmaceutically acceptable salt thereof, or a pharmaceutical composition according to any one of embodiments E1 to E21 for the manufacture of a medicament for use in the treatment of depression.

E36. The use of a compound or pharmaceutical composition according to embodiment E35, wherein the depression is selected from the group consisting of major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

Reference to compounds encompassed by the invention includes the free substance (zwitter ion) of compounds of the invention, pharmaceutically acceptable salts of compounds of the invention, such as acid addition salts or base addition salts, and polymorphic and amorphic forms of compounds of the invention and of pharmaceutically acceptable salts thereof. Furthermore, the compounds of the invention and pharmaceutically acceptable salts thereof may potentially exist in unsolvated as well as in solvated forms with pharmaceutically acceptable solvents such as water, ethanol and the like. Both solvated and unsolvated forms are encompassed by the present invention.

Compound names can be assigned by using the Struct=Name naming algorithm as part of CHEMDRAW®.

It should be understood that the compounds of the invention may possess tautomeric forms, stereoisomers, geometric isomers, and that these also constitute embodiments of the invention.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention. Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

Included in this invention are also isotopically labelled compounds, which are similar to those claimed in formula I, wherein one or more atoms are represented by an atom of the same element having an atomic mass or mass number different from the atomic mass or mass number usually found in nature (e.g., $^2$H, $^3$H, $^{11}$C, $^{13}$C, $^{15}$N, $^{18}$F and the like).

Particular mention is made of $^2$H substituted compounds i.e. compounds wherein one or more H atoms are represented by deuterium.

In one embodiment of the invention one or more of the hydrogen atoms of the compound of formula I are represented by deuterium. It is recognized that elements are present in natural isotopic abundances in most synthetic compounds, and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan.

In one embodiment, designation of a position as "D" in a compound has a minimum deuterium incorporation of greater than about 60% at that position such as greater than about 70% at that position such as greater than about 80% at that position such as greater than about 85% at that position. In a further embodiment, designation of a position as "D" in a compound has a minimum deuterium incorporation of greater than about 90% at that position such as greater than about 95% at that position such as greater than about 97% at that position such as greater than about 99% at that position.

a. Pharmaceutically Acceptable Salts

The compounds of this invention are generally utilized as the free substance or as a pharmaceutically acceptable salt thereof. When a compound of formula I contains a free base such salts may be prepared in a conventional manner by treating a solution or suspension of a free base of formula I with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts.

The term "pharmaceutically acceptable salts" include salts formed with inorganic and/or organic acids on the nitrogen atoms in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin, and sulfonic acids such as methanesulfonic acid, ethanesulfonic acid, toluenesulfonic acid and benzenesulfonic acid.

In an embodiment of the invention, the pharmaceutically acceptable salt is a hydrogen chloride salt.

In an embodiment of the invention, the pharmaceutically acceptable salt is a hydrogen bromide salt.

The term pharmaceutically acceptable salts also include salts formed with inorganic and/or organic bases on the acidic groups of compounds of formula I. Said bases may be selected from for example alkali metal bases, such as sodium hydroxide, lithium hydroxide, potassium hydroxide, alkaline earth bases, such as calcium hydroxide and magnesium hydroxide, and organic bases, such as trimethylamine.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

3. Conditions for Treatment

The invention encompasses use of the compounds of the invention for treatment of all diseases and disorders listed above.

As described above the present invention may be useful in the treatment of depression and depressive disorders. Hence in one embodiment, a compound of formula I or a pharmaceutically acceptable salt thereof is used for the treatment of depression.

The diagnosis of depression usually follows a clinical evaluation by a psychiatrist or other mental health professionals. The two most recognized sets of diagnostic criteria for major depressive disorder and other depressive, or mood disorders, are outlined in the DSM, Diagnostic and Statistical Manual of Mental Disorders, Fourth Edition, (DSM IV) published by the American psychiatric association and the ICD (ICD-10: International Statistical Classification of Diseases and Related Health Problems—10$^{th}$ Revision, published periodically by the World Health Organization) or any other psychiatric classification system.

Signs and symptoms of depression are for example depressed mood, loss of interest (anhendonia), weight or appetite changes, sleep problems, psychomotor activity (objective or subjective), fatigability, worthlessness, concentration difficulty, suicidal ideation, loss of confidence, sexual dysfunction and self-reproach.

Thus in an embodiment of the invention, treatment with compounds of the invention prevent, alter, reduce or alleviate one or more signs or symptoms of depression selected from the group consisting of depressed mood, loss of interest (anhendonia), weight or appetite changes, sleep problems, psychomotor activity (objective or subjective), fatigability, worthlessness, concentration difficulty, suicidal ideation, loss of confidence, sexual dysfunction and self-reproach. The skilled person is familiar with various test for measuring the improvement of depressive symptoms. Examples of test for measuring the improvements are but not limited to the HAM-D or MADRS scale.

In an embodiment the depression is major depressive disorder.

In a further embodiment the depression is treatment-resistant depression.

In a further embodiment the depression is selected from major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression.

Clinically used NMDA antagonist such as ketamine and dextromethorphan are generally effective in patients with neurophatic pain [Hy et al., Expert Rev Clin Pharmacol. 2011 May 1; 4(3):379-388]. Hence, in an embodiment of the invention, compound of formula I or a pharmaceutically acceptable salt thereof is used in the treatment of pain. In a further embodiment the pain is neuropathic pain.

Preclinical animal models has demonstrated pro-cognitive and antidepressant-like effects with the use of NDMA glycine site modulators[Peyrovian et al., Progress in Neuropsychopharmacology & Biological Psychiatry. 92 (2019) 387-404]. Hence, In an embodiment of the invention, a compound of formula I or a pharmaceutically acceptable salt thereof is used in the treatment of a condition selected from suicidal ideation, bipolar disorder (including bipolar depression), obsessive compulsive disorder and status epilepticus In a further embodiment a compound of formula I or a pharmaceutically acceptable salt thereof is used in the treatment of suicidal ideation.

In an embodiment of the invention, compound of formula I or a pharmaceutically acceptable salt thereof is used the treatment of a neurological disorder or neuropsychiatric disorder.

a. Combination Treatment

In an embodiment of the invention, the compounds of formula I are for use as stand-alone treatment as the sole active compound. In another embodiment of the invention, the compounds of formula I may be used in combination with other agents useful in the treatment of disorders such as depression. The terms "combined use", "in combination with" and "a combination of" and the like as used herein in the context of the method of the invention comprising the combined administration of therapeutically effective amounts of a compound of formula I, and another compound, which compound is useful in the treatment a neurodegenerative disease or disorder, is intended to mean the administration of a compound of formula I simultaneously or sequentially, in any order, together with said other compound.

The two compounds may be administered simultaneously or sequentially with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more other compounds useful in the treatment of depression when treatment with a compound of the invention initiated. In other instances, the patient may already be in treatment with a compound of the invention when treatment with one or more other compounds useful in the treatment of a depression or psychosis is initiated. In other instances, the treatment with a compound of the invention and treatment with one or more other compounds useful in the treatment of psychosis initiated at the same time.

b. Compounds for Combination Treatment

Examples of therapeutically active compounds which may advantageously be combined with compounds of the invention include sedatives or hypnotics, such as benzodiazepines; anticonvulsants, such as lamotrigine, valproic acid, topiramate, gabapentin, carbamazepine; mood stabilizers such as lithium; dopaminergic drugs, such as dopamine agonists and L-Dopa; drugs to treat ADHD, such as atomoxetine; psychostimulants, such as modafinil, ketamine, methylphenidate and amphetamine; other antidepressants, such as mirtazapine, mianserin, vortioxetine, cipralex, and buproprion; hormones, such as T3, estrogen, DHEA and testosterone; atypical antipsychotics, such as olanzapine, brexpiprazole and aripiprazole; typical antipsychotics, such as haloperidol; drugs to treat Alzheimer's diseases, such as cholinesterase inhibitors and memantine, folate; S-Adenosyl-Methionine; immunmodulators, such as interferons; opiates, such as buprenorphine; angiotensin II receptor 1 antagonists (AT1 antagonists); ACE inhibitors; statins; and alpha1 adrenergic antagonist, such as prazosin.

c. Administration Routes

The pharmaceutical compositions comprising a compound of formula I, either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route.

It will be appreciated that the route will depend on the general condition and age of the subject to be treated, the nature of the condition to be treated and the active ingredient.

d. Doses

In one embodiment, the compound of the present invention is administered in an amount from about 0.5 mg/kg body weight to about 50 mg/kg body weight per day. In particular, daily dosages may be in the range of 1 mg/kg body weight to about 30 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

In an embodiment the frequency of administration is 1, 2, 3, 4, or 5 times per day In an embodiment the frequency of administration is once weekly.

In an embodiment the frequency of administration is twice weekly.

A typical oral dosage for adults will be in the range of 100-3000 mg/day of a compound of the present invention, such as 700-2800 mg/day, such as 1000-2000 mg/day or 1200-1700 mg/day. Conveniently, the compounds of the invention are administered in a unit dosage form containing said compounds in an amount of about 100 to 1000 mg, such as 100 mg, 150 mg, 200 mg, 250 mg, 300 mg, 350 mg, 400 mg, 450 mg, 500 mg, 750 mg or up to 1000 mg of a compound of the present invention.

In an embodiment the frequency of administration is 1, 2, 3, 4, or 5 times per day In an embodiment the frequency of administration is once weekly.

In an embodiment the frequency of administration is twice weekly.

A typical IV dosage for adults will be in the range of 20-300 mg/day of a compound of the present invention, such as 50-200 mg/day, such as 70-150 mg/day or 75-125 mg/day. Conveniently, the compounds of the invention are administered in a unit dosage form containing said compounds in an amount of about 10 to 300 mg, such as 10 mg, 20 mg, 50 mg, 100 mg, 150 mg, 200 mg, 250 mg, 300 mg of a compound of the present invention.

In one embodiment the frequency of administration is once weekly.

In an embodiment the frequency of administration is twice weekly.

4. Pharmaceutical Formulations and Excipients

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula I, such as one of the compounds disclosed in the Experimental Section herein. The present invention also provides a process for making a pharmaceutical composition comprising a compound of formula I. The pharmaceutical compositions according to the invention may be formulated with pharmaceutically acceptable excipients in accordance with conventional techniques such as those disclosed in Remington, "The Science and Practice of Pharmacy", 22$^{th}$ edition (2013), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an oral-dispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

5. Compounds of the Invention

TABLE 1

Exemplified compounds of the invention

| Example | Name | structure |
|---------|------|-----------|
| Compound 1a | (R)-2-amino-3-[[7-thieno[3,2-b]pyridine-2-carbonyl]amino]propanoic acid | 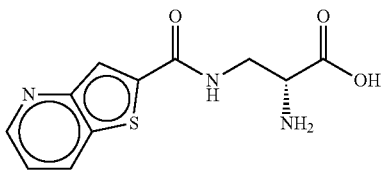 |

TABLE 1-continued

Exemplified compounds of the invention

| Example | Name | structure |
|---|---|---|
| Compound 1b | (R)-2-amino-3-[(7-ethylthieno[3,2-b]pyridine-2-carbonyl)amino]propanoic acid | 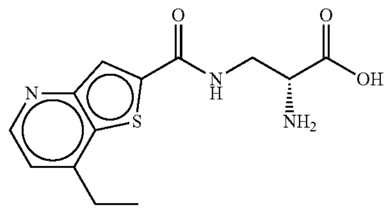 |
| Compound 1c | (R)-2-amino-3-[[7-(difluoromethyl)thieno[3,2-b]pyridine-2-carbonyl]amino]propanoic acid | 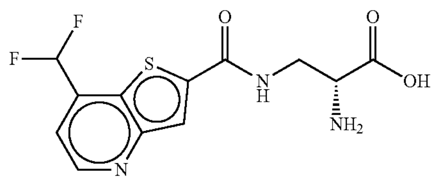 |
| Compound 1d | (R)-2-amino-3-[(7-cyclopropylthieno[3,2-b]pyridine-2-carbonyl)amino]propanoic acid | 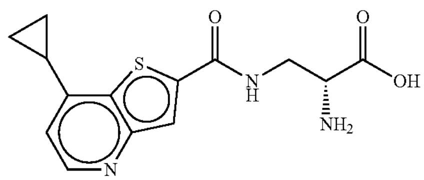 |
| Compound 1e | (R)-2-amino-3-[(7-methylthieno[3,2-b]pyridine-2-carbonyl)amino]propanoic acid | 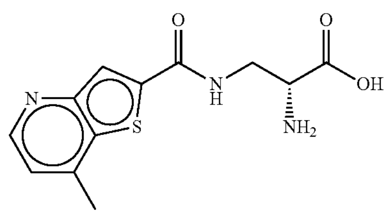 |
| Compound 1f | (R)-2-amino-3-[(7-isopropylthieno[3,2-b]pyridine-2-carbonyl)amino]propanoic acid | 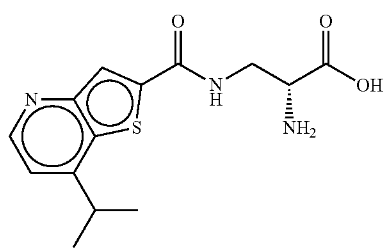 |
| Compound 1g | (R)-2-amino-3-[[7-(2-ethylphenyl)thieno[3,2-b]pyridine-2-carbonyl]amino]propanoic acid | 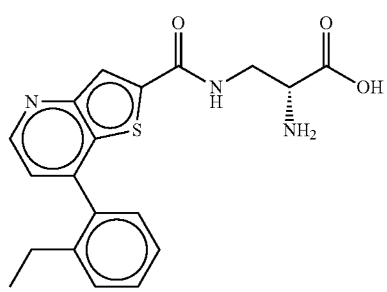 |
| Compound 1h | (R)-2-amino-3-[(7-methoxythieno[3,2-b]pyridine-2-carbonyl)amino]propanoic acid | 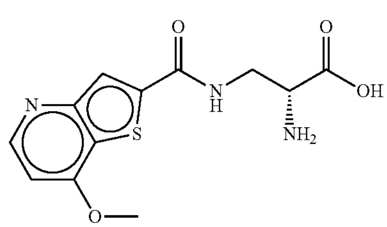 |

TABLE 1-continued

Exemplified compounds of the invention

| Example | Name | structure |
| --- | --- | --- |
| Compound 1i | (R)-2-amino-3-[[7-(trifluoromethyl)thieno[3,2-b]pyridine-2-carbonyl]amino]propanoic acid | 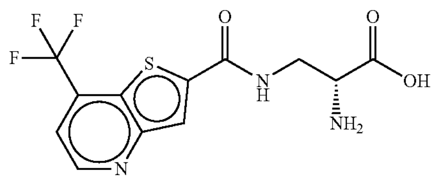 |
| Compound 1j | (R)-2-amino-3-[(7-ethoxythieno[3,2-b]pyridine-2-carbonyl)amino]propanoic acid | 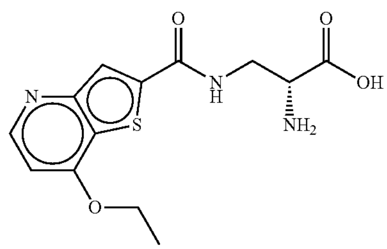 |
| Compound 1k | (R)-2-amino-3-[(7-isopropoxythieno[3,2-b]pyridine-2-carbonyl)amino]propanoic acid | 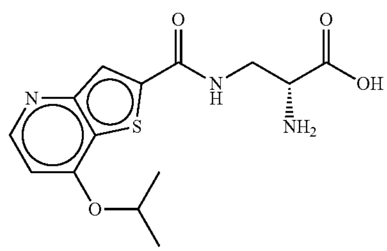 |
| Compound 1l | (R)-2-amino-3-[(7-bromothieno[3,2-b]pyridine-2-carbonyl)amino]propanoic acid | 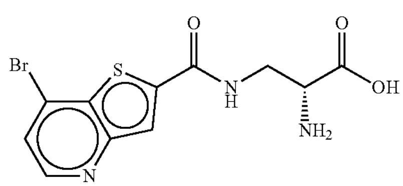 |
| Compound 1m | (R)-2-amino-3-[(7-hydroxymethylthieno[3,2-b]pyridine-2-carbonyl)amino]propanoic acid | 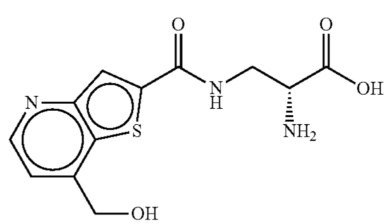 |
| Compound 1n | (R)-2-amino-3-[[7-(fluoromethyl)thieno[3,2-b]pyridine-2-carbonyl]amino]propanoic acid | 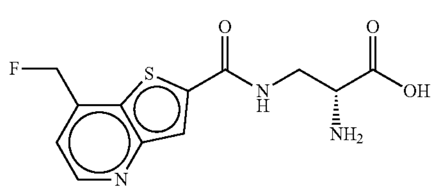 |
| Compound 1o | (R)-2-amino-3-[(6-fluoro-7-methyl-thieno[3,2-b]pyridine-2-carbonyl)amino]propanoic acid | 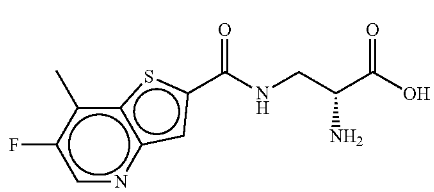 |

TABLE 1-continued

Exemplified compounds of the invention

| Example | Name | structure |
|---|---|---|
| Compound 1p | (R)-2-amino-3-[(6,7-dimethylthieno[3,2-b]pyridine-2-carbonyl)amino]propanoic acid | 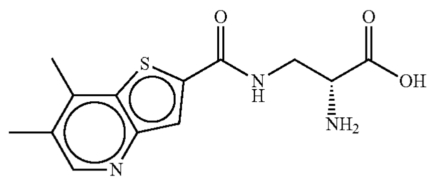 |

6. Experimental Section a. General Schemes for Preparing Compounds of the Invention

The compounds of the present invention of the general formula I, wherein $R^1$, $R^2$, $R^3$ and $R^4$ are as defined above can be prepared by the methods outlined in the following reaction Schemes 1-15 and in the examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

The schemes may involve the use of selective protecting groups during the synthesis of the compounds of the invention. One skilled in the art would be able to select the appropriate protecting group for a particular reaction. It may be necessary to incorporate protection and de-protection strategies for substituents such as amino, amido, carboxylic acid and hydroxyl groups in the synthetic methods described below to synthesize the compounds of Formula I. Methods for protection and de-protection of such groups are well known in the art, and may be found in T. Green, et al., Protective Groups in Organic Synthesis, 1991, 2nd Edition, John Wiley & Sons, New York.

The schemes in this section are representative of methods useful in synthesizing the compounds of the present invention. They are not intended to constrain the scope of the invention in any way.

Scheme 1

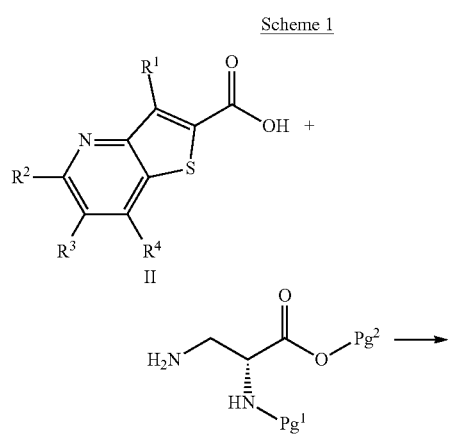

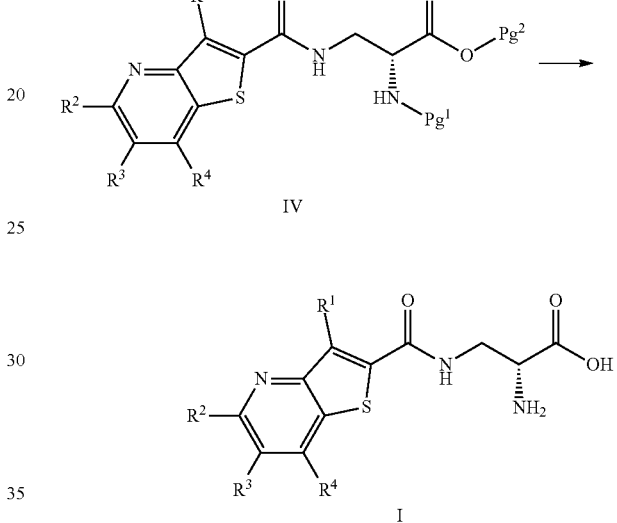

Compounds of general formula I (Scheme 1) may be prepared from compounds with general formula IV by standard de-protection procedures. As an example, compounds of general formula I (Scheme 1) may be prepared from compounds with general formula IV where $Pg^1$ is Cbz and $Pg^2$ is benzyl using conditions such as HBr in acetic acid.

Compounds with general formula IV may be prepared by reacting protected amines of general formula III with carboxylic acids (or salt thereof) of general formula II by standard peptide coupling such as using O-(Benzotriazol-1-yl)-N,N,N',N'-tetramethyluronium tetrafluoroborate in the presence of a base such as N,N-diisopropylethylamine in a solvent such as N,N-dimethylformamide.

Scheme 2

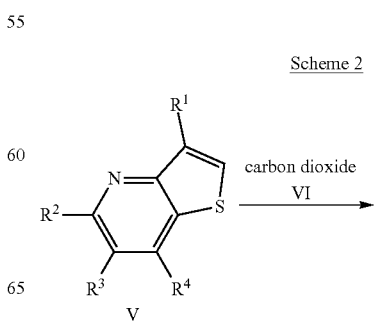

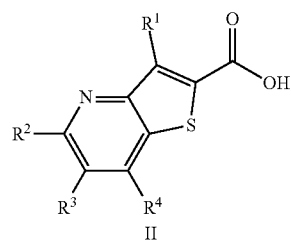

II

Thieno[3,2-b]pyridine-2-carboxylic acids (or salt thereof) of general formula II (Scheme 2), can be obtained from thieno[3,2-b]pyridine of general formula V by deprotonation at low temperature using a base such as lithium diisopropylamide (LDA) in a solvent such as tetrahydrofuran (THF) followed by the addition of carbon dioxide VI and allowing the reaction mixture to reach room temperature.

Scheme 3

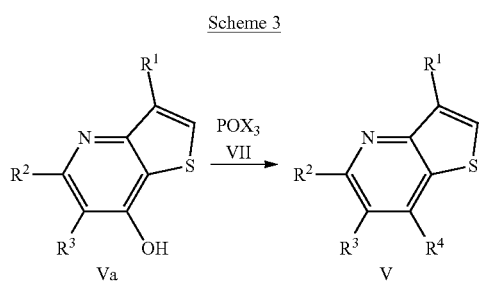

Thieno[3,2-b]pyridine of general formula V where $R^4$ is Cl, is commercially available. Thieno[3,2-b]pyridine of general formula V where $R^4$ is Br (Scheme 3) can be obtained by treatment of compound Va with a reagent such as Phosphorus(V) oxybromide VII at elevated temperature.

Scheme 4

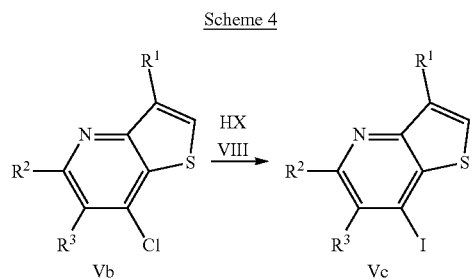

Thieno[3,2-b]pyridine of general formula Vc (Scheme 4), can be obtained by treatment of compound Vb under reaction conditions such as HI in water at elevated temperature.

Scheme 5

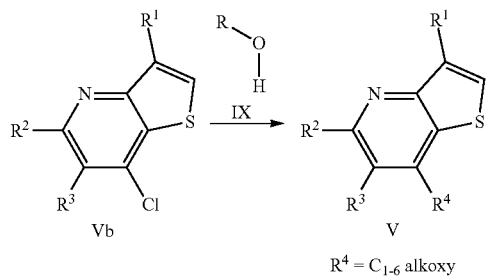

Thieno[3,2-b]pyridine of general formula V (Scheme 5) where R4 is $C_{1-6}$ alkoxy can be obtained by treatment of compound Vb under reaction conditions such as in the presence of an alcohol ROH IX, deprotonated by a base such as sodium, at elevated temperature.

Scheme 6

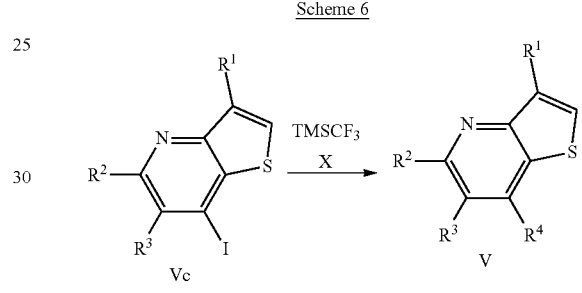

Thieno[3,2-b]pyridine of general formula V (Scheme 6) where $R^4$ can be trifluoromethyl as described in general Formula I can be obtained by treatment of compound Vc, under reaction conditions such as in the presence of metal catalyst such as copper iodide, a reagent such as potassium fluoride, and a perfluorinated precursor such as trimethyl (trifluoromethyl)silane (TMSCF$_3$) X.

Scheme 7

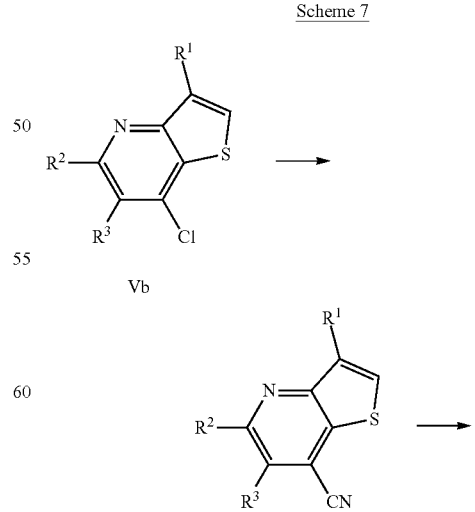

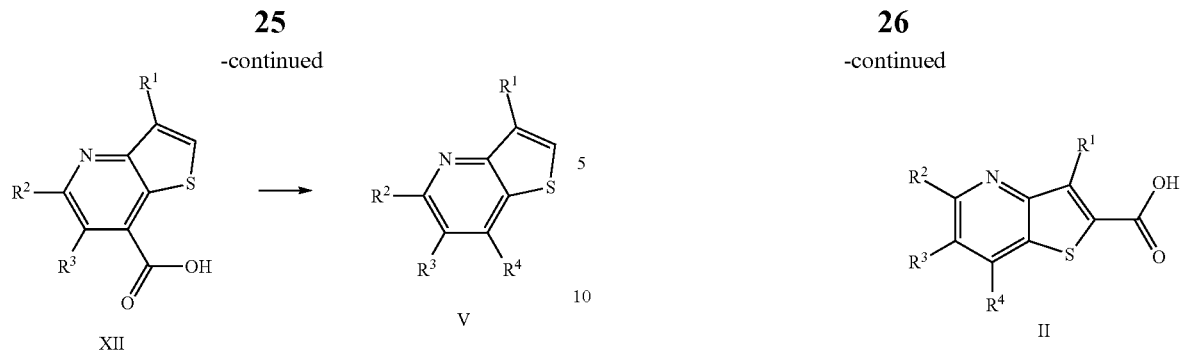

Thieno[3,2-b]pyridine of general formula V (Scheme 7) where $R^4$ can be —CH2-OH as described in general Formula I can be obtained from compound XII, by treatment with a reducing agent such as sodium borohydride. Compound XII can be obtained from compound XI in reaction conditions such as hydrochloric acid in methanol. Compound XI can be obtained from compound Vb using a reagent such as zinc cyanide in the presence of metal catalysts such as [1,1'-Bis(diphenylphosphino)ferrocene]dichloropalladium(II), complex with dichloromethane and bis(dibenzylideneacetone)palladium and zinc.

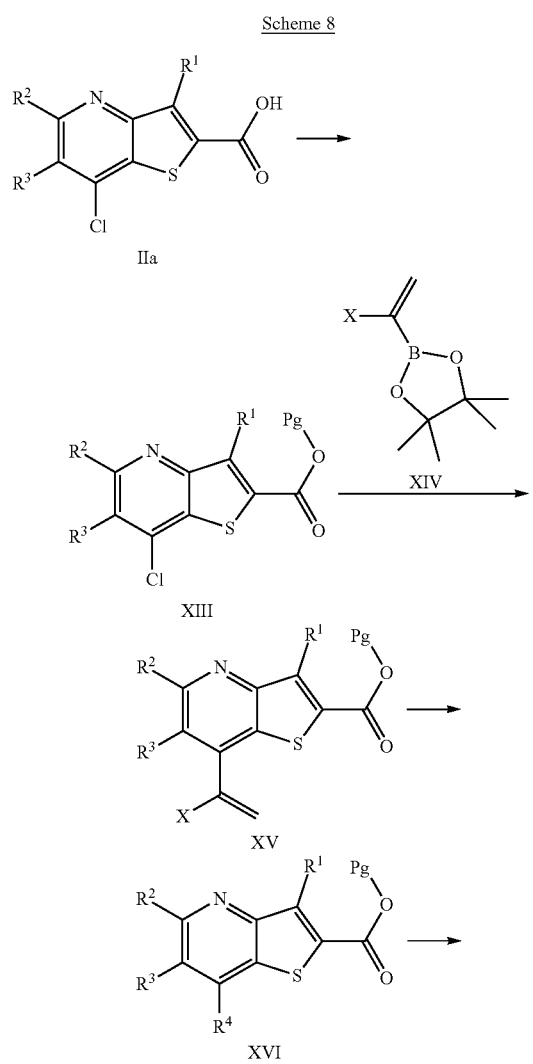

Thieno[3,2-b]pyridine-2-carboxylic acid of general formula II (or salt thereof), (Scheme 8) where $R^4$ can be an ethyl as described in general Formula I can be prepared from the corresponding ester where Pg can be methyl as in compounds of general formula XVI by hydrolysis under aqueous conditions in a variety of conditions known to chemists skilled in the art. Compounds of general formula XVI can be obtained from compounds of general formula XV, where X can be hydrogen, under reaction conditions such as hydrogenation in the presence of a catalyst such as palladium on carbon. Compounds of general formula XV can be obtained by reacting compounds of general formula XIII with reagents of general formula XIV in the presence of a catalyst such as [1,1'-Bis(diphenylphosphino)ferrocene]dichloropalladium(II), complex with dichloromethane and a base such as potassium carbonate. Compounds of general formula XIII where Pg is methyl can be obtained from compounds of general formula IIa by treatment with a reagent such as thionyl chloride in methanol as solvent.

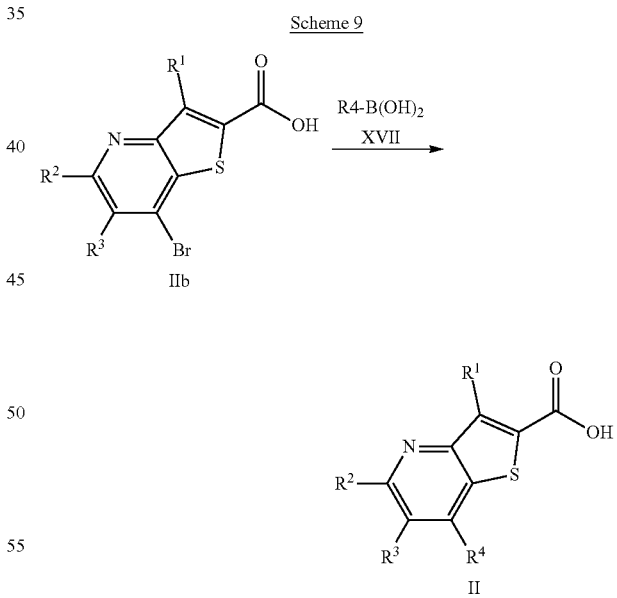

Compounds of general formula II (or salt thereof) where $R^4$ is as described for Formula I (Scheme 9) can be obtained by reacting compounds of general formula IIb, with reagents of general formula XVII under reaction conditions such as in the presence of a catalyst such as [1,1'-Bis(diphenylphosphino)ferrocene]dichloropalladium(II), complex with dichloromethane or [1,1'-Bis(di-tert-butylphosphino)ferrocene]dichloropalladium(II) and a base such as sodium carbonate.

Scheme 10

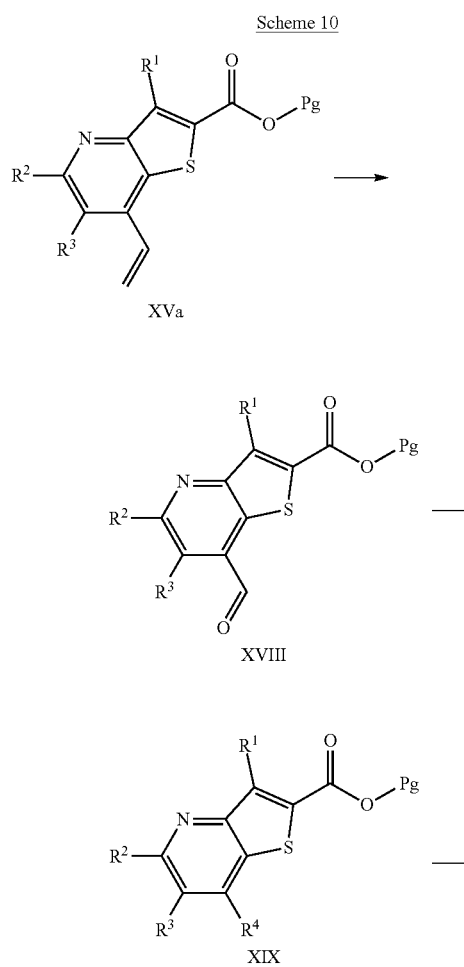

Scheme 11

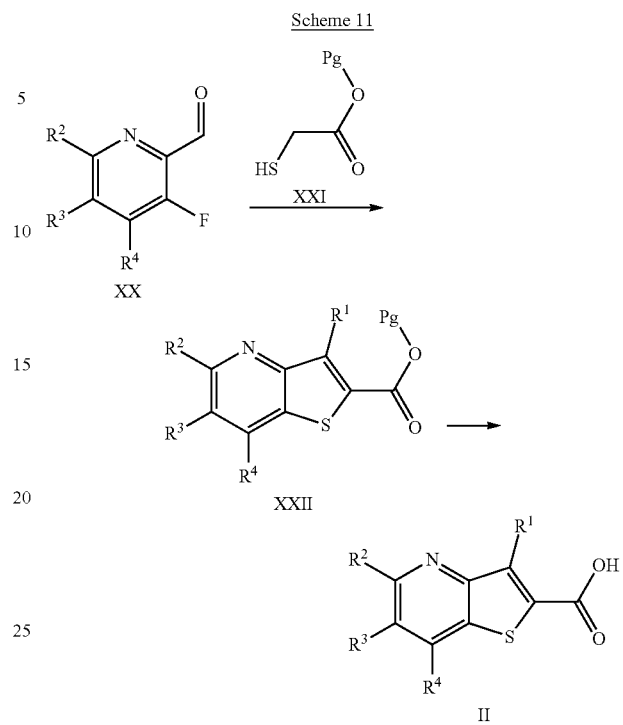

Thieno[3,2-b]pyridine-2-carboxylic acid of general formula II, where $R^1$ is hydrogen (or salt thereof) (Scheme 11) can be prepared from the corresponding ester where Pg can be methyl as in compounds of general formula XXII by hydrolysis under aqueous conditions known to chemists skilled in the art. Compounds of general formula XXII can be prepared by reaction of aldehydes of general formula XX with a reagent of general formula XXI in the presence of a base such as triethylamine.

Scheme 12

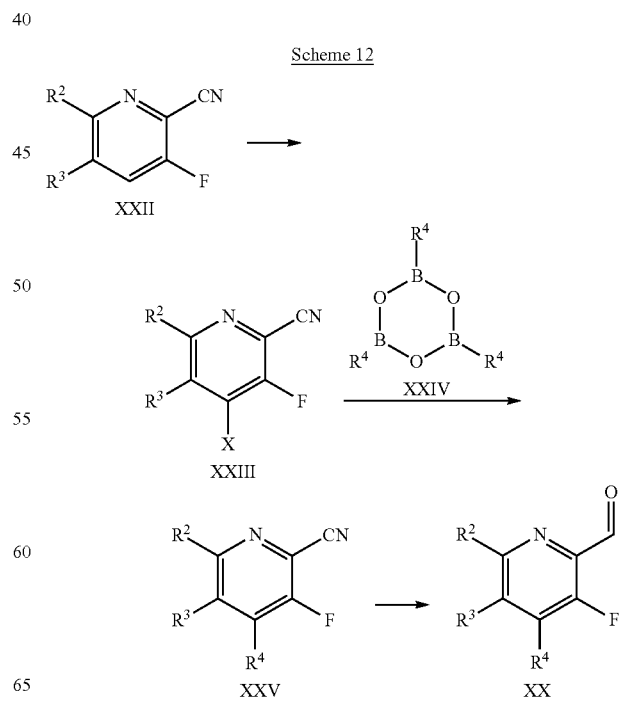

Thieno[3,2-b]pyridine-2-carboxylic acid (or salt thereof) of general formula II (Scheme 10) where $R^4$ can be difluoromethyl as described in general Formula I can be prepared from the corresponding ester where Pg can be methyl as in compounds of general formula XIX by hydrolysis in aqueous conditions in a variety of conditions known to chemists skilled in the art. Compounds of general formula XIX where $R^4$ can be difluoromethyl can be prepared by treatment of a compound of general formula XVIII with reagents such as (diethylamino)sulfur trifluoride. Compounds of general formula XVIII can be prepared from compounds of general formula XVa, in the presence of ozone followed by treatment with a reagent such as triphenyl phosphine.

Aldehydes of general formula XX (Scheme 12) can be prepared from compounds of general formula XXV using a reducing reagent such as diisobutylaluminum hydride. Compounds of general formula XXV can be prepared from compounds of general formula XXIII, where X is an halogen such as iodine, by reaction with a reagent such as XXIV in the presence of a catalyst such as [1,1'-Bis(diphenylphosphino)ferrocene]dichloropalladium(II), complex with dichloromethane and a base such as potassium phosphate. Compounds of general formula XXIII can be prepared from compounds of general formula XXII, via deprotonation using a base such as lithium diisopropylamide followed by the addition of an electrophilic halogen species, such as molecular iodine.

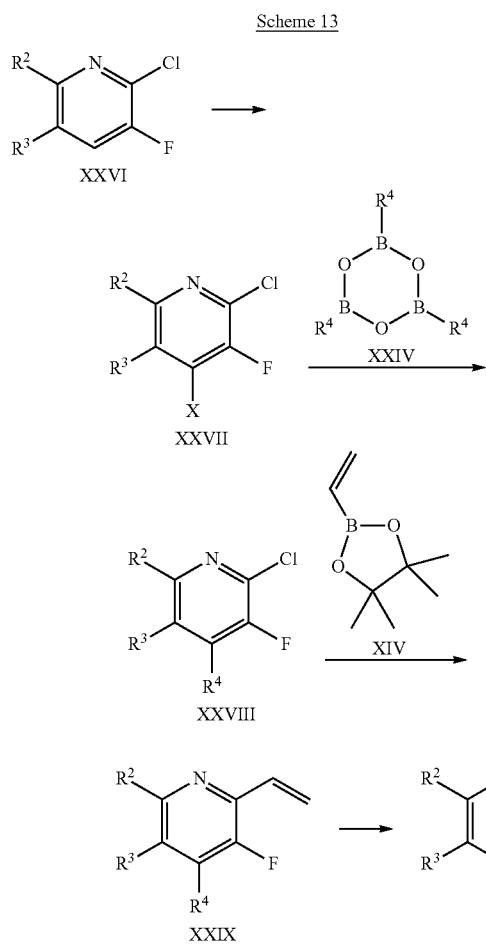

Aldehydes of general formula XX (Scheme 13) can be prepared from compounds of general formula XXIX, under reaction conditions such in the presence of ozone followed by treatment with reagent such as triphenyl phosphine. Compounds of general formula XXIX can be obtained by reacting compounds of general formula XXVIII with reagents of general formula XIV in the presence of a catalyst such as [1,1'-Bis(diphenylphosphino)ferrocene]dichloropalladium(II), complex with dichloromethane and a base such as potassium carbonate. Compounds of general formula XXVIII can be prepared from compounds of general formula XXVII, where X is an halogen such as iodine, by reaction with a reagent such as XXIV in the presence of a catalyst such as [1,1'-Bis(diphenylphosphino)ferrocene]dichloropalladium(II), complex with dichloromethane and a base such as potassium carbonate. Compounds of general formula XXVII can be prepared from compounds of general formula XXVI, via deprotonation using a base such as lithium diisopropylamide followed by the addition of an electrophilic halogen species such as molecular iodine.

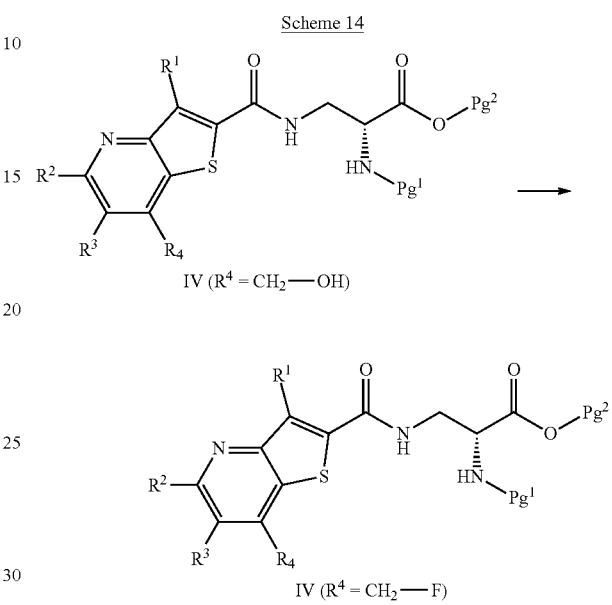

Compounds of general formula IV (Scheme 14) where $R^4$=—$CH_2F$ may be prepared from compounds of general formula IV where $R^4$=—$CH_2OH$ using reagents such as (diethylamino)sulfur trifluoride.

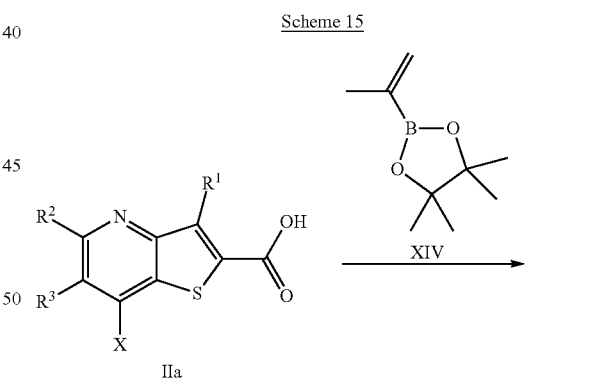

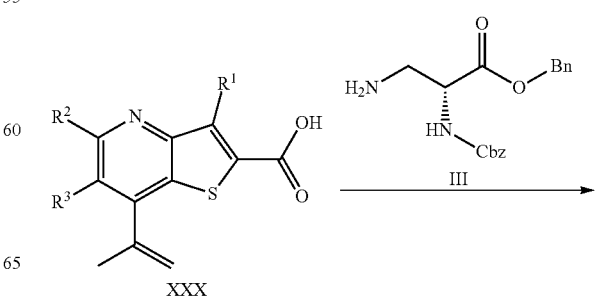

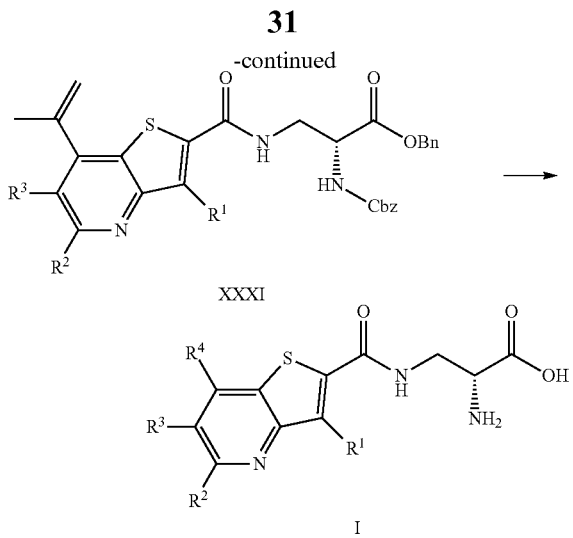

Compounds of general formula I where $R^4$ is isopropyl (Scheme 15) may be prepared from compounds with general formula XXXI under reaction conditions such as hydrogenation in the presence of a catalyst such as palladium on carbon. Compounds with general formula XXXI may be prepared by reacting protected amines of general formula III with carboxylic acids of general formula XXX by standard peptide coupling methods such as using O-(Benzotriazol-1-yl)-N,N,N',N'-tetramethyluronium tetrafluoroborate in the presence of a base such as N,N-diisopropylethylamine in a solvent such as N,N-dimethylformamide. Compounds of general formula XXX can be obtained by reacting compounds of general formula IIa, where X is Cl or Br respecively, with a reagent of formula XIV under reaction conditions such as in the presence of a catalyst such as [1,1'-Bis(di-tert-butylphosphino)ferrocene]dichloropalladium(II) and a base such as potassium carbonate.

b. General Methods

LC-MS Methods

Analytical LC-MS Data were obtained using one of the methods identified below.

Method AA: A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method BB: A Waters Acquity UPLC-MS was used. Column: Acquity UPLC BEH C18 1.7 μm; 2.1×50 mm; Column temperature: 60° C.; Solvent system: A=water/trifluoroacetic acid (99.5:0.5) and B=acetonitrile/water/trifluoroacetic acid (94.965:5:0.035); Method: Linear gradient elution with A:B=90:10 to 0:100 in 1.0 minutes and with a flow rate of 1.2 mL/min.

Preparative HPLC

Preparative-HPLC (Method A): Instrument: Gilson GX-281 Liquid Handler, SHIMADZU LC-8A LCMS2010; Column: YMC-Actus Triart C18 150*30 5 μm; Mobile Phase A: water (0.05% HCl v/v); Mobile phase B: MeCN; Gradient: B from 5% to 35% in 10 min then hold at 100% for 3 min; FlowRate (ml/min): 25; Column temperature: 35° C. and Wavelength: 220 nm 254 nm Preparative HPLC (Method B): Instrument: Gilson GX-215, Gilson 322 Pump, Gilson 156 UV Detector; Column: YMC-Actus Triart C18 150*30 5 μm; Mobile Phase A: water (0.05% HCl v/v); Mobile phase B: MeCN; Gradient: B from 0% to 28% in 10 min then hold at 100% for 3 min; FlowRate (ml/min): 25; Column temperature: 40° C. and Wavelength: 220 nm 254 nm Preparative HPLC (Method C): Instrument: Gilson GX-281 Liquid Handler, Gilson 322 Pump, Gilson 156 UV Detector; Column: Xtimate C18 150*25 mm*5 μm; Mobile Phase A: water (0.05% ammonia hydroxide v/v); Mobile phase B: MeCN; Gradient: from 42% to 72% in 10 min then hold at 100% for 2.5 min; Flow Rate (ml/min): 25; Column temperature: 25° C. and Wavelength: 220 nm 254 nm Preparative HPLC (Method D): Instrument: Gilson GX-281, Gilson 322 Pump, Gilson 156 UV Detector; Column: Gemini 150*25 mm*5 μm; Mobile Phase A: water (0.05% ammonia hydroxide v/v); Mobile phase B: MeCN; Gradient: B from 52% to 82% in 10 min then hold at 100% for 2 min; FlowRate (ml/min): 25; Column temperature: 30° C. and Wavelength: 220 nm 254 nm.

Preparative HPLC (Method E): Instrument: Gilson GX-281 Liquid Handler, Gilson 322 Pump, Gilson 156 UV Detector; Column: Xtimate C18 150*25 mm*5 μm; Mobile Phase A: water (0.05% ammonia hydroxide v/v); Mobile phase B: MeCN; Gradient: B from 64% to 94% in 10 min then hold at 100% for 2.5 min; Flow Rate (ml/min): 25; Column temperature: 25° C. and Wavelength: 220 nm 254 nm.

Preparative HPLC (Method F): Instrument: Gilson GX-281 Liquid Handler, Gilson 322 Pump, Gilson 156 UV Detector; Column: Xtimate C18 150*25 mm*5 μm; Mobile Phase A: water (0.05% ammonia hydroxide v/v); Mobile phase B: MeCN; Gradient: from 57% to 87% in 10 min then hold at 100% for 2.5 min; Flow Rate (ml/min): 25; Column temperature: 25° C. and Wavelength: 220 nm 254 nm.

Preparative HPLC (Method G): Instrument: Gilson GX-215 Liquid Handler, Gilson 322 Pump, Gilson 156 UV Detector; Column: DYA-5 C18 150*25 mm*5 μm; Mobile Phase A: water (0.05% HCl v/v); Mobile phase B: MeCN; Gradient: B from 6% to 36% in 10 min then hold at 100% for 3 min; Flow Rate (ml/min): 25; Column temperature: 35° C. and Wavelength: 220 nm 254 nm.

Preparative HPLC (Method H): Instrument: Gilson GX-281, Gilson 322 Pump, Gilson 156 UV Detector; Column: Phenomenex Gemini C18 250*50*10 μm; Mobile Phase A: water (10 mM $NH_4HCO_3$); Mobile phase B: MeCN; Gradient: B from 10% to 40% in 11.2 min holds at 100% for 2.5 min; FlowRate (ml/min): 22; Column temperature: 40° C. and Wavelength: 220 nm 254 nm Preparative HPLC (Method I): Instrument: Gilson GX-281 Liquid Handler, Gilson 322 Pump, Gilson 156 UV Detector; Column: Agela Durashell C18 150 mm×25 mm×5 μm; Mobile Phase A: water (0.225% FA, v/v); Mobile phase B: MeCN; Gradient: B from 32% to 62% in 10 min, hold 100% B for 2 min; Flow Rate (ml/min): 25; Column temperature: 40° C. and Wavelength: 220 nm 254 nm Preparative HPLC (Method J): Instrument: Gilson GX-281, Gilson 322 Pump, Gilson 156 UV Detector; Column: Waters Xbridge 150*25*5 μm; Mobile Phase A: water (10 mM $NH_4HCO_3$); Mobile phase B: MeCN; Gradient: B from 40% to 66% in 8.4 min then hold at 100% for 2 min; FlowRate (ml/min): 25; Column temperature: 30° C. and Wavelength: 220 nm 254 nm.

Preparative HPLC (Method K): Instrument: Gilson GX-281 Liquid Handler, Gilson 322 Pump, Gilson 156 UV Detector; Column: Agela ASB 150*25 mm*5 μm; Mobile Phase A: water (0.05% HCl); Mobile phase B: MeCN; Gradient: B from 0% to 25% in 8 min then hold at 100% for 0 min; Flow Rate (ml/min): 25; Column temperature: 40° C. and Wavelength: 220 nm 254 nm.

Preparative HPLC (Method L): Instrument: Gilson GX-281 Liquid Handler, Gilson 322 Pump, Gilson 156 UV Detector; Column: Agela ASB 150*25 mm*5 μm; Mobile Phase A: water (0.05% HCl); Mobile phase B: MeCN; Gradient: B from 0% to 25% in 8 min then hold at 100% for 0 min; Flow Rate (ml/min): 25; Column temperature: 40° C. and Wavelength: 220 nm 254 nm.

Preparative HPLC (Method M): Instrument: Gilson GX-281 Liquid Handler, Gilson 322 Pump, Gilson 156 UV Detector; Column: Agela Durashell C18 150 mm×25 mm×5 μm; Mobile Phase A: water (0.225% FA, v/v); Mobile phase B: MeCN; Gradient: B from 40% to 70% in 10 min, hold 100% B for 0 min; Flow Rate (ml/min): 25; Column temperature: 40° C. and Wavelength: 220 nm 254 nm.

$^1$H NMR spectra were recorded at 300, 400, 500 or 600 MHz on Bruker Avance instruments. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Abbreviations are in accordance with to the ACS Style Guide: "The ACS Style guide—A manual for authors and editors" Janet S. Dodd, Ed. 1997, ISBN: 0841234620 c. Preparation of the Intermediates

Intermediate 1

(R)-3-(Benzyloxy)-2-(((benzyloxy)carbonyl)amino)-3-oxopropan-1-aminium chloride

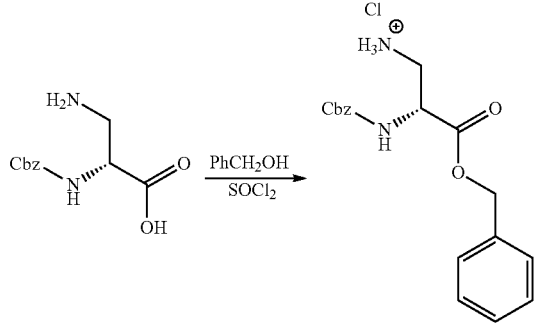

To phenylmethanol (56.0 mL) was added thionyl chloride (2.1 g, 17.6 mmol) dropwise at 28° C. After completion of the addition, (R)-3-amino-2-(((benzyloxy)carbonyl)amino) propanoic acid (3.8 g, 15.9 mmol) was added in several portions and the reaction was stirred for 24 hours at 28° C. The excess benzyl alcohol was removed at 80° C./0.02 bar and the residue was stirred in cyclohexane (35 mL) for 16 hours. Filtration and trituration of the filter cake with MTBE (50 mL) afforded the title compound (3.0 g).

LCMS (MH+): (m/z)=329.2, $t_R$ (min, Method AA)=0.52.

Intermediate 2

Lithium 7-chlorothieno[3,2-b]pyridine-2-carboxylate

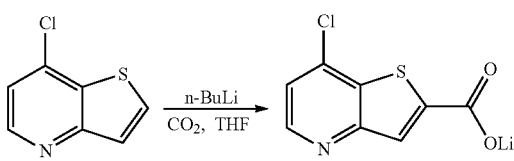

To a solution of 7-chlorothieno[3,2-b]pyridine (10.0 g, 58.9 mmol) in THF (150 mL) was added drop wise n-butyl lithium (n-BuLi) (2.5 M in hexane, 23.6 mL) at −78° C. The mixture was stirred at −78° C. for 30 minutes. Then gaseous carbon dioxide (15 psi) was bubbled through the reaction solution and the mixture was allowed to warm to 20° C. over a period of 16 hours. The mixture was diluted with THF (20 mL) and filtered. The filtered cake was collected and dried to give lithium 7-chlorothieno[3,2-b]pyridine-2-carboxylate (12 g).

d. Preparation of Exemplified Compounds of the Invention

Compound 1a (R)-2-amino-3-[[7-thieno[3,2-b]pyridine-2-carbonyl] amino]propanoic acid The overall synthesis scheme for the preparation of (R)-2-amino-3-[[7-thieno[3,2-b]pyridine-2-carbonyl]amino]propanoic acid is shown below.

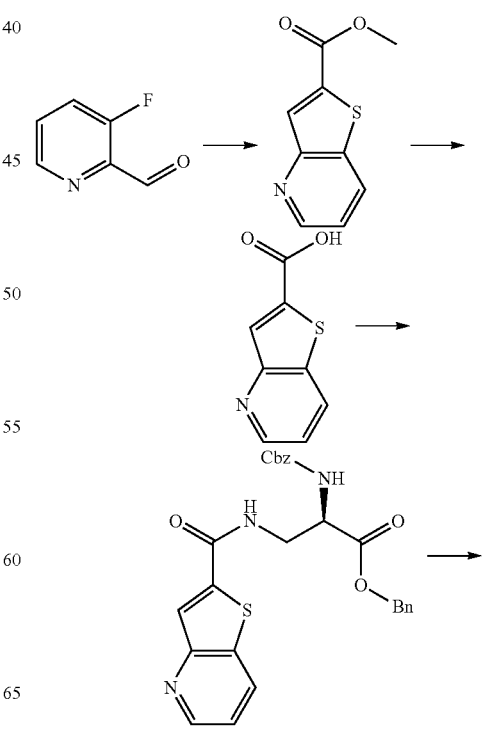

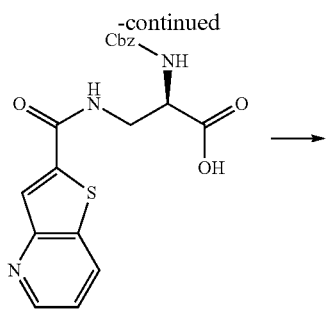

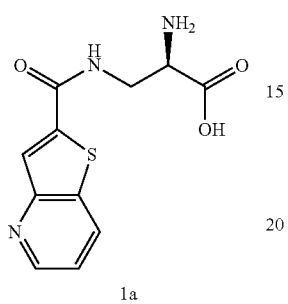

1a

Step 1: methyl thieno[3,2-b]pyridine-2-carboxylate

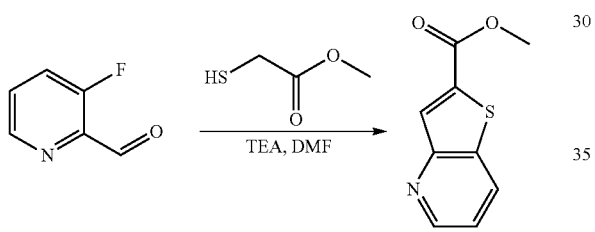

To a mixture of 3-fluoropicolinaldehyde (500 mg, 4.0 mmol) and methyl 2-mercaptoacetate (830 mg, 7.82 mmol, 0.7 mL) in dimethylformamide (DMF) (10 mL) was added triethylamine (TEA) (1.1 mL) at 20° C. The mixture was stirred at 100° C. for 4 hours. The mixture was diluted with H$_2$O (30 mL) and extracted with ethyl acetate (10 mL×3). The organic phase was washed with brine (10 mL×2), dried over Na$_2$SO$_4$ and concentrated. The residue was purified by CombiFlash (Petroleum ether: Ethyl acetate=0~30%) to give methyl thieno[3,2-b]pyridine-2-carboxylate (620 mg).

$^1$H NMR (400 MHz, CDCl$_3$) δ 8.77 (dd, J=4.50, 1.37 Hz, 1H), 8.22 (d, J=0.78 Hz, 1H), 8.19-8.21 (m, 1H), 7.35 (dd, J=8.22, 4.50 Hz, 1H), 3.98 (s, 3H).

Step 2: thieno[3,2-b]pyridine-2-carboxylic acid

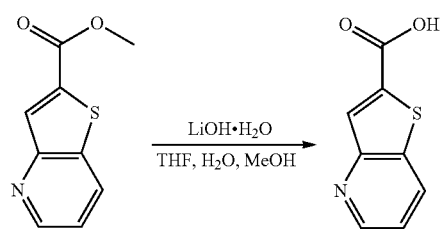

A mixture of methyl thieno[3,2-b]pyridine-2-carboxylate (200 mg, 1.04 mmol) and LiOHxH$_2$O (87 mg, 2.1 mmol) in MeOH (2 mL), tetrahydrofuran (THF) (2 mL) and H$_2$O (2 mL) was stirred at 25° C. for 16 h. The mixture was extracted with tert-butyl methyl ether (MTBE) (5 mL×2). The aqueous phase was adjusted to pH=3~4 with HCl (2M, 1 mL). The precipitate was filtered. The filter cake was dried to give thieno[3,2-b]pyridine-2-carboxylic acid (160 mg).

$^1$H NMR (400 MHz, DMSO-d$_6$) δ 8.77 (dd, J=4.27, 1.25 Hz, 1H), 8.56 (d, J=8.28 Hz, 1H), 8.11 (s, 1H), 7.51 (dd, J=8.28, 4.52 Hz, 1H).

Step 3: benzyl (R)-2-(((benzyloxy)carbonyl)amino)-3-(thieno[3,2-b]pyridine-2-carboxamido)propanoate A mixture of thieno[3,2-b]pyridine-2-carboxylic acid (160 mg, 0.9 mmol), (R)-benzyl 3-amino-2-(((benzyloxy)carbonyl)amino)propanoate (326 mg, HCl salt), O-(Benzotriazol-1-yl)-N,N,N',N'-tetramethyluronium tetrafluoroborate (430 mg) and N,N-diisopropylethylamine (0.8 mL) in DMF (5 mL) was stirred at 25° C. for 15 h. The mixture was diluted with H$_2$O (30 mL) and extracted with ethyl acetate (10 mL×3). The organic phase was washed with brine (10 mL×2), dried over Na$_2$SO$_4$ and concentrated. The residue was purified by CombiFlash (Petroleum ether: Ethyl acetate=0~80%) to give benzyl (R)-2-(((benzyloxy)carbonyl)amino)-3-(thieno[3,2-b]pyridine-2-carboxamido)propanoate (300 mg).

$^1$H NMR (400 MHz, CDCl$_3$) δ 8.73 (dd, J=4.41, 1.32 Hz, 1H), 8.17 (d, J=8.16 Hz, 1H), 8.03-8.03 (m, 1H), 7.82 (s, 1H), 7.23-7.36 (m, 12H), 6.03-6.05 (m, 1H), 5.20 (s, 2H), 5.11 (s, 2H), 4.62-4.63 (m, 1H), 3.80-4.00 (m, 2H).

Step 4: (R)-2-(((benzyloxy)carbonyl)amino)-3-(thieno[3,2-b]pyridine-2-carboxamido)propanoic acid

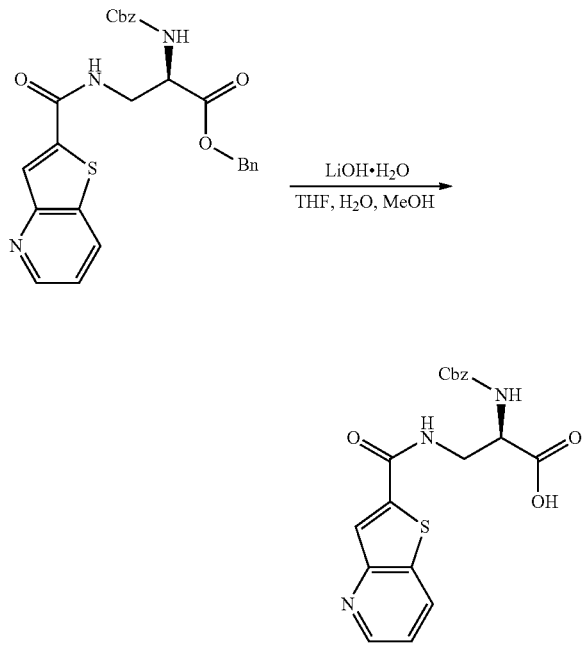

A mixture of compound benzyl (R)-2-(((benzyloxy)carbonyl)amino)-3-(thieno[3,2-b]pyridine-2-carboxamido)propanoate (100 mg, 204.27 mmol) and LiOHxH₂O (17 mg) in THF (2 mL), H₂O (2 mL) and MeOH (2 mL) was stirred at 25° C. for 15 h. The mixture was extracted with MTBE (5 mL×2). The aqueous phase was adjusted to pH=3~4 with HCl (2M, 1.5 mL). The precipitate was filtered. The filter cake was dried to give (R)-2-(((benzyloxy)carbonyl)amino)-3-(thieno[3,2-b]pyridine-2-carboxamido)propanoic acid (45 mg).

$^1$H NMR (400 MHz, DMSO-d₆) δ 9.01-9.04 (m, 1H), 8.74 (dd, J=4.52, 1.51 Hz, 1H), 8.53 (d, J=7.53 Hz, 1H), 8.22 (s, 1H), 7.6-7.62 (m, 1H), 7.46 (dd, J=8.28, 4.52 Hz, 1H), 7.23-7.38 (m, 5H), 4.97-5.10 (m, 2H), 4.24-4.35 (m, 1H), 3.51-3.75 (m, 2H).

Step 5: (R)-2-amino-3-[[7-thieno[3,2-b]pyridine-2-carbonyl]amino]propanoic acid

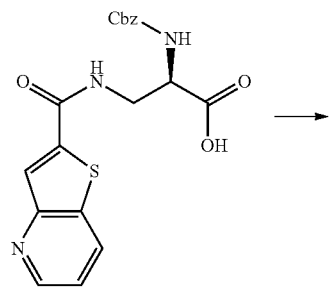

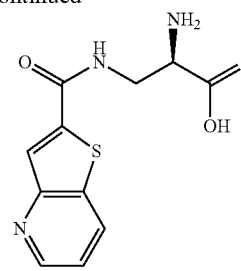

A mixture of compound (R)-2-(((benzyloxy)carbonyl)amino)-3-(thieno[3,2-b]pyridine-2-carboxamido)propanoic acid (40 mg, 0.10 mmol) and HBr (2 mL, 33% in acetic acid) were stirred at 25° C. for 1 h. The mixture was diluted with MTBE (3 mL) and decanted with MTBE (3 mL×3). The product was lyophilizated to give (R)-2-amino-3-(thieno[3,2-b]pyridine-2-carboxamido)propanoic acid as a salt with molecules of hydrobromic acid (28 mg).

$^1$H NMR (400 MHz, DMSO-d₆) δ 9.29-9.31 (m, 1H), 8.84 (d, J=4.52 Hz, 1H), 8.71-8.73 (m, 1H), 8.38-8.39 (m, 3H), 8.33 (s, 1H), 7.61 (dd, J=7.28, 4.77 Hz, 1H), 4.13-4.22 (m, 1H), 3.79-3.88 (m, 1H), 3.70-3.79 (m, 1H).

LCMS (MH+): m/z=266.1, $t_R$ (min, Method BB)=0.16.

$[α]^{20}D$=-20.0, (c=2.0 mg/mL, CH₃OH)

Compound 1b (R)-2-amino-3-[(7-ethylthieno[3,2-b]pyridine-2-carbonyl)amino]propanoic acid The overall synthesis scheme for the preparation of (R)-2-amino-3-[(7-ethylthieno[3,2-b]pyridine-2-carbonyl)amino]propanoic acid is shown below.

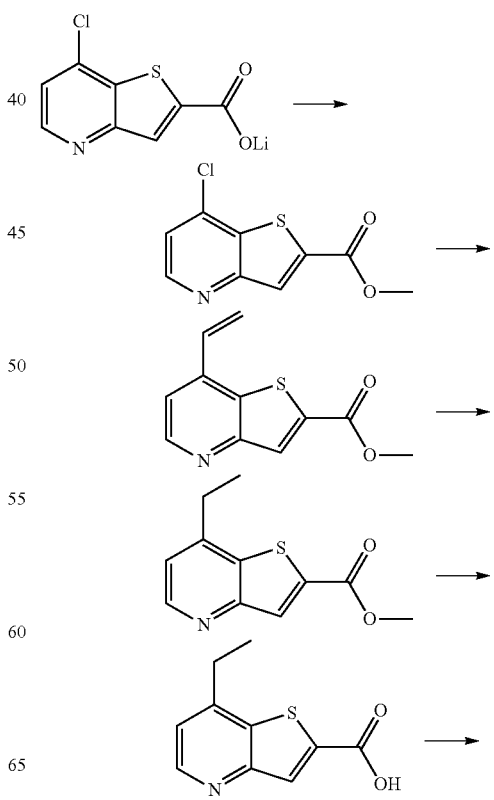

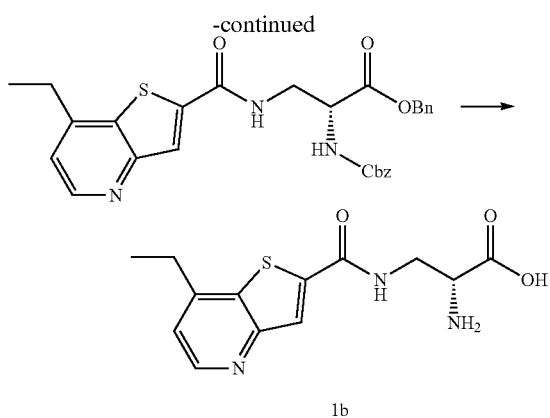

1b

Step 1: methyl 7-chlorothieno[3,2-b]pyridine-2-carboxylate

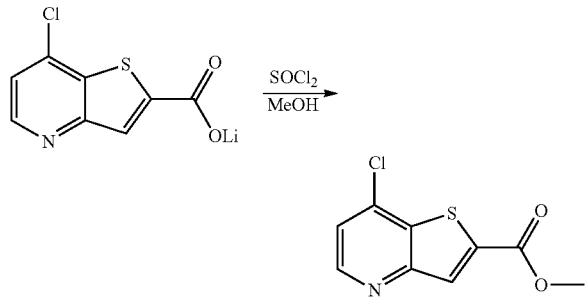

To a solution of lithium 7-chlorothieno[3,2-b]pyridine-2-carboxylate (0.5 g, 2.28 mmol) in MeOH (10 mL), SOCl₂ (813 mg, 6.83 mmol) was added. The reaction mixture was heated at 50° C. for 39 hours. The mixture was concentrated to give methyl 7-chlorothieno[3,2-b]pyridine-2-carboxylate (0.5 g, 75% yield) as a HCl salt.

LC-MS: $t_R$=0.844 min, m/z=227.9 [M+H]⁺.

Step 2: methyl 7-vinylthieno[3,2-b]pyridine-2-carboxylate

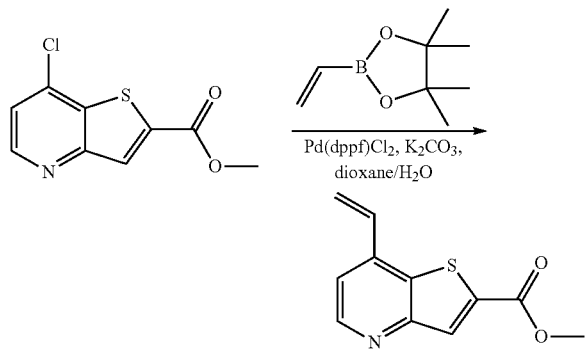

To a solution of methyl 7-chlorothieno[3,2-b]pyridine-2-carboxylate (1.2 g, 5.27 mmol) and 4,4,5,5-tetramethyl-2-vinyl-1,3,2-dioxaborolane (974 mg, 6.32 mmol) in dioxane (15 mL) and H₂O (1.5 mL) was added [1,1'-Bis(diphe- nylphosphino)ferrocene]dichloropalladium(II) (Pd(dppf)Cl₂) (386 mg, 0.53 mmol) and K₂CO₃ (2.19 g, 15.81 mmol) under nitrogen atmosphere. The mixture was stirred at 100° C. for 16 hours. The mixture was diluted with water (20 mL) and EtOAc (20 mL) and filtered. The filtrate was extracted with EtOAc (20 mL×3), and the combined organic layers were concentrated under reduced pressure. The residue was purified by Combi Flash (petroleum ether: EtOAc with EtOAc from 0 to 20%) to give methyl 7-vinylthieno[3,2-b]pyridine-2-carboxylate (920 mg).

¹H NMR (400 MHz, CDCl₃) δ 8.75 (d, 1H), 8.26 (s, 1H), 7.36 (d, 1H), 6.93 (dd, 1H), 6.22 (d, 1H), 5.79 (d, 1H), 4.00 (s, 3H).

Step 3: methyl 7-ethylthieno[3,2-b]pyridine-2-carboxylate

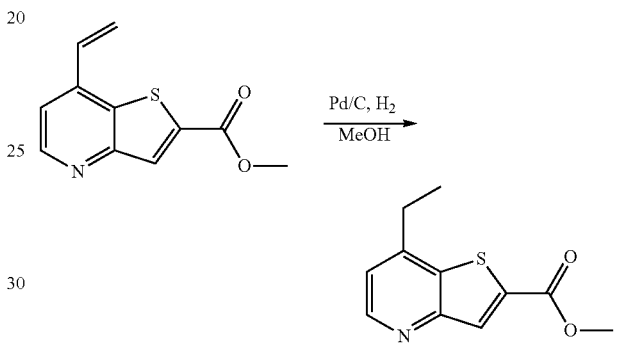

To a solution of methyl 7-vinylthieno[3,2-b]pyridine-2-carboxylate (0.17 g, 0.78 mmol) in MeOH (10 mL) was added Pd/C (30 mg, 10% Pd, 50% water) under N₂. The suspension was degassed under vacuum and purged with H₂ several times. The mixture was stirred under H₂ (balloon) at 10° C. for 3 hours. The reaction mixture was filtered and the filtrate was concentrated to give methyl 7-ethylthieno[3,2-b]pyridine-2-carboxylate (0.1 g).

¹H NMR (400 MHz, CDCl₃) δ 8.69 (d, J=4.4 Hz, 1H), 8.23 (s, 1H), 7.20 (d, J=4.8 Hz, 1H), 3.98 (s, 3H), 2.93 (q, J=7.6 Hz, 2H), 1.41 (t, J=7.6 Hz, 3H).

Step 4: 7-ethylthieno[3,2-b]pyridine-2-carboxylic acid

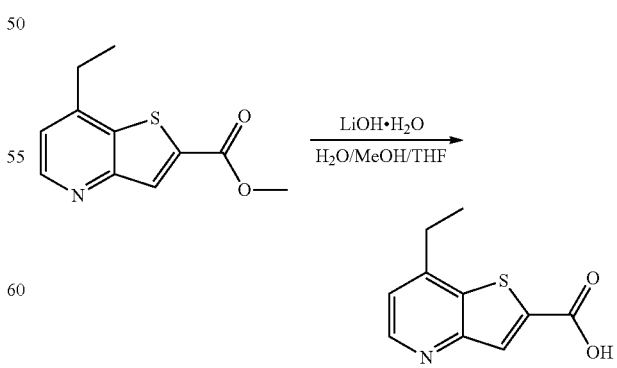

To a solution of methyl 7-ethylthieno[3,2-b]pyridine-2-carboxylate (0.1 g, 0.45 mmol) in a mixture of MeOH (4 mL), H₂O (2 mL) and THF (4 mL) was added LiOH×H₂O (38 mg, 0.90 mmol). The mixture was stirred at 10° C. for 16 hours. Aqueous HCl was used to adjust the pH to 3. The reaction mixture was concentrated to give 7-ethylthieno[3,2-b]pyridine-2-carboxylic acid (150 mg).

$^1$H NMR (400 MHz, CD$_3$OD) δ 8.94 (d, J=6.0 Hz, 1H), 8.28 (s, 1H), 7.90 (d, J=5.6 Hz, 1H), 3.23 (q, J=7.6 Hz, 2H), 1.49 (t, J=7.6 Hz, 3H).

Step 5: (R)-benzyl 2-(((benzyloxy)carbonyl)amino)-3-(7-ethylthieno[3,2-b]pyridine-2-carboxamido)propanoate

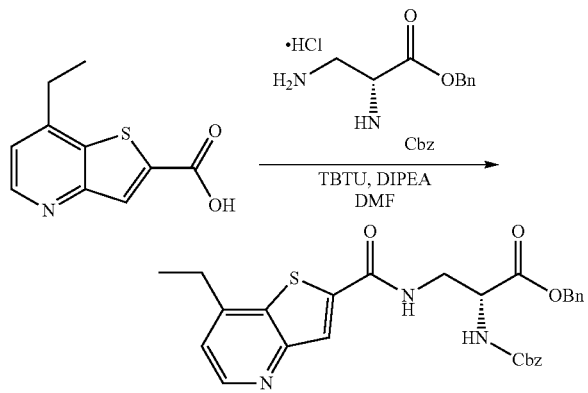

To a solution of 7-ethylthieno[3,2-b]pyridine-2-carboxylic acid (0.09 g) and (R)-benzyl 3-amino-2-(((benzyloxy)carbonyl)amino)propanoate (171 mg, 0.52 mmol, HCl salt) in DMF (10 mL) was added O-(Benzotriazol-1-yl)-N,N,N',N'-tetramethyluronium tetrafluoroborate (209 mg, 0.65 mmol) and N,N-diisopropylethylamine (169 mg, 1.30 mmol). The reaction mixture was stirred at 10° C. for 16 hours. The reaction mixture was quenched with water (20 mL), extracted with EtOAc (20 mL×3). The combined organic layers were washed with brine (20 mL×3), dried over Na$_2$SO$_4$ and concentrated. The residue was purified by column chromatography on silica gel (petroleum ether/EtOAc with EtOAc from 0% to 100%) to give (R)-benzyl 2-(((benzyloxy)carbonyl)amino)-3-(7-ethylthieno[3,2-b]pyridine-2-carboxamido)propanoate (70 mg).

LC-MS: $t_R$=0.911 min, m/z=518.1 [M+H]$^+$.

Step 6: (R)-2-amino-3-[(7-ethylthieno[3,2-b]pyridine-2-carbonyl)amino]propanoic acid

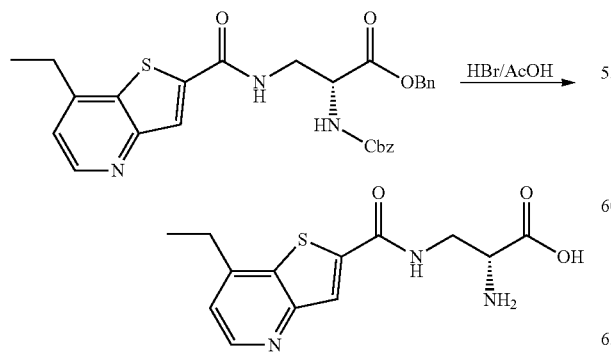

A solution of (R)-benzyl 2-(((benzyloxy)carbonyl)amino)-3-(7-ethylthieno[3,2-b]pyridine-2-carboxamido)propanoate (70 mg, 0.14 mmol) in 30% HBr in AcOH (2 mL) was heated at 50° C. for 16 hours. The reaction mixture was concentrated and added AcOH (2 mL). The light-yellow precipitate formed was collected by filtration, washed with AcOH (2 mL) and dried to give (R)-2-amino-3-(7-ethylthieno[3,2-b]pyridine-2-carboxamido)propanoic acid (23 mg) as the HBr salt.

$^1$H NMR (400 MHz, DMSO-d$_6$) δ 9.35 (t, J=5.6 Hz, 1H), 8.82 (d, J=4.8 Hz, 1H), 8.43-8.33 (m, 4H), 7.56 (d, J=4.8 Hz, 1H), 4.20-4.10 (m, 1H), 3.87-3.81 (m, 1H), 3.77-3.70 (m, 1H), 3.00 (q, J=7.6 Hz, 2H), 1.35 (t, J=7.6 Hz, 3H).

LCMS (MH+): m/z=294, $t_R$ (min, Method BB)=0.24. [α]$^{20}$D=−2.0 (c=1.0 mg/mL, CH$_3$OH).

Compound 1c (R)-2-amino-3-[[7-(difluoromethyl)thieno[3,2-b]pyridine-2-carbonyl]amino]propanoic acid The overall synthesis scheme for the preparation of (R)-2-amino-3-[[7-(difluoromethyl)thieno[3,2-b]pyridine-2-carbonyl]amino]propanoic acid is shown below.

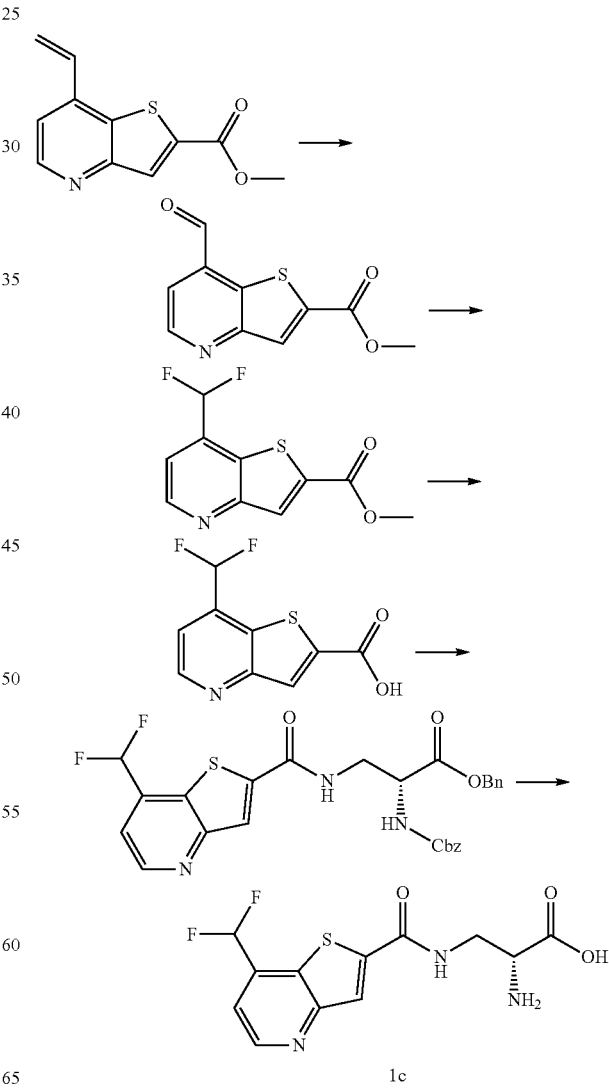

1c

Step 1: Methyl 7-formylthieno[3,2-b]pyridine-2-carboxylate

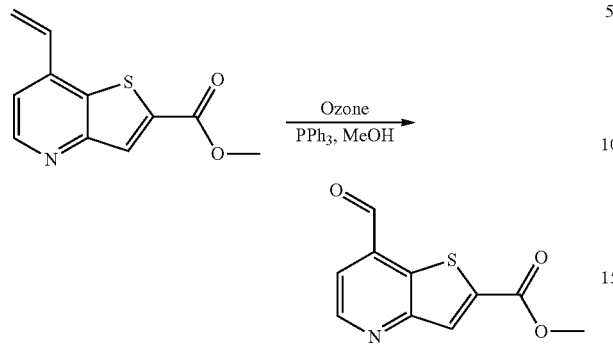

Ozone was bubbled to a solution of methyl 7-vinylthieno [3,2-b]pyridine-2-carboxylate (700 mg, 3.19 mmol) in MeOH (30 mL) at −78° C. for 10 min, then the mixture was warmed to 25° C. PPh₃ (1.26 g, 4.79 mmol) was added, and the mixture was stirred at 25° C. for 2 hours. The mixture was concentrated under reduced pressure. The residue was purified by CombiFlash (petroleum ether: EtOAc with EtOAc from 0 to 30%) to give methyl 7-formylthieno[3,2-b]pyridine-2-carboxylate (550 mg).

$^1$H NMR (400 MHz, CDCl$_3$) δ 10.35 (s, 1H), 9.10 (d, J=4.4 Hz, 1H), 8.33 (s, 1H), 7.82 (d, J=4.4 Hz, 1H), 4.02 (s, 3H).

Step 2: Methyl 7-(difluoromethyl)thieno[3,2-b]pyridine-2-carboxylate

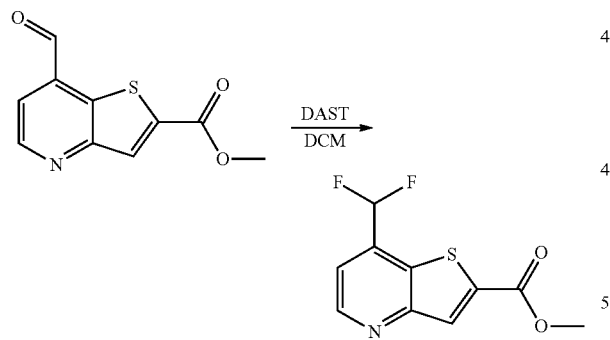

To a solution of methyl 7-formylthieno[3,2-b]pyridine-2-carboxylate (550 mg, 2.49 mmol) in dichloromethane (DCM) (15 mL) was added (diethylamino)sulfur trifluoride (DAST) (602 mg, 3.74 mmol) at 0° C. The mixture was stirred at 25° C. for 2 hours. The mixture was quenched with water (0.5 mL) and concentrated under reduced pressure.

The residue was purified by CombiFlash (petroleum ether: EtOAc with EtOAc from 0 to 30%) to give methyl 7-(difluoromethyl)thieno[3,2-b]pyridine-2-carboxylate (350 mg).

$^1$H NMR (400 MHz, CDCl$_3$) δ 8.89 (d, J=4.4 Hz, 1H), 8.30 (s, 1H), 7.48 (d, J=4.4 Hz, 1H), 7.17-6.73 (t, 1H), 4.01 (s, 3H).

Step 3: 7-(difluoromethyl)thieno[3,2-b]pyridine-2-carboxylic acid

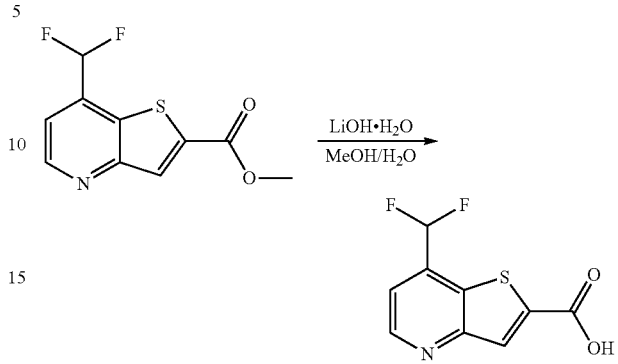

To a solution of methyl 7-(difluoromethyl)thieno[3,2-b] pyridine-2-carboxylate (440 mg, 1.81 mmol) in MeOH (10 mL) was added LiOH.H₂O (228 mg, 5.43 mmol) dissolved in water (1 mL). The mixture was stirred at 25° C. for 3 hours. The mixture was concentrated under reduced pressure. The residue was dissolved in water (10 mL) and washed with EtOAc (10 mL), the organic layer was discarded. The aqueous layer was acidified by 2N HCl (2 mL) and the precipitate was collected to give 7-(difluoromethyl) thieno[3,2-b]pyridine-2-carboxylic acid (320 mg).

$^1$H NMR (400 MHz, DMSO-d$_6$) δ 8.94 (d, J=4.4 Hz, 1H), 8.22 (s, 1H), 7.73 (d, J=4.4 Hz, 1H), 7.63-7.32 (m, 1H).

Step 4: (R)-Benzyl 2-(((benzyloxy)carbonyl) amino)-3-(7-(difluoromethyl)thieno [3,2-b]pyridine-2-carboxamido)propanoate

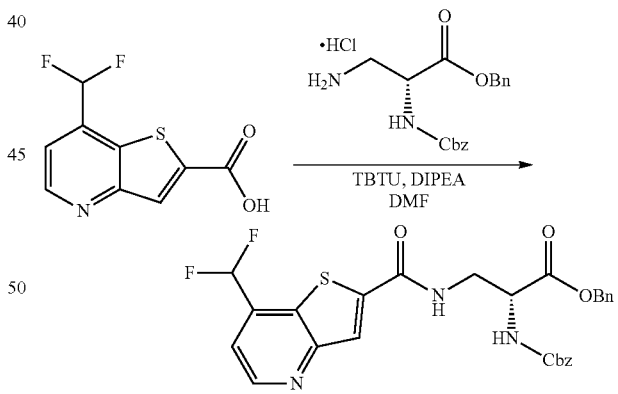

To a solution of 7-(difluoromethyl)thieno[3,2-b]pyridine-2-carboxylic acid (320 mg, 1.40 mmol) and (R)-benzyl 3-amino-2-(((benzyloxy)carbonyl)amino)propanoate (511 mg, 1.40 mmol, HCl salt) in DMF (8 mL) was added O-(Benzotriazol-1-yl)-N,N,N',N'-tetramethyluronium tetrafluoroborate (674 mg, 2.10 mmol) and N,N-diisopropylethylamine (543 mg, 4.20 mmol). The mixture was stirred at 25° C. for 16 hours. The mixture was diluted with water (10 mL) and extracted with EtOAc (10 mL×3). The combined organic layers were washed with water (20 mL) and brine (20 mL) and concentrated under reduced pressure. The residue was purified by Combi Flash (petroleum ether:

EtOAc with EtOAc from 0 to 60%) to give (R)-benzyl 2-(((benzyloxy)carbonyl)amino)-3-(7-(difluoromethyl) thieno[3,2-b] pyridine-2-carboxamido)propanoate (600 mg).

¹H NMR (400 MHz, CDCl₃) δ 8.85 (d, J=4.4 Hz, 1H), 7.90 (s, 1H), 7.46 (d, J=4.4 Hz, 1H), 7.39-7.27 (m, 10H), 6.91 (t, 1H), 6.05 (br d, 1H), 5.22 (s, 2H), 5.12 (s, 2H), 4.68-4.59 (m, 1H), 4.01-3.92 (m, 1H), 3.91-3.82 (m, 1H).

Step 5: Preparation of (R)-2-amino-3-[[7-(difluoromethyl)thieno[3,2-b]pyridine-2-carbonyl]amino] propanoic acid

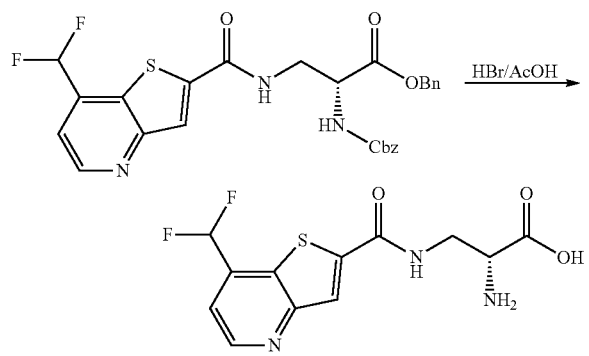

A mixture of (R)-benzyl 2-(((benzyloxy)carbonyl) amino)-3-(7-(difluoromethyl)thieno [3,2-b]pyridine-2-carboxamido)propanoate (200 mg, 0.37 mmol) in 33% HBr in AcOH (4 mL) was stirred at 50° C. for 16 hours. The mixture was concentrated under reduced pressure. The residue was purified by preparative HPLC (Method A) to give (R)-2-amino-3-(7-(difluoromethyl)thieno[3,2-b]pyridine-2-carboxamido)propanoic acid (86 mg) as HCl salt.

¹H NMR (400 MHz, DMSO-d₆) δ 9.58 (br t, J=6.0 Hz, 1H), 8.91 (d, J=4.8 Hz, 1H), 8.66-8.58 (m, 3H), 8.55 (s, 1H), 7.69 (d, J=4.8 Hz, 1H), 7.47 (t, 1H), 4.22-4.12 (m, 1H), 3.94-3.76 (m, 2H).

LCMS (MH+): m/z=316.2, t_R (min, Method BB)=0.29, [α]²⁰_D=-6.5, (c=2 mg/mL, DMSO).

Compound 1d (R)-2-amino-3-[(7-cyclopropylthieno[3,2-b]pyridine-2-carbonyl)amino]propanoic acid The overall synthesis scheme for the preparation of (R)-2-amino-3-[(7-cyclopropylthieno[3,2-b]pyridine-2-carbonyl)amino]propanoic acid is shown below.

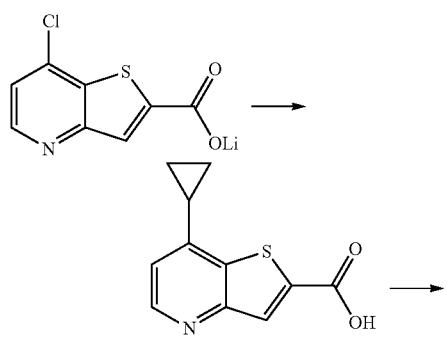

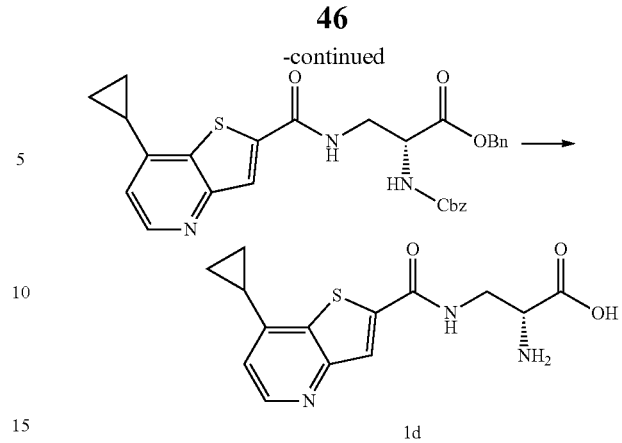

Step 1: 7-cyclopropylthieno[3,2-b]pyridine-2-carboxylic acid

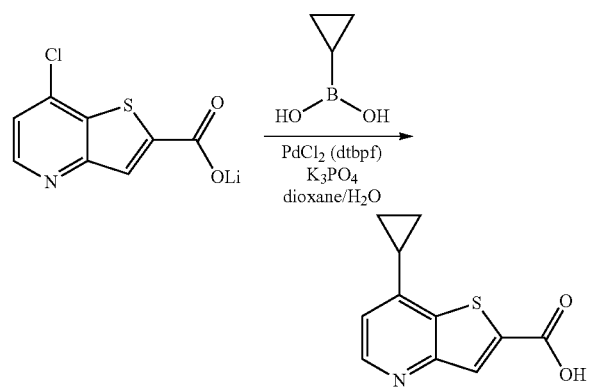

A mixture of lithium 7-chlorothieno[3,2-b]pyridine-2-carboxylate (500 mg, 2.46 mmol), cyclopropylboronic acid (423 mg, 4.92 mmol) and K₃PO₄ (1.04 g, 4.92 mmol) in dioxane (10 mL) and H₂O (2 mL) was stirred under N₂ condition. Then PdCl₂(dtbpf) (80 mg, 0.123 mmol) was added and the mixture stirred at 110° C. for 16 hours. The mixture was poured into water (15 mL), extracted with ethyl acetate (20 mL). The organic phase was discarded, the water phase was adjusted pH (4~5) by HCl aq (3M) and concentrated to afford 7-cyclopropylthieno[3,2-b]pyridine-2-carboxylic acid (700 mg).

Step 2: Benzyl (R)-2-(((benzyloxy)carbonyl) amino)-3-(7-cyclopropylthieno [3,2-b]pyridine-2-carboxamido)propanoate

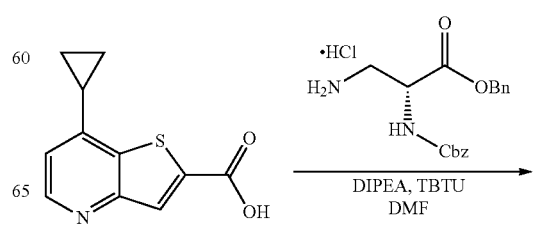

-continued

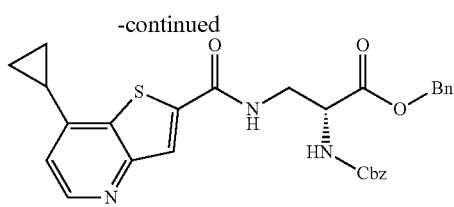

A mixture of 7-cyclopropylthieno[3,2-b]pyridine-2-carboxylic acid (650 mg, 2.89 mmol), benzyl (R)-3-amino-2-(((benzyloxy)carbonyl)amino)propanoate (1.05 g, 2.89 mmol, HCl salt), N,N-diisopropylethylamine (1.12 g, 8.67 mmol) and O-(Benzotriazol-1-yl)-N,N,N',N'-tetramethyluronium tetrafluoroborate (1.39 g, 4.34 mmol) in DMF (5 mL) was stirred at 30° C. for 16 hours. The mixture was poured into water (20 mL) and extracted with ethyl acetate (20 mL×2). The combined organic phases were washed by brine (30 mL×3), dried over $Na_2SO_4$ and concentrated. The residue was purified by combiFlash (Ethyl acetate: Petroleum ether=0~50%) to give benzyl (R)-2-(((benzyloxy)carbonyl)amino)-3-(7-cyclopropylthieno[3,2-b]pyridine-2-carboxamido)propanoate (260 mg).

$^1$H NMR (400 MHz, DMSO-$d_6$) δ 9.05 (br, 1H), 8.60 (d, 1H), 8.18 (s, 1H), 7.89 (br d, 1H), 7.36-7.22 (m, 10H), 7.04 (d, J=5.2 Hz, 1H), 5.11 (d, J=5.2 Hz, 2H), 5.06 (m, 2H), 4.47-4.42 (m, 1H), 3.77-3.65 (m, 2H), 2.10-2.18 (m, 1H), 1.24-1.17 (m, 2H), 1.05-0.96 (m, 2H).

Step 3: (R)-2-amino-3-[(7-cyclopropylthieno[3,2-b]pyridine-2-carbonyl)amino]propanoic acid

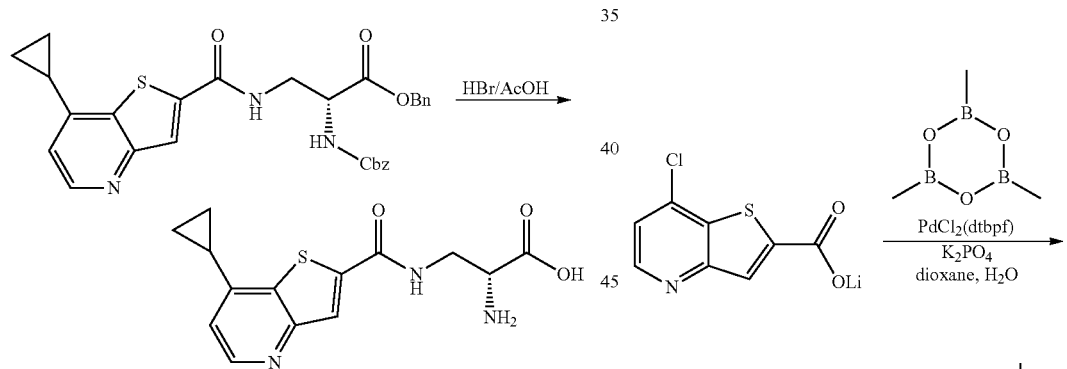

A mixture of benzyl (R)-2-(((benzyloxy)carbonyl)amino)-3-(7-cyclopropylthieno [3,2-b]pyridine-2-carboxamido)propanoate (80.0 mg, 0.15 mmol) in HBr/AcOH (3 mL, 33%) was stirred at 50° C. for 16 hours. The mixture was concentrated on vacuo. The residue was purified by preparative-HPLC (Method B) to give (R)-2-amino-3-(7-cyclopropylthieno [3,2-b]pyridine-2-carboxamido)propanoic acid (15 mg) as HCl salt.

$^1$H NMR (400 MHz, $D_2O$) δ 8.59-8.52 (m, 1H), 8.09-8.02 (m, 1H), 7.24-7.14 (m, 1H), 4.21-4.12 (m, 1H), 3.95 (dd, 1H), 3.85 (dd, 1H), 2.26 (m, 1H), 1.45 (dd, 2H), 1.24-1.14 (m, 2H).

LCMS (MH+): m/z=306.2, tR (min, Method BB)=0.22. $[α]^{20}D$=12.0 (c=0.25 mg/mL, $CH_3OH$).

Compound 1e (R)-2-amino-3-[(7-methylthieno[3,2-b]pyridine-2-carbonyl)amino]propanoic acid The overall synthesis scheme for the preparation of (R)-2-amino-3-[(7-methylthieno[3,2-b]pyridine-2-carbonyl)amino]propanoic acid is shown below.

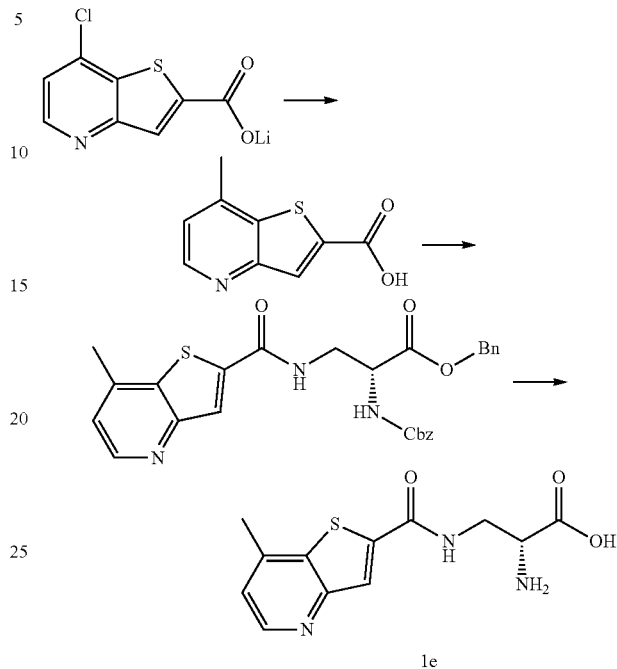

Step 1: 7-Methylthieno[3,2-b]pyridine-2-carboxylic acid

A mixture of lithium 7-chlorothieno[3,2-b]pyridine-2-carboxylate (300 mg, 1.37 mmol), 2,4,6-trimethyl-1,3,5,2,4,6-trioxatriborinane (344 mg, 2.74 mmol, 0.4 mL), $PdCl_2$(dtbpf) (90 mg, 0.14 mmol) and $K_3PO_4$ (727 mg, 3.43 mmol) in $H_2O$ (4 mL) and dioxane (12 mL) in sealed tube was heated to 80° C. for 16 hours under $N_2$. The mixture was filtered. The aqueous phase was adjusted to pH=3~4 with HCl (2M, 4 mL). The mixture was concentrated to give 7-methylthieno[3,2-b]pyridine-2-carboxylic acid (260 mg). The crude product was used for next step without any further purification.

Step 2: (R)-Benzyl 2-(((benzyloxy)carbonyl)amino)-3-(7-methylthieno[3,2-b]pyridine-2-carboxamido)propanoate

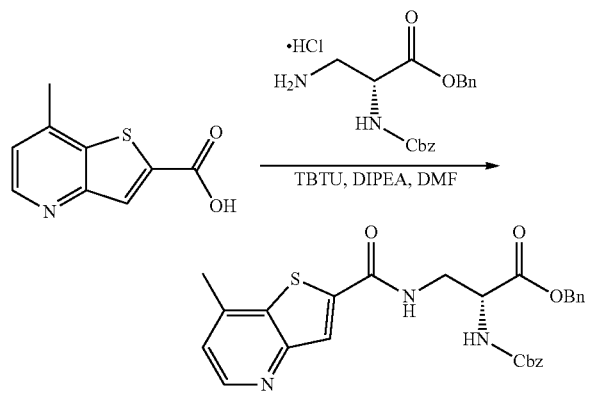

A mixture of 7-methylthieno[3,2-b]pyridine-2-carboxylic acid (260 mg, 1.35 mmol), (R)-benzyl 3-amino-2-(((benzyloxy)carbonyl)amino)propanoate (491 mg, 1.35 mmol, HCl salt), O-(benzotriazol-1-yl)-N,N,N',N'-tetramethyluronium tetrafluoroborate (648 mg, 2.02 mmol) and N,N-diisopropylethylamine (870 mg, 6.73 mmol, 1 mL) in DMF (10 mL) was stirred at 25° C. for 16 hours. The mixture was diluted with H₂O (30 mL) and extracted with ethyl acetate (10 mL×3). The organic phase was washed with brine (10 mL×2), dried over Na₂SO₄ and concentrated. The residue was purified by Preparative-HPLC (Method C) to give (R)-benzyl 2-(((benzyloxy)carbonyl)amino)-3-(7-methylthieno[3,2-b]pyridine-2-carboxamido)propanoate (280 mg).

¹H NMR (400 MHz, CDCl₃) δ 8.61 (d, 1H), 7.84 (s, 1H), 7.39-7.25 (m, 11H), 7.13 (d, 1H), 6.11 (m, 1H), 5.20 (s, 2H), 5.10 (s, 2H), 4.69-4.56 (m, 1H), 4.01-3.80 (m, 2H), 2.58 (s, 3H).

Step 3: (R)-2-amino-3-[(7-methylthieno[3,2-b]pyridine-2-carbonyl)amino]propanoic acid

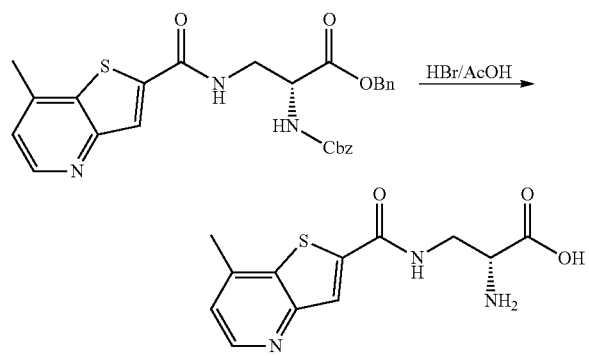

A mixture of (R)-benzyl 2-(((benzyloxy)carbonyl)amino)-3-(7-methylthieno[3,2-b]pyridine-2-carboxamido)propanoate (100 mg, 0.20 mmol) and HBr/AcOH (3 mL, 33%) was stirred at 50° C. for 16 hours. The mixture was diluted with MTBE (3 mL) and H₂O (3 mL). The aqueous phase was extracted with MTBE (3 mL×2). The aqueous phase was lyophilizated lyophilized to give (R)-2-amino-3-(7-methylthieno[3,2-b]pyridine-2-carboxamido)propanoic acid (50 mg) as HBr salt.

¹H NMR (400 MHz, DMSO-d₆) δ 9.42 (br s, 1H), 8.91-8.80 (m, 1H), 8.54-8.32 (m, 4H), 7.61 (br s, 1H), 4.20-4.10 (m, 1H), 3.90-3.69 (m, 2H), 2.71 (s, 3H).

LCMS (MH+): m/z=280.1, t$_R$ (min, Method BB)=0.17.

[α]²⁰D=−11.0, (c=1.0 mg/mL, CH₃OH).

Compound 1f (R)-2-amino-3-[(7-isopropylthieno[3,2-b]pyridine-2-carbonyl)amino]propanoic acid The overall synthesis scheme for the preparation of (R)-2-amino-3-[(7-isopropylthieno[3,2-b]pyridine-2-carbonyl)amino]propanoic acid is shown below.

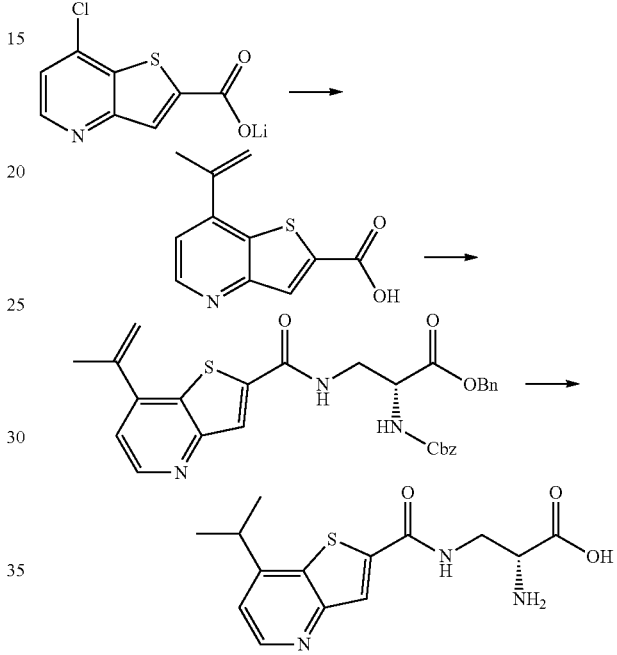

Step 1: 7-(prop-1-en-2-yl)thieno[3,2-b]pyridine-2-carboxylic acid

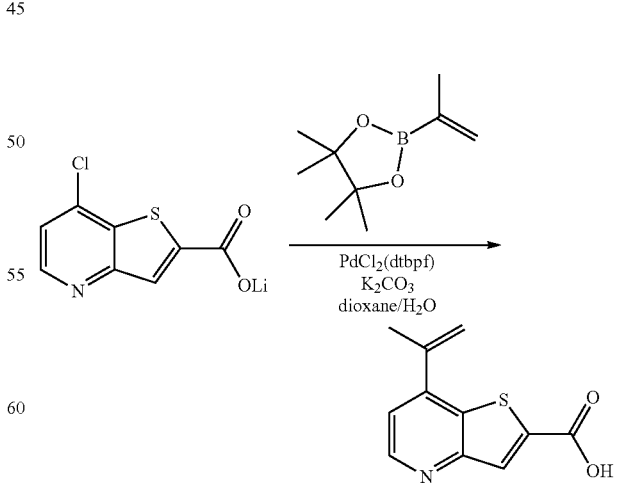

A mixture of lithium 7-chlorothieno[3,2-b]pyridine-2-carboxylate (300 mg, 1.37 mmol), 4,4,5,5-tetramethyl-2-(prop-1-en-2-yl)-1,3,2-dioxaborolane (230 mg, 1.37 mmol), PdCl₂(dtbpf) (10 mg, 0.01 mmol) and K₂CO₃ (189 mg, 1.37 mmol) in dioxane (25 mL) and H₂O (5 mL) was stirred at 100° C. for 16 hours. The mixture was poured into water (20 mL) and extracted with ethyl acetate (20 mL). The water phase was adjusted to pH (4~5) by HCl aq (3 M) and extracted with ethyl acetate (20 mL×3 times). The combined organic layers were washed by brine (20 mL×3), dried over anhydrous Na₂SO₄ and concentrated. The product 7-(prop-1-en-2-yl)thieno[3,2-b]pyridine-2-carboxylic acid (160 mg) was obtained and used in the next step without further purification.

¹H NMR (400 MHz, DMSO-d₆) δ8.75 (d, J=4.8 Hz, 1H), 8.09 (s, 1H), 7.46 (d, J=4.8 Hz, 1H), 5.71 (s, 1H), 5.63 (s, 1H), 2.23 (s, 3H).

Step 2: (R)-benzyl 2-(((benzyloxy)carbonyl)amino)-3-(7-(prop-1-en-2-yl)thieno [3,2-b]pyridine-2-carboxamido)propanoate

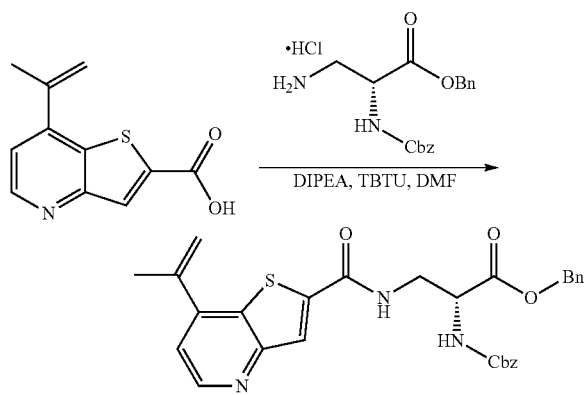

A mixture of 7-(prop-1-en-2-yl)thieno[3,2-b]pyridine-2-carboxylic acid (150 mg, 0.69 mmol), (R)-benzyl 3-amino-2-(((benzyloxy)carbonyl)amino)propanoate (225 mg, 0.62 mmol, HCl salt), N,N-diisopropylethylamine (442 mg, 3.42 mmol) and O-(benzotriazol-1-yl)-N,N,N',N'-tetramethyluronium tetrafluoroborate (329 mg, 1.03 mmol) in DMF (5 mL) was stirred at 30° C. for 16 hours. The mixture was poured into water (10 mL) and extracted with ethyl acetate (10 mL×3 times). The combined organic phases were washed by brine (10 mL×3 times), dried over Na₂SO₄ and concentrated. The residue was purified by preparative HPLC (Method D) to afford (R)-benzyl 2-(((benzyloxy)carbonyl)amino)-3-(7-(prop-1-en-2-yl) thieno[3,2-b]pyridine-2-carboxamido)propanoate (93 mg).

¹H NMR (400 MHz, CDCl₃) δ 8.72 (d, J=4.8 Hz, 1H), 7.82 (s, 1H), 7.41-7.25 (m, 11H), 5.73 (s, 1H), 5.57 (s, 1H), 5.22 (s, 2H), 5.13 (s, 2H), 4.70-4.60 (m, 1H), 4.00-3.80 (m, 2H), 2.27 (s, 3H).

Step 3: (R)-2-amino-3-[(7-isopropylthieno[3,2-b]pyridine-2-carbonyl)amino]propanoic acid

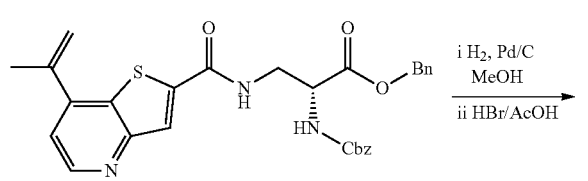

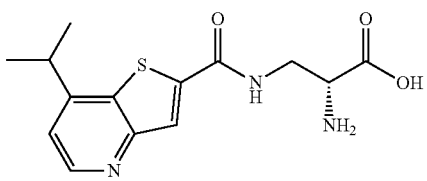

To a solution of (R)-benzyl 2-(((benzyloxy)carbonyl)amino)-3-(7-(prop-1-en-2-yl)thieno [3,2-b]pyridine-2-carboxamido)propanoate (90 mg, 0.170 mmol) in MeOH (10 mL) was added Pd/C (10% Pd, 50% water, 100 mg) under N₂. The suspension was degassed under vacuum and purged with H₂ several times. The mixture was stirred under H₂ (50 psi) at 25° C. for 16 hours, filtered and the filtrate was concentrated. The residue was transferred to HBr/AcOH (2 mL, 33%) and stirred at 50° C. for 16 hours. The mixture was concentrated. The residue was washed by MTBE (5 mL) and filtered to give (R)-2-amino-3-(7-isopropylthieno [3,2-b]pyridine-2-carboxamido)propanoic acid (25 mg) as HBr salt.

¹H NMR (400 MHz, DMSO-d₆) δ 9.26 (br, 1H), 8.77 (d, J=4.8 Hz, 1H), 8.44-8.35 (m, 2H), 8.31 (s, 1H), 7.49 (d, 1=4.8 Hz, 1H), 4.20-4.10 (m, 1H), 3.88-3.72 (m, 2H), 3.30-3.20 (m, 1H), 1.38 (d, J=6.8 Hz, 6H).

LCMS (MH+): m/z=308, $t_R$ (min, Method BB)=0.28, $[α]^{20}D$=−3.1 (c=0.96 mg/mL, CH₃OH).

Compound 1g (R)-2-amino-3-[[7-(2-ethylphenyl)thieno[3,2-b]pyridine-2-carbonyl]amino]propanoic acid The overall synthesis scheme for the preparation of (R)-2-amino-3-[[7-(2-ethylphenyl)thieno[3,2-b]pyridine-2-carbonyl]amino]propanoic acid is shown below.

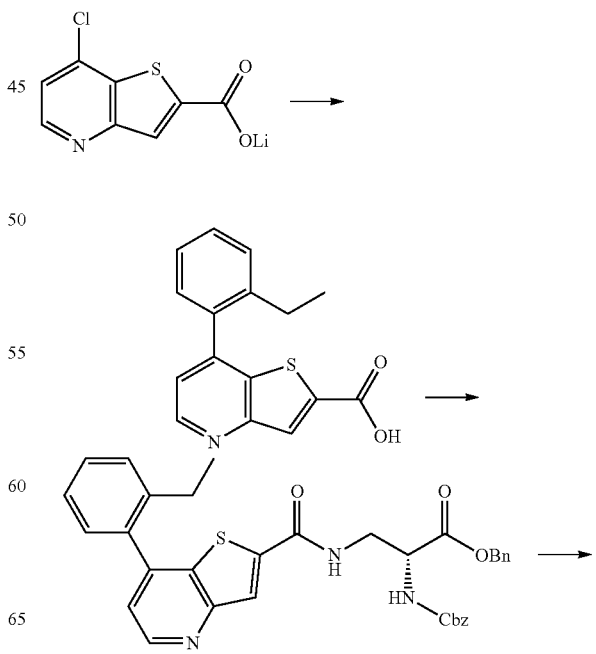

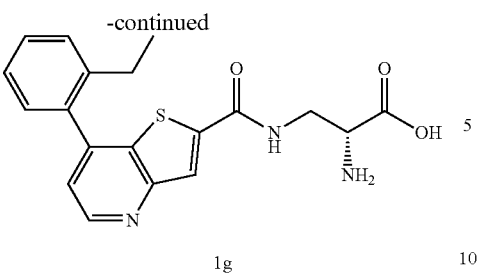

1g

Step 1: 7-(2-Ethylphenyl)thieno[3,2-b]pyridine-2-carboxylic acid

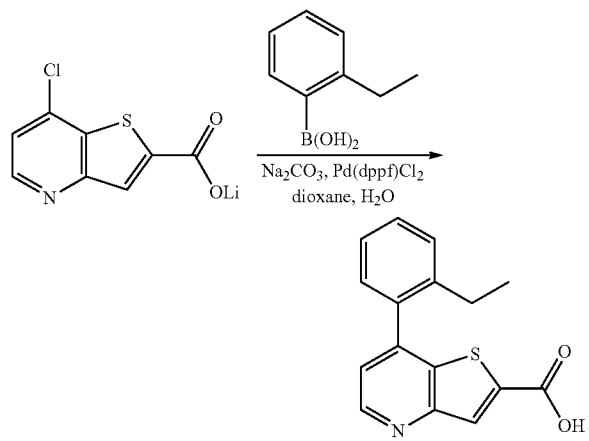

Lithium 7-chlorothieno[3,2-b]pyridine-2-carboxylate (1.0 g, 4.55 mmol), (2-ethylphenyl)boronic acid (1.16 g, 7.74 mmol), Na$_2$CO$_3$ (1.45 g, 13.6 mmol) and Pd(dppf)Cl$_2$ (333 mg, 0.46 mmol) in H$_2$O (10 mL) and dioxane (20 mL) was de-gassed and then heated to 110° C. for 16 hours under N$_2$. The mixture was concentrated, and the residue was diluted with H$_2$O (10 mL), and extracted with ethyl acetate (10 mL×2). The aqueous phase was adjusted to pH=3~4 with HCl (2M, 5 mL). The precipitate was filtered and dried to give 7-(2-ethylphenyl)thieno[3,2-b]pyridine-2-carboxylic acid (700 mg).

$^1$H NMR (400 MHz, DMSO-d$_6$) δ 8.86 (d, 1H), 8.18 (s, 1H), 7.51-7.47 (m, 2H), 7.45 (d, 1H), 7.40-7.36 (m, 1H), 7.35-7.32 (m, 1H), 2.45-2.43 (m, 2H), 0.97 (t, 3H)

Step 2: Benzyl (R)-2-(((benzyloxy)carbonyl)amino)-3-(7-(2-ethylphenyl)thieno[3,2-b]pyridine-2-carboxamido)propanoate

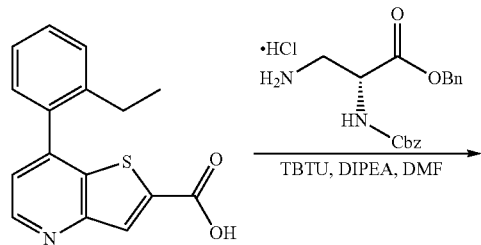

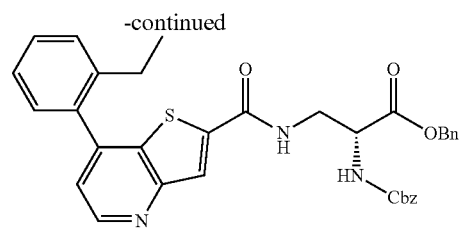

A mixture of 7-(2-ethylphenyl)thieno[3,2-b]pyridine-2-carboxylic acid (200 mg, 0.71 mmol), (R)-benzyl 3-amino-2-(((benzyloxy)carbonyl)amino)propanoate (258 mg, 0.71 mmol, HCl salt), O-(benzotriazol-1-yl)-N,N,N',N'-tetramethyluronium tetrafluoroborate (340 mg, 1.06 mmol) and N,N-diisopropylethylamine (456 mg, 3.53 mmol) in DMF (10 mL) was stirred at 25° C. for 16 hours. The mixture was diluted with H$_2$O (30 mL) and extracted with ethyl acetate (10 mL×3). The organic phase was washed with brine (10 mL×2), dried over Na$_2$SO$_4$ and concentrated. The residue was purified by preparative-HPLC (Method E) to give benzyl (R)-2-(benzyloxy)carbonyl)amino)-3-(7-(2-ethylphenyl)thieno[3,2-b]pyridine-2-carboxamido)propanoate (200 mg).

$^1$H NMR (400 MHz, CDCl$_3$) δ 8.78 (d, 1H), 7.89 (s, 1H), 7.47-7.38 (m, 2H), 7.36-7.25 (m, 12H), 7.22 (d, 1H), 7.08 (br s, 1H), 5.97 (br s, 1H), 5.19 (s, 2H), 5.10 (s, 2H), 4.60-4.59 (m, 1H), 3.98-3.78 (m, 2H), 2.55-2.42 (m, 2H), 1.04 (t, 3H).

Step 3: (R)-2-amino-3-[[7-(2-ethylphenyl)thieno[3,2-b]pyridine-2-carbonyl]amino]propanoic acid

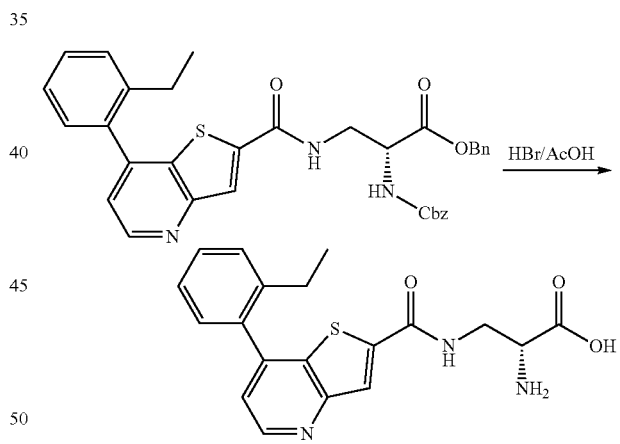

A mixture of benzyl (R)-2-(((benzyloxy)carbonyl)amino)-3-(7-(2-ethylphenyl)thieno[3,2-b]pyridine-2-carboxamido)propanoate (60 mg, 0.10 mmol) and HBr/AcOH (3 mL, 33%) was stirred at 50° C. for 16 hours. The mixture was diluted with MTBE (3 mL) and decanted with MTBE (3 mL×3). The precipitate was filtered. The filter cake was dried to give (R)-2-amino-3-(7-(2-ethylphenyl)thieno[3,2-b]pyridine-2-carboxamido)propanoic acid (43 mg) as HBr salt.

$^1$H NMR (400 MHz, DMSO-d$_6$) δ 9.24-9.22 (m, 1H), 8.87 (d, 1H), 8.41-8.26 (m, 4H), 7.54-7.44 (m, 3H), 7.41-7.36 (m, 1H), 7.35-7.30 (m, 1H), 4.24-3.77 (m, 2H), 3.74-3.69 (m, 1H), 2.45-2.43 (m, 2H), 0.96 (t, 3H).

LCMS (MH+): m/z=370.1, t$_R$ (min, Method BB)=0.46, [α]$^{20}$D=−6.67, (c=1.5 mg/mL, CH$_3$OH).

Compound 1h (R)-2-amino-3-[(7-methoxythieno[3,2-b]pyridine-2-carbonyl)amino]propanoic acid The overall synthesis scheme for the preparation of (R)-2-amino-3-[(7-methoxythieno[3,2-b]pyridine-2-carbonyl)amino]propanoic acid is shown below.

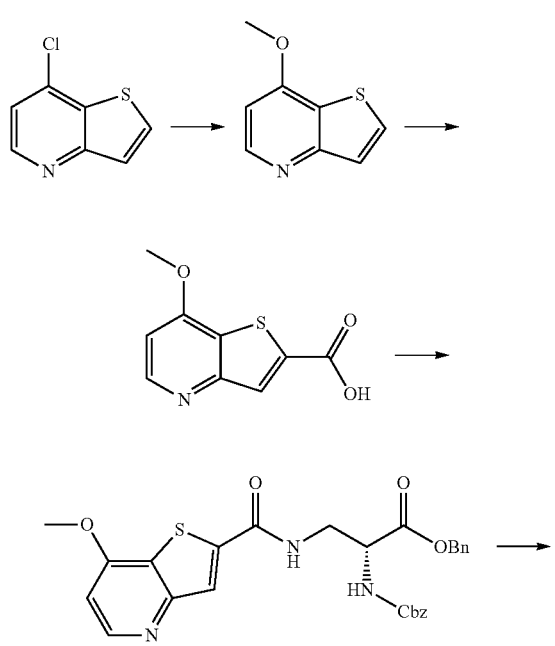

1h

Step 1: 7-methoxythieno[3,2-b]pyridine

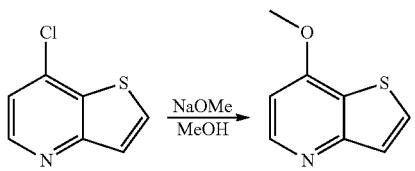

To MeOH (5.0 mL) was added Na (135 mg, 0.59 mmol). The mixture was stirred at room temperature for 1 hour, and 7-chlorothieno[3,2-b]pyridine (200 mg, 1.18 mmol) was added. The mixture was stirred in a closed vial at 110-120° C. for another 15 hours. The reaction mixture was concentrated under reduced pressure to give compound 7-methoxythieno[3,2-b]pyridine (160 mg).

$^1$H NMR (400 MHz, CDCl$_3$) δ 8.57 (d, 1H), 7.67 (d, 1H), 7.50 (d, 1H), 6.70 (d, 1H), 4.04 (s, 3H).

Step 2: 7-methoxythieno[3,2-b]pyridine-2-carboxylic acid

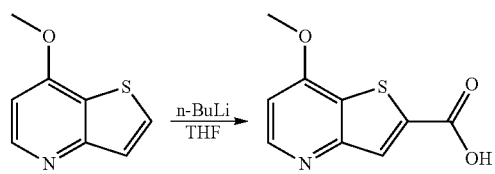

To a solution of 7-methoxythieno[3,2-b]pyridine (150 mg, 0.90 mmol) in THF (15 mL) was added n-BuLi (2.5 M in hexane, 0.5 mL) at −78° C. The mixture was stirred at −78° C. for 0.5 hour. CO$_2$ was bubbled into the solution for 0.5 hour. The mixture was warmed to room temperature and stirred for another 15 hours. The reaction mixture was concentrated under reduced pressure to remove the solvent. The residue was diluted with water (20 mL) and HCl (2M, to pH~5), filtered and the filter cake was concentrated under reduced pressure to give 7-methoxythieno[3,2-b]pyridine-2-carboxylic acid (120 mg).

$^1$H NMR (400 MHz, DMSO-d$_6$) δ 8.56 (br, 1H), 7.86 (s, 1H), 7.04 (br, 1H), 4.01 (s, 3H).

Step 3: Benzyl (R)-2-(((benzyloxy)carbonyl)amino)-3-(7-methoxythieno[3,2-b]pyridine-2-carboxamido)propanoate

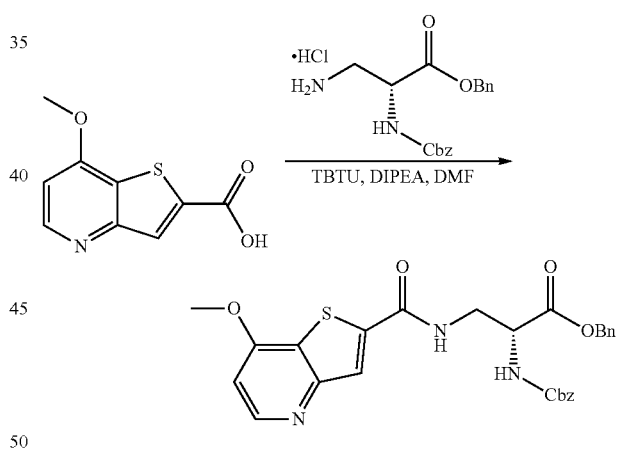

To a solution of 7-methoxythieno[3,2-b]pyridine-2-carboxylic acid (120 mg, 0.57 mmol) and (R)-benzyl 3-amino-2-(((benzyloxy) carbonyl)amino) propanoate (207 mg, 0.63 mmol, HCl salt) in DMF (5 mL) was added O-(Benzotriazol-1-yl)-N,N,N',N'-tetramethyluronium tetrafluoroborate (276 mg, 0.86 mmol) and N,N-diisopropylethylamine (370 mg, 2.87 mmol). The mixture was stirred at 20-30° C. for 16 hours. The residue was diluted with water (20 mL) and extracted with EtOAc (20 mL×2). The combined organic layers were washed with brine (10 mL), dried over MgSO$_4$, filtered and concentrated under reduced pressure to give a residue. The residue was purified by flash silica gel chromatography (Eluent of 0100% Ethyl acetate/Petroleum ether) to give benzyl (R)-2-(((benzyloxy)carbonyl)amino)-3-(7-methoxythieno[3,2-b]pyridine-2-carboxamido)propanoate (48 mg).

Step 4: (R)-2-amino-3-[(7-methoxythieno[3,2-b]pyridine-2-carbonyl)amino]propanoic acid

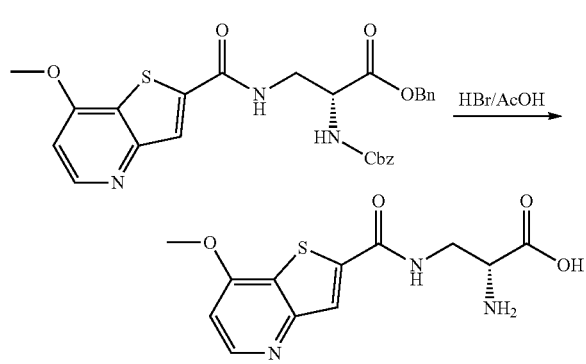

A solution of benzyl (R)-2-(((benzyloxy)carbonyl)amino)-3-(7-methoxythieno[3,2-b]pyridine-2-carboxamido) propanoate (125 mg, 0.24 mol) in HBr/AcOH (5 mL, ~33%) was stirred at 50° C. for 16 hours. The reaction mixture was concentrated under reduced pressure to remove solvent to give compound (R)-2-amino-3-(7-methoxythieno[3,2-b] pyridine-2-carboxamido) propanoic acid (100 mg) as HBr salt.

$^1$H NMR (400 MHz, DMSO-d$_6$) δ 9.52 (t, 1H), 9.00 (d, 1H), 8.40-8.30 (m, 4H), 7.52 (d, 1H), 4.22 (s, 3H), 4.15-4.13 (m, 1H), 3.84-3.72 (m, 2H).

LCMS (MH+): m/z=296.2, t$_R$ (min, Method BB)=0.28, [α]20D=−1.45, (c=2.75 g/mL, CH$_3$OH).

Compound 1i
(R)-2-amino-3-[[7-(trifluoromethyl)thieno[3,2-b]pyridine-2-carbonyl]amino]propanoic acid The overall synthesis scheme for the preparation of (R)-2-amino-3-[[7-(trifluoromethyl)thieno[3,2-b]pyridine-2-carbonyl]amino]propanoic acid is shown below.

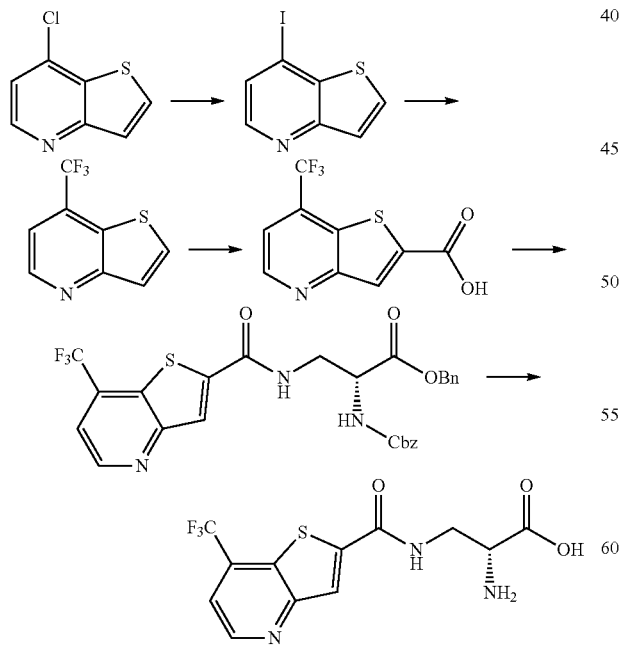

1i

Step 1: 7-Iodothieno[3,2-b]pyridine

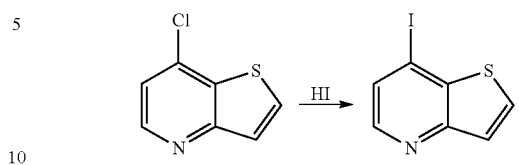

A solution of 7-chlorothieno[3,2-b]pyridine (1.00 g, 5.90 mmol) in HI (10 mL, 45% in water) was stirred at 130° C. for 16 hours. The reaction mixture was cooled to room temperature, carefully quenched with sat.aq Na$_2$CO$_3$ to pH=6~7, and extracted with EtOAc (3×10 mL). The combined organic layers were washed with brine (3×10 mL), dried over Na$_2$SO$_4$, and concentrated. The residue was purified by CombiFlash (petroleum ether/EtOAc with EtOAc from 5% to 10%) to give 7-iodothieno[3,2-b]pyridine (1.2 g).

$^1$H NMR (400 MHz, CDCl$_3$) δ 8.32 (d, J=4.8 Hz, 1H), 7.85-7.77 (m, 2H), 7.66 (d, J=5.2 Hz, 1H).

Step 2: 7-(Trifluoromethyl)thieno[3,2-b]pyridine

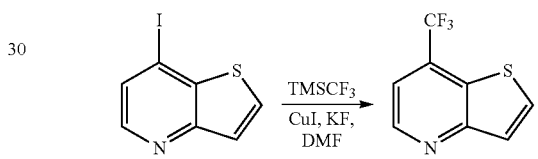

To a solution of 7-iodothieno[3,2-b]pyridine (500 mg, 1.92 mmol) in DMF (5 mL) were added CuI (401 mg, 2.11 mmol), KF (334 mg, 5.75 mmol) and TMSCF$_3$ (327 mg, 2.30 mmol). The reaction mixture was stirred at 80° C. for 16 hours. The reaction mixture was quenched with water (10 mL) and extracted with EtOAc (3×10 mL). The combined organic layers were washed with brine (3×10 mL), dried over Na$_2$SO$_4$ and concentrated. The residue was purified by CombiFlash (petroleum ether/EtOAc with EtOAc from 0% to 3%) to give 7-(trifluoromethyl)thieno[3,2-b]pyridine (140 mg).

$^1$H NMR (400 MHz, CDCl$_3$) δ 8.87 (d, J=4.4 Hz, 1H), 7.90 (d, J=5.6 Hz, 1H), 7.68 (d, J=5.6 Hz, 1H), 7.52 (d, J=4.8 Hz, 1H).

Step 3: 7-(Trifluoromethyl)thieno[3,2-b]pyridine-2-carboxylic acid

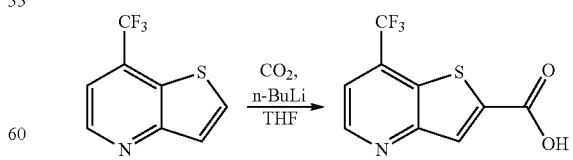

A solution of 7-(trifluoromethyl)thieno[3,2-b]pyridine (120 mg, 0.59 mmol) in THF (2 mL) was cooled to −78° C. was and treated dropwise with n-BuLi (2.5 M solution in hexanes, 0.5 ml, 1.25 mmol) and stirred at −78° C. for 30 minutes. CO$_2$ was bubbled through the reaction mixture and stirred at −78° C. for 1 hours. The reaction mixture was quenched with water (10 mL) and extracted with EtOAc (3×10 mL). The combined organic layers were washed with brine (3×10 mL), dried over Na₂SO₄ and concentrated to give 7-(trifluoromethyl)thieno[3,2-b]pyridine-2-carboxylic acid (70 mg).

Step 4: (R)-Benzyl 2-(((benzyloxy)carbonyl)amino)-3-(7-(trifluoromethyl)thieno [3,2-b]pyridine-2-carboxamido)propanoate

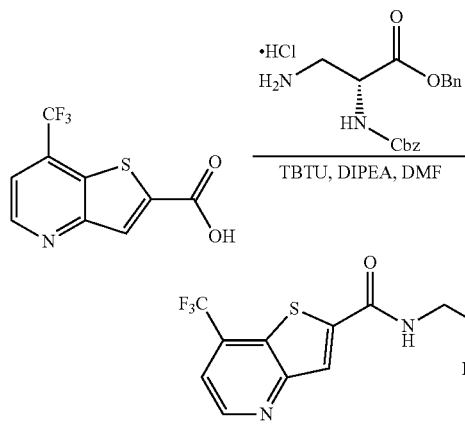

To a solution of 7-(trifluoromethyl)thieno[3,2-b]pyridine-2-carboxylic acid (130 mg, 0.52 mmol) in DMF (5 mL) were added (R)-benzyl 3-amino-2-(((benzyloxy)carbonyl) amino)propanoate (192 mg, 0.52 mmol HCl salt), O-(Benzotriazol-1-yl)-N,N,N',N'-tetramethyluronium tetrafluoroborate (253 mg, 0.79 mmol) and N,N-diisopropylethylamine (203 mg, 1.58 mmol). The reaction mixture was stirred at 25° C. for 16 hours. The reaction mixture was quenched with water (10 mL) and extracted with EtOAc (3×10 mL). The combined organic layers were washed with brine (3×10 mL), dried over Na₂SO₄ and concentrated. The residue was further purified by Preparative HPLC (Method F) to give (R)-benzyl 2-(((benzyloxy)carbonyl)amino)-3-(7-(trifluoromethyl) thieno [3,2-b]pyridine-2-carboxamido)propanoate (50 mg).

¹H NMR (400 MHz, CDCl₃) δ 8.91 (d, J=4.8 Hz, 1H), 7.88 (s, 1H), 7.58 (d, J=4.4 Hz, 1H), 7.40-7.28 (m, 10H), 5.93 (d, J=6.8 Hz, 1H), 5.27 (s, 2H), 5.13 (s, 2H), 4.66-4.60 (m, 1H), 4.05-3.92 (m, 1H), 3.88-3.77 (m, 1H).

Step 5: (R)-2-amino-3-[[7-(trifluoromethyl)thieno[3,2-b]pyridine-2-carbonyl]amino]propanoic acid

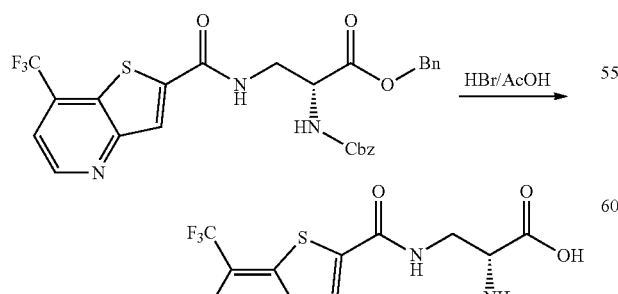

To a solution of (R)-benzyl 2-(((benzyloxy)carbonyl)amino)-3-(7-(trifluoromethyl)thieno [3,2-b]pyridine-2-carboxamido)propanoate (50 mg, 0.90 mmol) in HBr/AcOH (2 mL, 33%) was stirred at 50° C. for 16 hours. The solvent was removed under reduced pressure. The residue was purified by Preparative HPLC (Method G) to give (R)-2-amino-3-(7-(trifluoromethyl)thieno [3,2-b]pyridine-2-carboxamido) propanoic acid (8 mg) as HCl salt.

¹H NMR (400 MHz, DMSO-d₆) δ 9.69 (br, 1H), 9.02 (d, J=3.6 Hz, 1H), 8.63 (br, 4H), 7.93 (d, J=4.0 Hz, 1H), 4.20-4.10 (m, 1H), 3.79-3.77 (m, 2H).

LCMS (MH+): m/z=334.1, $t_R$ (min, Method BB)=0.36 min.

$[\alpha]^{20}D=-10.0$ (c=1.0 mg/mL, CH₃OH).

Compound 1j (R)-2-amino-3-[(7-ethoxythieno[3,2-b]pyridine-2-carbonyl)amino]propanoic acid The overall synthesis scheme for the preparation of (R)-2-amino-3-[(7-ethoxythieno[3,2-b]pyridine-2-carbonyl)amino]propanoic acid is shown below.

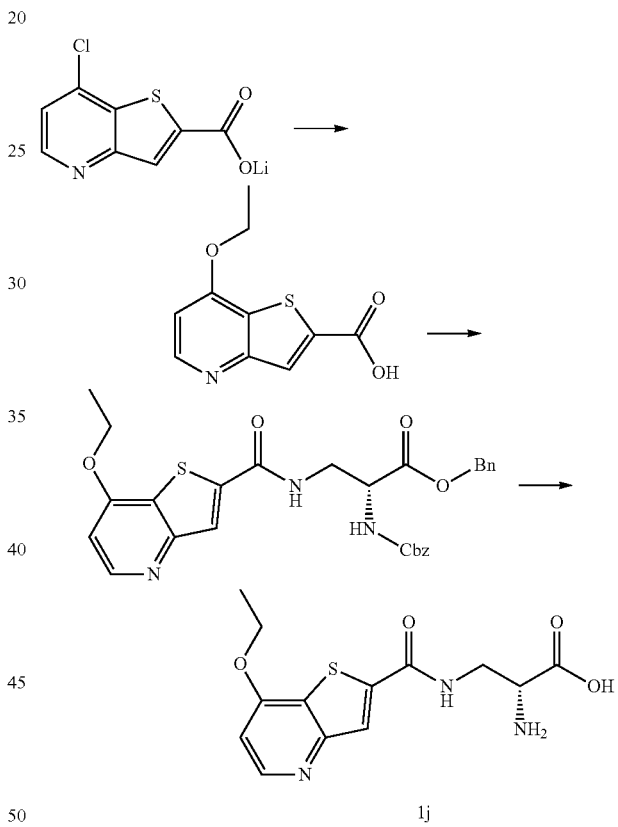

Step 1: 7-ethoxythieno[3,2-b]pyridine-2-carboxylic acid

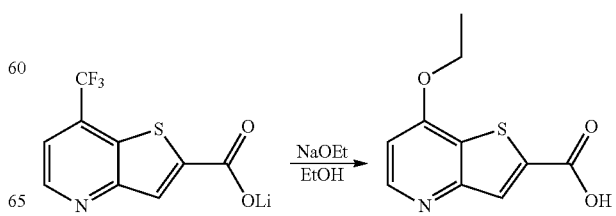

To a mixture of lithium 7-chlorothieno[3,2-b]pyridine-2-carboxylate (300 mg, 1.37 mmol) and NaOEt (372 mg, 5.47 mmol) in EtOH (20 mL) was stirred at 80° C. for 16 hours. The mixture was poured into water (20 mL), adjusted the pH (3~4) by aq. HCl (3 M) and extracted with ethyl acetate (15 mL×3). The combined organic phase was washed by brine (15 mL×3), dried over anhydrous Na$_2$SO$_4$ and concentrated to give 7-ethoxythieno [3,2-b]pyridine-2-carboxylic acid (300 mg).

$^1$H NMR (400 MHz, DMSO-d$_6$) δ 8.45 (d, J=5.2 Hz, 1H), 7.60 (d, J=6.4 Hz, 1H), 6.93 (d, J=5.2 Hz, 1H), 4.29 (q, J=6.8 Hz, 2H), 1.39 (t, J=6.8 Hz, 3H).

Step 2: (R)-benzyl-2-(((benzyloxy)carbonyl)amino)-3-(7-ethoxythieno[3,2-b]pyridine-2-carboxamido)propanoate

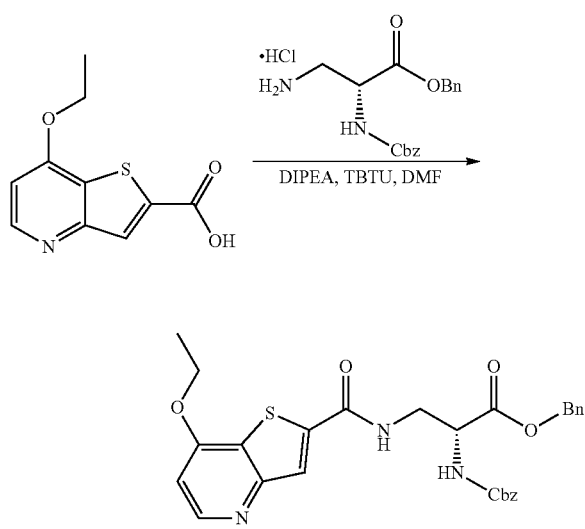

A mixture of 7-ethoxythieno[3,2-b]pyridine-2-carboxylic acid (250 mg, 1.12 mmol), (R)-benzyl 3-amino-2-(((benzyloxy)carbonyl)amino)propanoate (368 mg, 1.01 mmol, HCl salt), N,N-diisopropylethylamine (DIPEA) (434 mg, 3.36 mmol) and O-(Benzotriazol-1-yl)-N,N,N',N'-tetramethyluronium tetrafluoroborate (TBTU) (539 mg, 1.68 mmol) in DMF (5 mL) was stirred at 30° C. for 16 hours. The mixture was poured into water (10 mL) and extracted with ethyl acetate (10 mL×3). The combined organic layers were washed by brine (10 mL×3), dried over Na$_2$SO$_4$ and concentrated. The residue was purified by combiFlash (Ethyl acetate:Petroleum ether=0~75%) to give (R)-benzyl-2-(((benzyloxy)carbonyl)amino)-3-(7-ethoxythieno[3,2-b]pyridine-2-carboxamido)propanoate (120 mg).

$^1$H NMR (400 MHz, CDCl$_3$) δ 8.58 (d, J=5.2 Hz, 1H), 7.77 (s, 1H), 7.39-7.27 (m, 10H), 7.11 (br, 1H), 6.73 (d, J=5.2 Hz, 1H), 5.99 (br, 1H), 5.21 (s, 2H), 5.12 (s, 2H), 4.70-4.62 (m, 1H), 4.31 (q, J=7.2 Hz, 2H), 3.95-3.80 (m, 2H), 1.54 (t, J=7.2 Hz, 3H).

Step 3: (R)-2-amino-3-[(7-ethoxythieno[3,2-b]pyridine-2-carbonyl)amino]propanoic acid

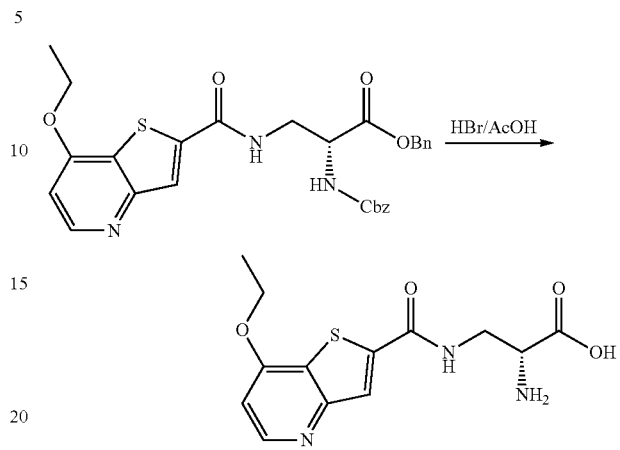

A mixture of (R)-benzyl 2-(((benzyloxy)carbonyl)amino)-3-(7-ethoxythieno[3,2-b]pyridine-2-carboxamido)propanoate (70 mg, 0.131 mmol) in HBr/AcOH (2 mL, 33%) was stirred at 50° C. for 16 hours. The mixture was concentrated in vacuo. The residue was washed with 10 mL methyl tert-butyl ether: methanol (V:V 10:1) followed by filtration. The filtered residue was dissolved in water (5 mL) and lyophilized to give (R)-2-amino-3-(7-ethoxythieno[3,2-b]pyridine-2-carboxamido)propanoic acid (35 mg) as HBr salt.

1H NMR (400 MHz, CD$_3$OD) δ 8.93 (d, J=6.8 Hz, 1H), 8.37 (s, 1H), 7.60 (d, J=6.8 Hz, 1H), 4.70 (q, J=7.2 Hz, 2H), 4.38-4.32 (m, 1H), 4.10 (dd, J=14.8, 4.0 Hz, 1H), 3.94 (dd, J=14.7, 6.7 Hz, 1H), 1.63 (t, J=6.8 Hz, 3H).

LCMS (MH+): m/z=310.2, t$_R$ (min, Method BB)=0.18.

[α]$^{20}$D=−5.7 (c=0.7 mg/mL, CH$_3$OH).

Compound 1k (R)-2-amino-3-[(7-isopropoxythieno[3,2-b]pyridine-2-carbonyl)amino]propanoic acid The overall synthesis scheme for the preparation of (R)-2-amino-3-[(7-isopropoxythieno[3,2-b]pyridine-2-carbonyl)amino]propanoic acid is shown below.

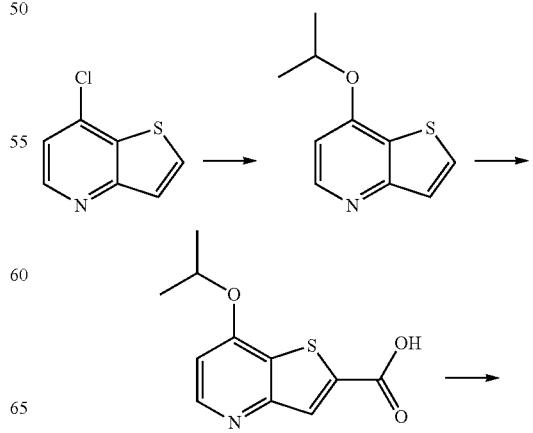

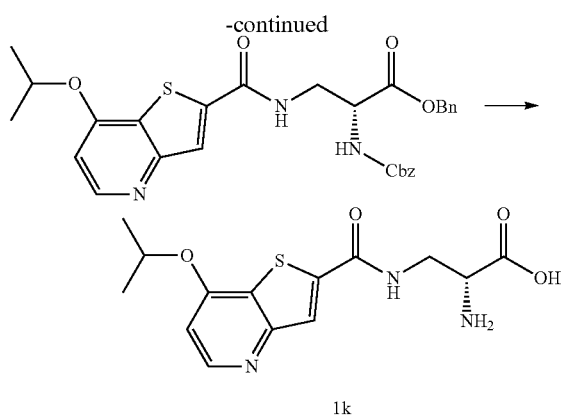

1k

Step 1: 7-isopropoxythieno[3,2-b]pyridine

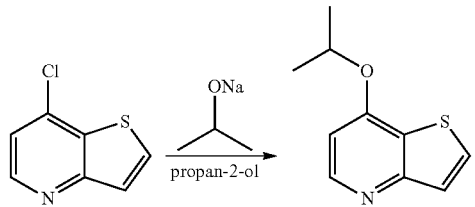

To propan-2-ol (15 mL) was added Na (339 mg, 15 mmol). The mixture was stirred at 50° C. for 1 hour and 7-chlorothieno[3,2-b]pyridine (500 mg, 2.95 mmol) was added. The mixture was stirred at 110-120° C. in a closed vial for another 15 hours. The reaction mixture was concentrated under reduced pressure to give 7-isopropoxythieno[3,2-b]pyridine (320 mg).

$^1$H NMR (400 MHz, DMSO-$d_6$) δ 8.51 (d, J=5.6 Hz, 1H), 7.66 (d, J=5.6 Hz, 1H), 7.49 (d, J=5.6 Hz, 1H), 6.70 (d, J=5.6 Hz, 1H), 4.84-4.81 (m, 1H), 1.37 (d, J=6.0 Hz, 6H).

Step 2: 7-isopropoxythieno[3,2-b]pyridine-2-carboxylic acid

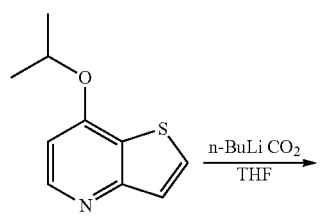

To a solution of 7-isopropoxythieno[3,2-b]pyridine (320 mg, 1.7 mmol) in THF (15 mL) was added n-BuLi (2.5 M in hexane, 0.9 mL) at −78° C. The mixture was stirred at −78° C. for 0.5 hour. $CO_2$ was bubbled into the solution for 0.5 hour. The mixture was stirred at 20-30° C. for another 15 hours. The reaction mixture was concentrated under reduced pressure to remove solvent. The residue was diluted with water (20 mL) and pH adjusted, using HCl (2M) to pH~5 The mixture was filtered and filter cake was dried under reduced pressure to give 7-isopropoxythieno[3,2-b]pyridine-2-carboxylic acid (210 mg).

$^1$H NMR (400 MHz, DMSO-$d_6$) δ 8.58 (d, J=5.4 Hz, 1H), 8.00 (s, 1H), 7.11 (d, J=5.4 Hz, 1H), 4.93-4.99 (m, 1H), 1.37 (d, J=6.0 Hz, 6H).

Step 3: Preparation of (R)-benzyl 2-(((benzyloxy)carbonyl)amino)-3-(7-isopropoxythieno[3,2-b]pyridine-2-carboxamido)propanoate

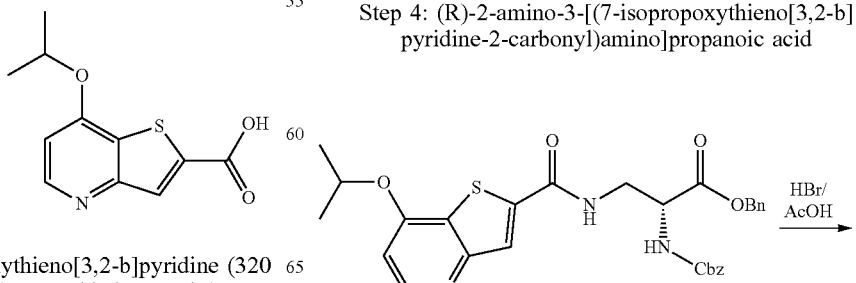

To a solution of 7-isopropoxythieno[3,2-b]pyridine-2-carboxylic acid (200 mg, 0.84 mmol) and (R)-benzyl 3-amino-2-(((benzyloxy)carbonyl)amino) propanoate (304 mg, 0.93 mmol, HCl salt) in DMF (10 mL) was added O-(benzotriazol-1-yl)-N,N,N',N'-tetramethyluronium tetrafluoroborate (406 mg, 1.3 mmol) and N,N-diisopropylethylamine (545 mg, 4.2 mmol). The mixture was stirred at 20-30° C. for 16 hours. The residue was diluted with water (20 mL) and extracted with EtOAc (20 mL×2). The combined organic layers were washed with brine (15 mL), dried over MgSO$_4$, filtered and concentrated under reduced pressure to give a residue. The residue was purified by flash silica gel chromatography (Eluent of 0~90% Ethyl acetate/Petroleum ether) to give compound (R)-benzyl 2-(((benzyloxy)carbonyl)amino)-3-(7-isopropoxythieno[3,2-b]pyridine-2-carboxamido)propanoate (86 mg).

$^1$H NMR (400 MHz, CDCl$_3$) δ 8.56 (d, J=5.2 Hz, 1H), 7.76 (s, 1H), 7.38-7.27 (m, 10H), 7.09 (br, 1H), 6.72 (d, J=5.6 Hz, 1H), 5.99 (d, J=7.2 Hz, 1H), 5.20 (s, 2H), 5.11 (s, 2H), 4.85-4.85 (m, 1H), 4.65-4.55 (m, 1H), 3.97-3.80 (m, 2H), 1.47 (d, J=5.6 Hz, 6H).

Step 4: (R)-2-amino-3-[(7-isopropoxythieno[3,2-b]pyridine-2-carbonyl)amino]propanoic acid

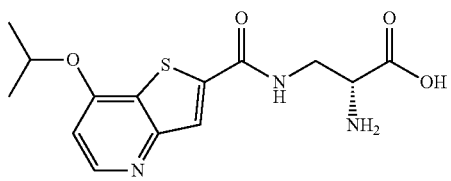

A solution of (R)-benzyl 2-(((benzyloxy)carbonyl) amino)-3-(7-isopropoxythieno[3,2-b]pyridine-2-carboxamido)propanoate (80 mg, 0.15 mmol) in HBr/AcOH (10 mL, 33%) was stirred at 50° C. for 16 hours. The reaction mixture was concentrated under reduced pressure to remove solvent. The residue was purified by Preparative-HPLC (Method H) to give (R)-2-amino-3-(7-isopropoxythieno[3,2-b]pyridine-2-carboxamido)propanoic acid (26 mg).

$^1$H NMR (400 MHz, DMSO-d$_6$) δ 9.06 (br, 1H), 8.54 (d, J=5.2 Hz, 1H), 8.10 (s, 1H), 7.57 (br, 2H), 7.08 (d, J=5.2 Hz, 1H), 5.02-4.90 (m, 1H), 3.69-3.65 (m, 1H), 3.55-3.40 (m, 2H), 1.36 (d, J=6.0 Hz, 6H).

LCMS (MH+): m/z=324.2, t$_R$ (min, Method BB)=0.24.

[α]$^{20}$D=18 (c=1 mg/mL, CH$_3$OH).

Compound 11

(R)-2-amino-3-[(7-bromothieno[3,2-b]pyridine-2-carbonyl)amino]propanoic acid The overall synthesis scheme for the preparation of (R)-2-amino-3-[(7-bromothieno[3,2-b]pyridine-2-carbonyl)amino]propanoic acid is shown below.

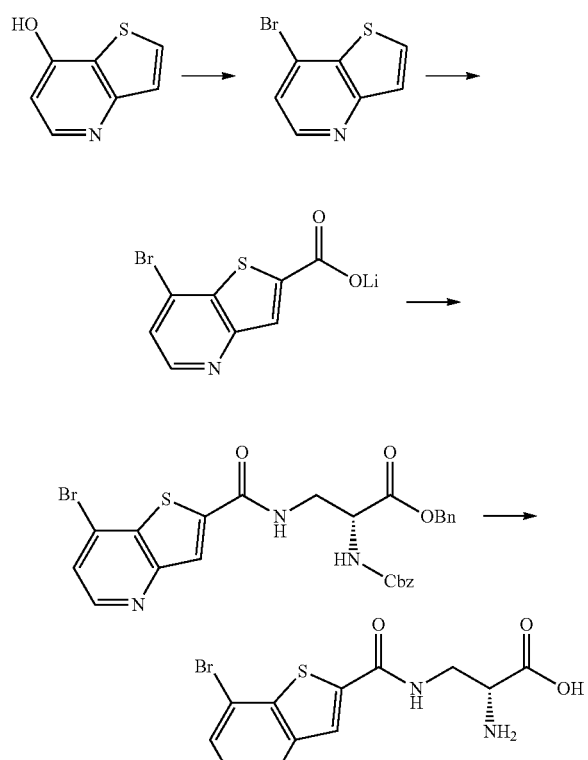

Step 1: 7-bromothieno[3,2-b]pyridine

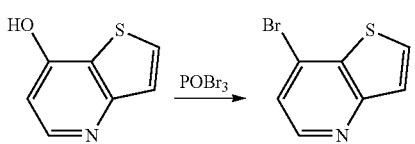

A mixture of thieno[3,2-b]pyridin-7-ol (2 g, 13 mmol) and POBr$_3$ (25 g, 8 mmol) was heated at 110° C. for 2 hours. The mixture was cooled and added to ice water (100 mL) and then added 2M NaOH solution to adjust pH to 8. The mixture was extracted with EtOAc (40 mL×3). The organic layer was dried over Na$_2$SO$_4$, filtered and concentrated. The residue was purified by Combi Flash on silica gel (petroleum ether: EtOAc with EtOAc from 0 to 30%) to give 7-bromothieno[3,2-b]pyridine (2.5 g).

$^1$H NMR (400 MHz, CDCl$_3$) δ 8.51 (d, J=4.8 Hz, 1H), 7.82 (d, J=6.0 Hz, 1H), 7.66 (d, J=5.6 Hz, 1H), 7.46 (d, J=5.2 Hz, 1H).

Step 2: Lithium 7-bromothieno[3,2-b]pyridine-2-carboxylate

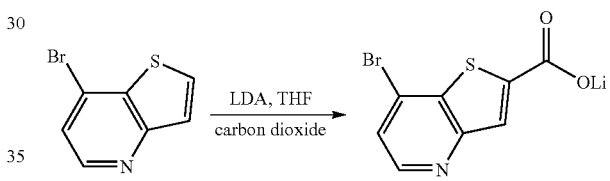

To a solution of diisopropylamine (473 mg, 4.67 mmol) in THF (20 mL) was added n-BuLi (2.5 M in hexane, 1.87 mL) dropwise at −70° C. The solution was stirred at −70° C. for 30 min. Then 7-bromothieno[3,2-b]pyridine (1 g, 4.67 mmol) dissolved in THF (5 mL) was added dropwise and stirred at −70° C. for 30 min. Then gaseous carbon dioxide was bubbled through the reaction solution and the mixture was allowed to warm to 25° C. over a period of 2 hours. The mixture was filtered and the filter cake was washed with THF (10 mL×2). The solid was collected and dried to give lithium 7-bromothieno[3,2-b]pyridine-2-carboxylate (800 mg).

$^1$H NMR (400 MHz, DMSO-d$_6$) δ 8.47 (d, J=5.2 Hz, 1H), 7.68 (s, 1H), 7.62 (d, J=5.2 Hz, 1H).

Step 3: (R)-benzyl 2-(((benzyloxy)carbonyl)amino)-3-(7-bromothieno[3,2-b]pyridine-2-carboxamido)propanoate

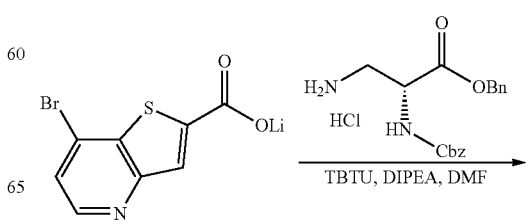

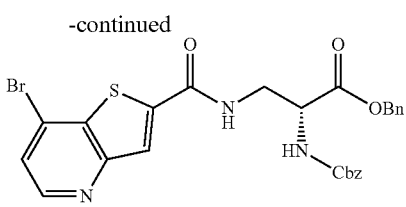

To a solution of lithium 7-bromothieno[3,2-b]pyridine-2-carboxylate (200 mg, 0.76 mmol) in DMF (5 mL) was added O-(Benzotriazol-1-yl)-N,N,N',N'-tetramethyluronium tetrafluoroborate (268 mg, 0.83 mmol), N,N-diisopropylethylamine (196 mg, 1.52 mmol) and (R)-benzyl 3-amino-2-(((benzyloxy)carbonyl)amino)propanoate (276 mg, 0.76 mmol, HCl salt). The mixture was stirred at 25° C. for 2 hours. The mixture was diluted with water (15 mL) and extracted with EtOAc (20 mL×3). The combined organic layers were washed with brine (20 mL×3), dried over $Na_2SO_4$, filtered and concentrated. The residue was purified by Combi Flash on silica gel (petroleum ether: EtOAc with EtOAc from 0 to 80%) twice to give compound (R)-benzyl 2-(((benzyloxy)carbonyl)amino)-3-(7-bromothieno[3,2-b]pyridine-2-carboxamido)propanoate (190 mg).

$^1$H NMR (400 MHz, $CDCl_3$) δ 8.54 (d, J=4.8 Hz, 1H), 7.88 (s, 1H), 7.51 (d, J=5.2 Hz, 1H), 7.38-7.24 (m, 11H), 6.05 (br d, J=6.8 Hz, 1H), 5.22 (s, 2H), 5.16-5.08 (m, 2H), 4.68-4.57 (m, 1H), 4.00-3.82 (m, 2H).

Step 4: (R)-2-amino-3-[(7-bromothieno[3,2-b]pyridine-2-carbonyl)amino]propanoic acid

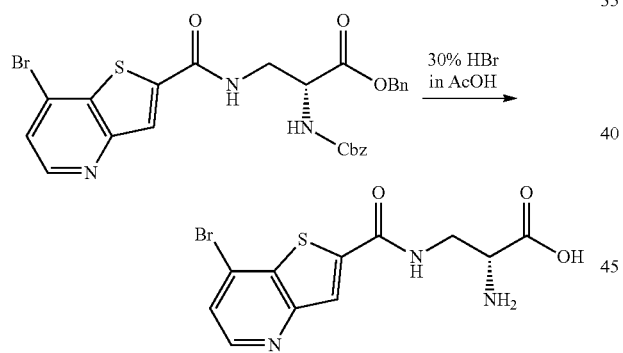

A mixture of (R)-benzyl 2-(((benzyloxy)carbonyl)amino)-3-(7-bromothieno[3,2-b]pyridine-2-carboxamido)propanoate (100 mg, 0.18 mmol) in 30% HBr in AcOH (3 mL) was stirred at 25° C. for 16 hours. The mixture was concentrated. The residue was added water (5 mL) and washed with MTBE (5 mL×2). The aqueous layer was lyophilized to give (R)-2-amino-3-(7-bromothieno[3,2-b]pyridine-2-carboxamido)propanoic acid (75 mg) as HBr salt. $^1$H NMR (400 MHz, DMSO-$d^6$) δ 9.28 (t, J=5.6 Hz, 1H), 8.64 (d, J=4.8 Hz, 1H), 8.41 (s, 1H), 8.36 (br d, J=4.0 Hz, 3H), 7.84 (d, J=4.8 Hz, 1H), 4.19-4.12 (m, 1H), 3.88-3.80 (m, 1H), 3.77-3.69 (m, 1H).

LCMS (MH+): m/z=343.9, $t_R$ (min, Method BB)=0.34. $[α]^{20}$D=−4.8 (c=3.2 mg/mL, $CH_3OH$).

Compound 1m (R)-2-amino-3-[(7-hydroxymethylthieno[3,2-b]pyridine-2-carbonyl)amino]propanoic acid The overall synthesis scheme for the preparation of (R)-2-amino-3-[(7-hydroxymethylthieno[3,2-b]pyridine-2-carbonyl)amino]propanoic acid is shown below.

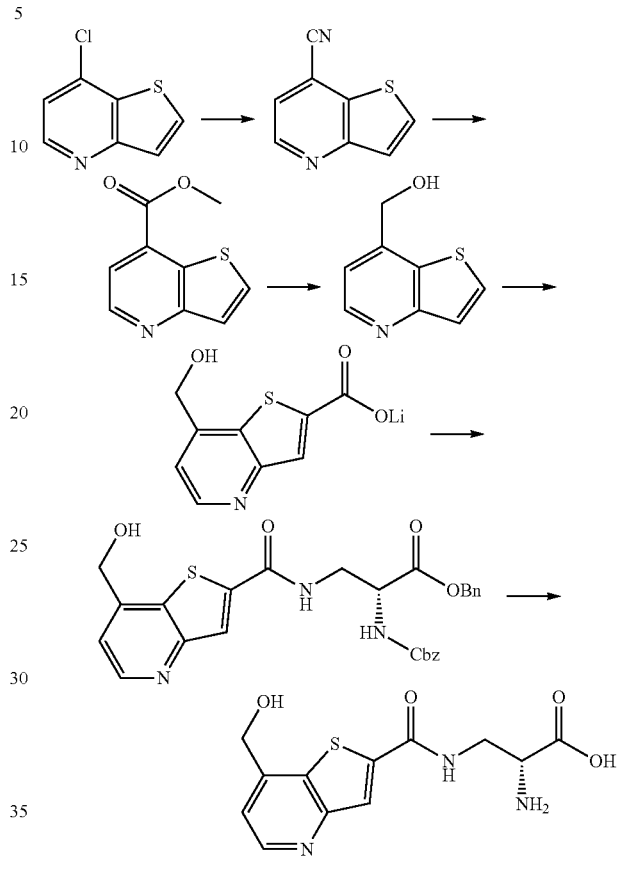

Step 1: thieno[3,2-b]pyridine-7-carbonitrile

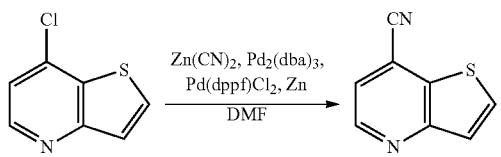

To a solution of 7-chlorothieno[3,2-b]pyridine (5 g, 29.48 mmol) and Zn(CN)$_2$ (3.77 g, 32.1 mmol) in DMF (50 mL) was added tris(dibenzylideneacetone)dipalladium(0) (Pd$_2$(dba)$_3$) (2.70 g, 2.95 mmol), Pd(dppf)Cl$_2$ (2.16 g, 2.95 mmol) and Zn power (385 mg, 5.90 mmol) under $N_2$ atmosphere. The mixture was stirred at 120° C. for 2 hours. The mixture was diluted with EtOAc (80 mL) and water (50 mL) and filtered through Celite. The filtrate was extracted with EtOAc (60 mL×2). The combined organic layers were washed with brine (50 mL×3) and concentrated. The residue was purified by Combi Flash on silica gel (petroleum ether: EtOAc with EtOAc from 0 to 20%) to give compound thieno[3,2-b]pyridine-7-carbonitrile (2.8 g).

$^1$H NMR (400 MHz, $CDCl_3$) δ 8.85 (d, J=4.8 Hz, 1H), 7.94 (d, J=5.6 Hz, 1H), 7.68 (d, J=5.6 Hz, 1H), 7.54 (d, J=4.8 Hz, 1H).

Step 2: methyl thieno[3,2-b]pyridine-7-carboxylate

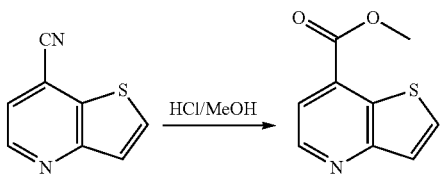

A mixture of thieno[3,2-b]pyridine-7-carbonitrile (2.8 g, 17.5 mmol) in HCl/MeOH (4 M, 50 mL) was stirred at 70° C. for 16 hours. The mixture was concentrated. The residue was added water (10 mL) and adjusted pH to 8 with aqueous 2N NaOH solution. The mixture was extracted with EtOAc (30 mL×3). The organic layer was dried over $Na_2SO_4$, filtered and concentrated. The residue was purified by Combi Flash on silica gel (petroleum ether: EtOAc with EtOAc from 0 to 35%) to give compound methyl thieno[3,2-b]pyridine-7-carboxylate (2.7 g).

$^1$H NMR (400 MHz, $CDCl_3$) δ 8.84 (d, J=4.8 Hz, 1H), 7.89 (d, J=5.6 Hz, 1H), 7.86 (d, J=4.8 Hz, 1H), 7.63 (d, J=5.6 Hz, 1H), 4.07 (s, 3H).

Step 3: thieno[3,2-b]pyridin-7-ylmethanol

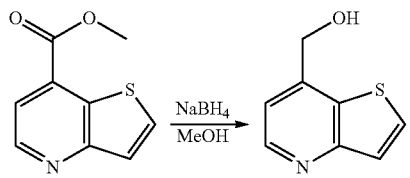

To a solution of methyl thieno[3,2-b]pyridine-7-carboxylate (2.7 g, 14 mmol) in MeOH (30 mL) was added $NaBH_4$ (793 mg, 21 mmol). The mixture was stirred at 25° C. for 3 hours. The mixture was concentrated. The residue was added water (20 mL) and extracted with EtOAc (20 mL×3). The combined organic layers were dried over $Na_2SO_4$, filtered and concentrated to give thieno[3,2-b]pyridin-7-ylmethanol (2.1 g).

$^1$H NMR (400 MHz, DMSO-$d^6$) δ 8.62 (d, J=4.4 Hz, 1H), 8.10 (d, J=5.6 Hz, 1H), 7.57 (d, J=6.0 Hz, 1H), 7.32 (d, J=4.8 Hz, 1H), 5.77 (t, J=5.6 Hz, 1H), 4.82 (d, J=5.6 Hz, 2H).

Step 4: lithium 7-(hydroxymethyl)thieno[3,2-b]pyridine-2-carboxylate

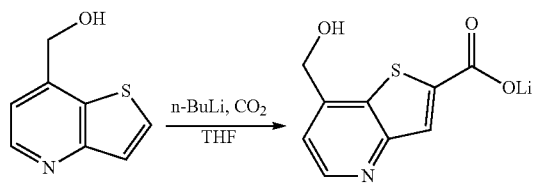

To a solution of thieno[3,2-b]pyridin-7-ylmethanol (500 mg, 3.03 mmol) in THF (20 mL) was added n-BuLi (2.5 M in hexane, 2.4 mL) dropwise at −70° C. and stirred at −70° C. for 30 min. Then gaseous carbon dioxide (15 psi) was bubbled through the reaction solution for 30 min and the mixture was allowed to warm to 25° C. over a period of 2 hours. The mixture was filtered and the filter cake was washed with THF (10 mL×2). The solid was collected and dried to give lithium 7-(hydroxymethyl)thieno[3,2-b]pyridine-2-carboxylate (700 mg).

Step 5: (R)-benzyl 2-(((benzyloxy)carbonyl)amino)-3-(7-(hydroxymethyl)thieno[3,2-b]pyridine-2-carboxamido)propanoate

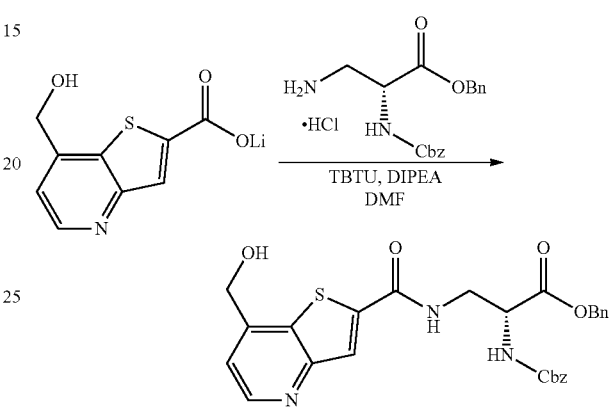

To a solution of lithium 7-(hydroxymethyl)thieno[3,2-b]pyridine-2-carboxylate (200 mg, crude) in DMF (10 mL) was added O-(Benzotriazol-1-yl)-N,N,N',N'-tetramethyluronium tetrafluoroborate (448 mg, 1.39 mmol), N,N-diisopropylethylamine (360 mg, 2.79 mmol) and (R)-benzyl 3-amino-2-(((benzyloxy)carbonyl)amino)propanoate (339 mg, 0.93 mmol, HCl salt). The mixture was stirred at 25° C. for 2 hours. The mixture was diluted with water (15 mL) and extracted with EtOAc (20 mL×3). The combined organic layers were washed with brine (20 mL×3), dried over $Na_2SO_4$, filtered and concentrated. The residue was purified by Combi Flash on silica gel (DCM:MeOH with MeOH from 0 to 10%) to give 200 mg crude product. The crude product was further purified by preparative-HPLC (Method J) to give (R)-benzyl 2-(((benzyloxy)carbonyl)amino)-3-(7-(hydroxymethyl)thieno[3,2-b]pyridine-2-carboxamido)propanoate (100 mg).

$^1$H NMR (400 MHz, DMSO-$d_6$) δ 9.01 (br t, J=5.6 Hz, 1H), 8.69 (d, J=4.8 Hz, 1H), 8.16 (s, 1H), 7.88 (d, J=8.0 Hz, 1H), 7.39 (d, J=4.8 Hz, 1H), 7.36-7.22 (m, 10H), 5.86 (t, J=5.6 Hz, 1H), 5.15-5.00 (m, 4H), 4.83 (d, J=5.2 Hz, 2H), 4.48-4.37 (m, 1H), 3.76-3.58 (m, 2H).

Step 6: (R)-2-amino-3-[(7-hydroxymethylthieno[3,2-b]pyridine-2-carbonyl)amino]propanoic acid

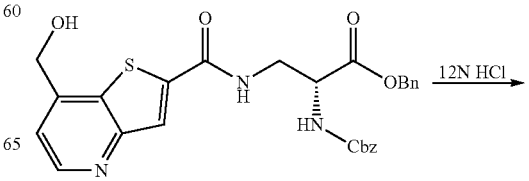

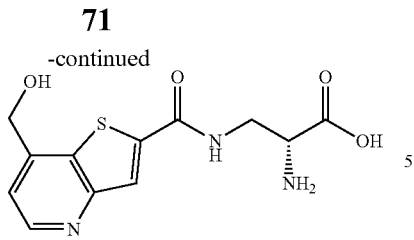
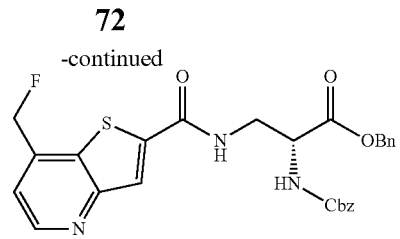

A mixture of (R)-benzyl 2-(((benzyloxy)carbonyl) amino)-3-(7-(hydroxymethyl)thieno[3,2-b]pyridine-2-carboxamido)propanoate (60 mg, 0.12 mmol) in 12M aq. HCl (12 M, 4 mL) was stirred at 80° C. for 2 hours. The mixture was concentrated. The residue was purified by preparative-HPLC (Method K) to give compound (R)-2-amino-3-(7-(hydroxymethyl)thieno[3,2-b]pyridine-2-carboxamido)propanoic acid (18 mg) as HCl salt.

$^1$H NMR (400 MHz, D$_2$O) δ 8.82 (d, J=6.0 Hz, 1H), 8.20 (s, 1H), 7.85 (d, J=6.0 Hz, 1H), 5.22 (s, 2H), 4.18-4.14 (m, 1H), 4.06-3.99 (m, 1H), 3.94-3.86 (m, 1H).

LCMS (MH+): m/z=296.1, t$_R$ (min, Method BB)=0.26.
[α]$^{20}$D=5.0 (c=1.2 mg/mL, CH$_3$OH).

Compound 1n (R)-2-amino-3-[[7-(fluoromethyl)thieno[3,2-b]pyridine-2-carbonyl]amino]propanoic acid The overall synthesis scheme for the preparation of (R)-2-amino-3-[[7-(fluoromethyl)thieno[3,2-b]pyridine-2-carbonyl]amino]propanoic acid is shown below.

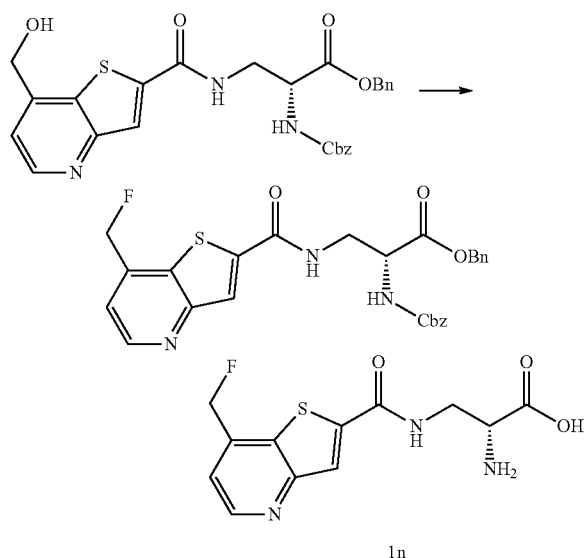

1n

Step 1: (R)-benzyl 2-(((benzyloxy)carbonyl)amino)-3-(7-(fluoromethyl)thieno[3,2-b]pyridine-2-carboxamido)propanoate

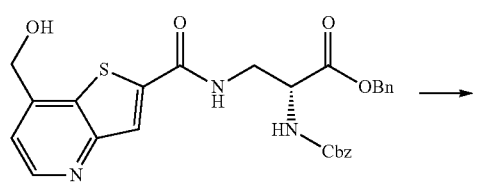

To a solution of (R)-benzyl 2-(((benzyloxy)carbonyl) amino)-3-(7-(hydroxymethyl)thieno[3,2-b]pyridine-2-carboxamido)propanoate (100 mg, 0.19 mmol) in DCM (5 mL) was added DAST (62 mg, 0.38 mmol). The mixture was stirred at 20° C. for 1 hour. The reaction was quenched with water (1 mL) and concentrated. To the residue was added water (10 mL), adjusted pH to 8 with 2N NaOH solution and extracted with EtOAc (20 mL×3). The combined organic layers were concentrated. The residue was purified by Combi Flash on silica gel (petroleum ether: EtOAc with EtOAc from 0 to 100%) to give (R)-benzyl 2-(((benzyloxy) carbonyl)amino)-3-(7-(fluoromethyl)thieno[3,2-b]pyridine-2-carboxamido)propanoate (25 mg).

$^1$H NMR (400 MHz, CDCl$_3$) δ 8.80 (s, 1H), 8.02 (s, 1H), 7.43-7.30 (m, 12H), 6.11 (br d, J=6.4 Hz, 1H), 5.71 (d, J=46.4 Hz, 2H), 5.23 (s, 2H), 5.13 (s, 2H), 4.69-4.61 (m, 1H), 4.00-3.96 (m, 2H).

Step 2: (R)-2-amino-3-[[7-(fluoromethyl)thieno[3,2-b]pyridine-2-carbonyl]amino]propanoic acid

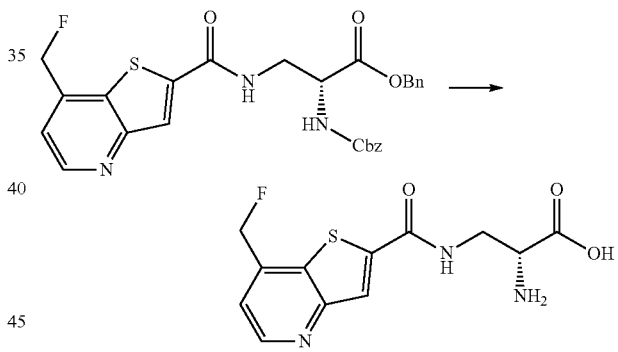

A mixture of (R)-benzyl 2-(((benzyloxy)carbonyl) amino)-3-(7-(fluoromethyl)thieno[3,2-b]pyridine-2-carboxamido)propanoate (25 mg, 0.05 mmol) in 30% HBr in AcOH (3 mL) was stirred at 50° C. for 3 hours. The mixture was concentrated. The residue was purified by preparative-HPLC (Method L) to give compound (R)-2-amino-3-(7-(fluoromethyl)thieno[3,2-b]pyridine-2-carboxamido)propanoic acid (9 mg) as HCl salt.

$^1$H NMR (400 MHz, DMSO-d$^6$) δ 9.44 (t, J=6.0 Hz, 1H), 8.80 (d, J=4.8 Hz, 1H), 8.54 (br d, J=3.6 Hz, 3H), 8.44 (s, 1H), 7.51 (d, J=4.4 Hz, 1H), 5.87 (d, J=46.0 Hz, 2H), 4.20-4.11 (m, 1H), 3.86-3.80 (m, 2H).

LCMS (MH+): m/z=298.1, t$_R$ (min, Method BB)=0.26.

Compound 1o (R)-2-amino-3-[(6-fluoro-7-methyl-thieno[3,2-b]pyridine-2-carbonyl)amino]propanoic acid The overall synthesis scheme for the preparation of (R)-2-amino-3-[(6-fluoro-7-methyl-thieno[3,2-b]pyridine-2-carbonyl)amino]propanoic acid is shown below.

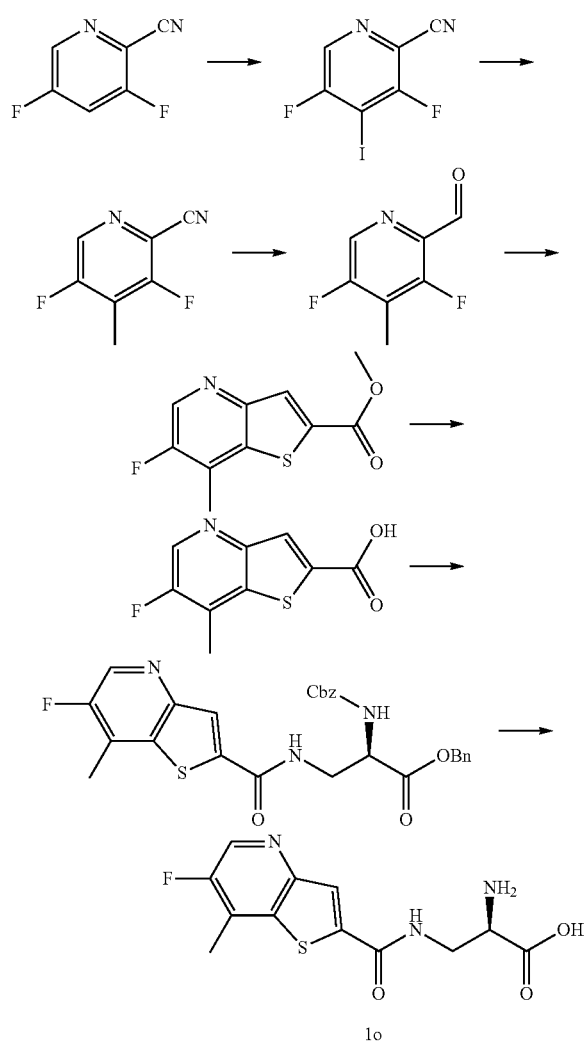

1o

Step 1: 3,5-difluoro-4-iodopicolinonitrile

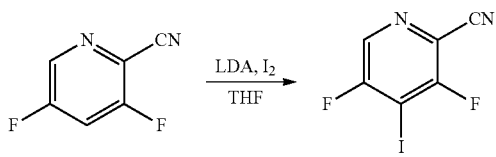 [SMILES: N#Cc1ncc(F)cc1F ; N#Cc1ncc(F)c(I)c1F ; "THF"]

To a solution of diisopropylamine (4.30 g, 42 mmol) in THF (50 mL) was added n-BuLi (17 mL, 2.5 M in hexane) at −78° C. and the reaction was stirred at −78° C. for 0.5 hour. A solution of 3,5-difluoropicolinonitrile (5 g, 36 mmol) in THF (50 mL) was added at −78° C. and the reaction mixture stirred at −78° C. for 0.5 hour. I2 (9.51 g, 37.5 mmol) was added in portions at −78° C. and the resulting mixture was stirred at −78° C. for 1 hour. H2O (50 mL) was added to quench the reaction and the mixture was extracted with EtOAc (100 mL×3). The combined organic layers were washed with brine (50 mL×2), dried over Na2SO4, filtered and concentrated. The residue was purified by Combi flash (silica gel, petroleum ether/EtOAc with EtOAc from 0~30%) to give 3,5-difluoro-4-iodopicolinonitrile (4.5 g).

$^1$H NMR (400 MHz, CDCl$_3$) δ 8.28 (s, 1H).

Step 2: 3,5-difluoro-4-methylpicolinonitrile

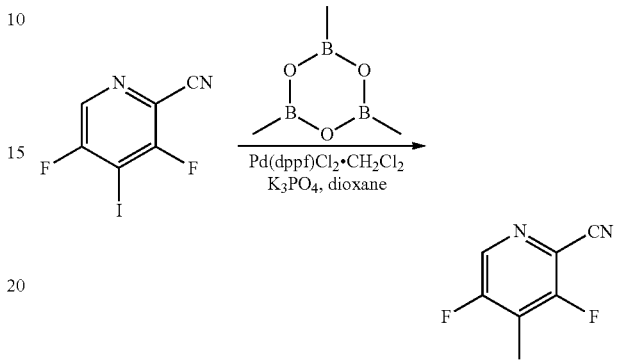

A mixture of 3,5-difluoro-4-iodopicolinonitrile (2 g, 7.52 mmol), 2,4,6-trimethyl-1,3,5,2,4,6-trioxatriborinane (5.39 g, 42.92 mmol), Pd(dppf)Cl$_2$·CH$_2$Cl$_2$ (1.84 g, 2.26 mmol) and K$_3$PO$_4$ (3.20 g, 15.08 mmol) in dioxane (10 mL) was degassed and purged with N$_2$ for 3 times, and then the mixture was stirred at 120° C. for 10 hours under N$_2$ atmosphere. H$_2$O (10 ml) was added and the mixture was extracted with EtOAc (15 mL×3). The combined organic layers were washed with brine (15 mL×2), dried over Na$_2$SO$_4$, filtered and concentrated. The residue was purified by Combi flash (silica gel, petroleum ether/EtOAc with EtOAc from 0~20%) to give 900 mg crude product. The crude product was further purified by preparative HPLC (Method I) to give 3,5-difluoro-4-methylpicolinonitrile (270 mg).

Step 3: 3,5-difluoro-4-methylpicolinaldehyde

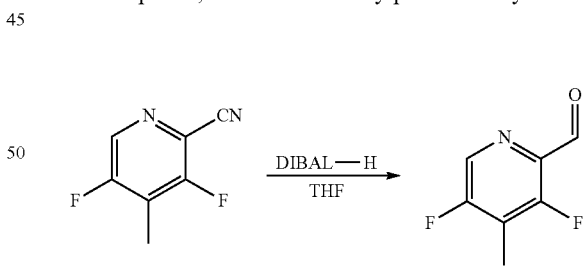

To a stirred solution of 3,5-difluoro-4-methylpicolinonitrile (270 mg, 1.75 mmol) in THF (10 mL) was added diisobutylaluminium hydride (DIBAL-H) (2.30 mL, 1M in toluene, 2.30 mmol) at −20° C. and the mixture was stirred at −20° C. for 1 hour. H$_2$O (10 mL) was added to quench the reaction and 1N HCl was added to adjust the pH to 5-6. The reaction mixture was extracted with EtOAc (15 mL×3). The combined organic layers were washed with brine (20 mL), dried over Na$_2$SO$_4$, filtered and concentrated to give 3,5-difluoro-4-methylpicolinaldehyde (270 mg).

Step 4: methyl 6-fluoro-7-methylthieno[3,2-b]pyridine-2-carboxylate

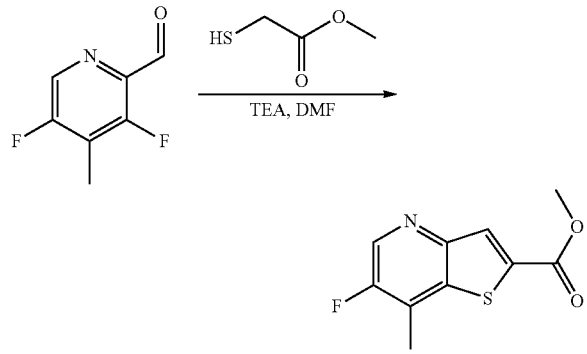

To a solution of 3,5-difluoro-4-methylpicolinaldehyde (270 mg, crude) in DMF (5 mL) was added slowly TEA (349 mg, 3.45 mmol) and methyl 2-mercaptoacetate (300 mg, 2.83 mmol) and the mixture was stirred at 100° C. for 3 hours. H$_2$O (5 ml) was added and extracted with EtOAc (5 mL×3). The combined organic layers were washed with brine (5 mL×2), dried over Na$_2$SO$_4$, filtered and concentrated. The residue was purified by Combi flash (silica gel, petroleum ether/EtOAc with EtOAc from 0~50%) to give the crude compound (200 mg). The crude compound was further purified by preparative HPLC (Method M) to give methyl 6-fluoro-7-methylthieno[3,2-b]pyridine-2-carboxylate (40 mg).

$^1$H NMR (400 MHz, CDCl$_3$) δ 8.59 (s, 1H), 8.20 (d, J=1.2 Hz, 1H), 3.99 (s, 3H), 2.55 (s, 3H).

Step 4: 6-fluoro-7-methylthieno[3,2-b]pyridine-2-carboxylic acid

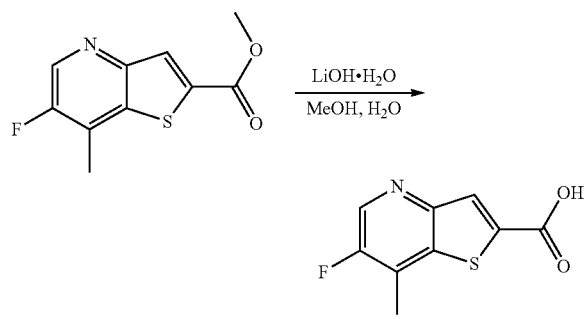

To a solution of methyl 6-fluoro-7-methylthieno[3,2-b]pyridine-2-carboxylate (40 mg, 177.59 μmol) in MeOH (4 mL) was added a solution LiOH.H$_2$O (22 mg, 524.26 μmol) in H$_2$O (1 mL) and the resulting mixture was stirred at 30° C. for 2 hours. The solvent was removed. H$_2$O (2 mL) was added, acidified with sat. KHSO$_4$ solution to pH 3~4 and extracted with EtOAc (10 mL×5). The combined organic layers were washed with brine (5 mL), dried over Na$_2$SO$_4$, filtered and concentrated to give 6-fluoro-7-methylthieno[3,2-b]pyridine-2-carboxylic acid (25 mg, 67% yield).

LC-MS: t$_R$=1.267 min, m/z=212.0 [M+H]$^+$.

Step 5: (R)-benzyl 2-(((benzyloxy)carbonyl)amino)-3-(6-fluoro-7-methylthieno[3,2-b]pyridine-2-carboxamido)propanoate

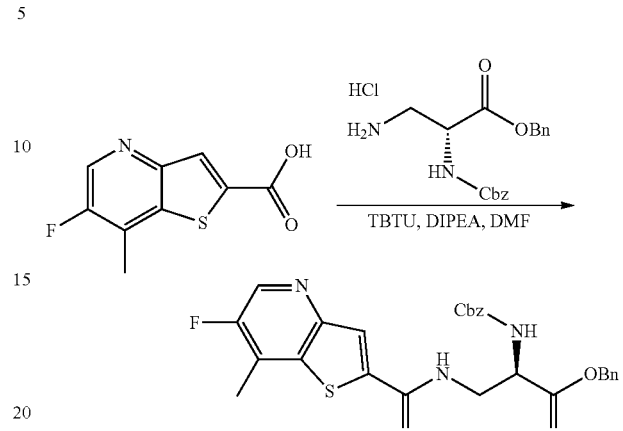

A mixture of 6-fluoro-7-methylthieno[3,2-b]pyridine-2-carboxylic acid (25 mg, 118 μmol), (R)-benzyl 3-amino-2-(((benzyloxy)carbonyl)amino)propanoate (52 mg, 142 μmol, HCl salt), O-(Benzotriazol-1-yl)-N,N,N',N'-tetramethyluronium tetrafluoroborate (57 mg, 177 μmol) and N,N-diisopropylethylamine (31 mg, 241 μmol) in DMF (2 mL) was stirred at 30° C. for 4 hours. H$_2$O (2 ml) was added to quench the reaction and extracted with EtOAc (5 mL×3). The combined organic layers were washed with brine (5 mL×2), dried over Na$_2$SO$_4$, filtered and concentrated. The residue was purified by preparative TLC (SiO$_2$, Ethyl acetate:Petroleum ether=1:1) to give (R)-benzyl 2-(((benzyloxy)carbonyl)amino)-3-(6-fluoro-7-methylthieno[3,2-b]pyridine-2-carboxamido)propanoate (25 mg).

$^1$H NMR (400 MHz, CDCl$_3$) δ 8.53 (s, 1H), 7.78 (s, 1H), 7.40-7.27 (m, 10H), 6.08 (br d, J=5.6 Hz, 1H), 5.30 (s, 1H), 5.21 (s, 2H), 5.11 (s, 2H), 4.69-4.55 (m, 1H), 3.92-3.85 (m, 2H), 2.52 (s, 3H).

Step 6: (R)-2-amino-3-[(6-fluoro-7-methyl-thieno[3,2-b]pyridine-2-carbonyl)amino]propanoic acid

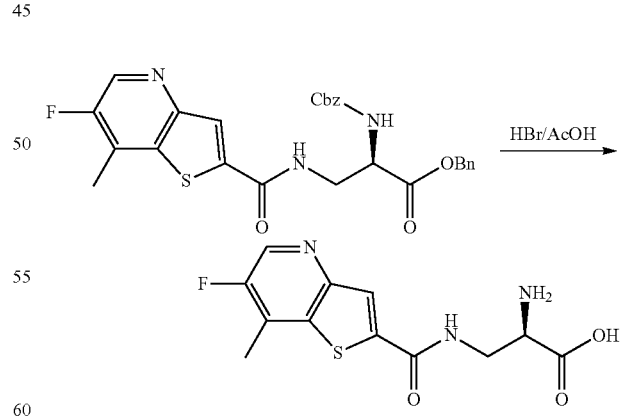

A mixture of (R)-benzyl 2-(((benzyloxy)carbonyl)amino)-3-(6-fluoro-7-methylthieno[3,2-b]pyridine-2-carboxamido)propanoate (25 mg, 48 μmol) in 33% HBr in AcOH (2 mL) was stirred at 50° C. for 16 hours. The solvent was removed. The residue was washed with TBME (5 mL×3), the solid was filtered and the residue solvent was removed by lyophilization to give (R)-2-amino-3-(6-fluoro-7-methylthieno[3,2-b]pyridine-2-carboxamido)propanoic acid (16 mg) as HBr salt.

$^1$H NMR (400 MHz, DMSO-d$^6$) δ 9.18 (t, J=5.6 Hz, 1H), 8.71 (d, J=1.6 Hz, 1H), 8.41-8.26 (m, 3H), 8.26 (s, 1H), 4.21-4.09 (m 1H), 3.86-3.78 (m, 1H), 3.76-3.67 (m, 1H), 2.50 (s, 3H).

LCMS (MH+): m/z=298, t$_R$ (min, Method BB)=0.34.

[α]$^{20}$D=−16.00 (c=2 mg/mL, MeOH).

Compound 1p (R)-2-amino-3-[(6,7-dimethylthieno[3,2-b]pyridine-2-carbonyl)amino]propanoic acid The overall synthesis scheme for the preparation of (R)-2-amino-3-[(6,7-dimethylthieno[3,2-b]pyridine-2-carbonyl)amino]propanoic acid is shown below.

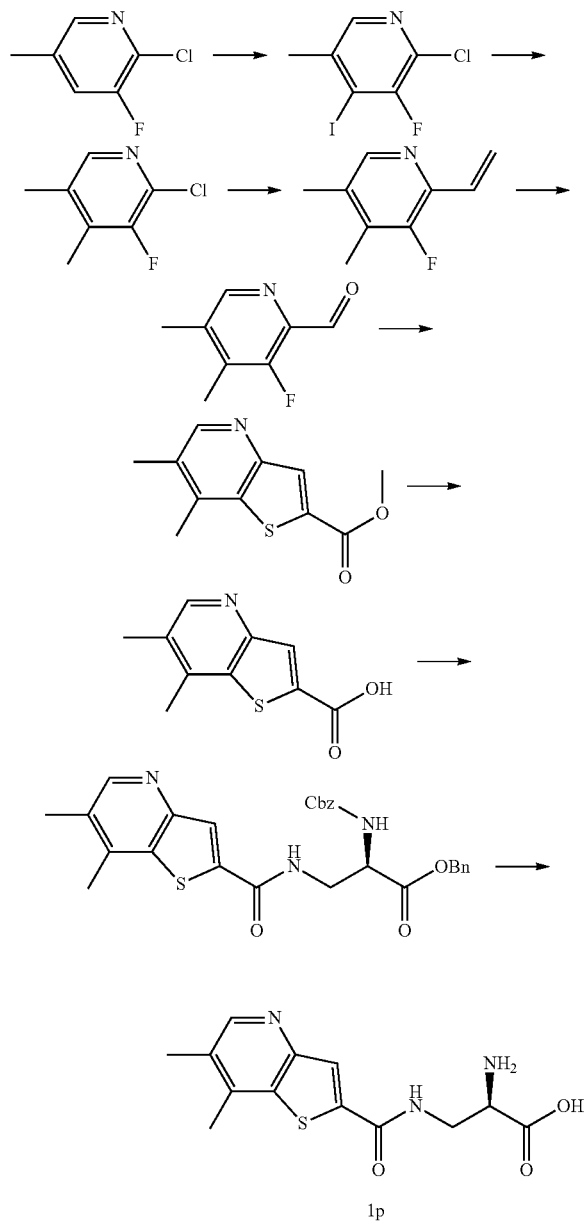

1p

Step 1: 2-Chloro-3-fluoro-4-iodo-5-methylpyridine

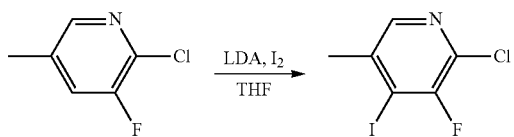

To a solution of diisopropylamine (5.8 mL, 41 mmol) in THF (50 mL) was added n-BuLi (17.5 mL, 2.5 M in hexane) at −78° C. and the reaction was stirred at −78° C. for 1 hour. A solution of 2-chloro-3-fluoro-5-methylpyridine (5.00 g, 34.4 mmol) in THF (50 mL) was added dropwise at −78° C. and the reaction mixture stirred at −78° C. for 1 hour. I2 (9.50 g, 37.4 mmol) was added in portions at −78° C. and the resulting mixture was stirred at −78° C. for 1 hour. sat.NH$_4$Cl (20 ml) was added to quench the reaction, followed by H$_2$O (50 mL) at 0° C. and extracted with EtOAc (100 mL×3). The combined organic layers were washed with brine (100 mL×2), sat.Na$_2$S$_2$O$_3$ solution (100 mL), dried over Na$_2$SO$_4$, filtered and concentrated to give 2-chloro-3-fluoro-4-iodo-5-methyl-pyridine (8.2 g).

$^1$H NMR (400 MHz, CDCl$_3$) δ 7.97 (s, 1H), 2.47 (s, 3H).

Step 2: 2-Chloro-3-fluoro-4,5-dimethylpyridine

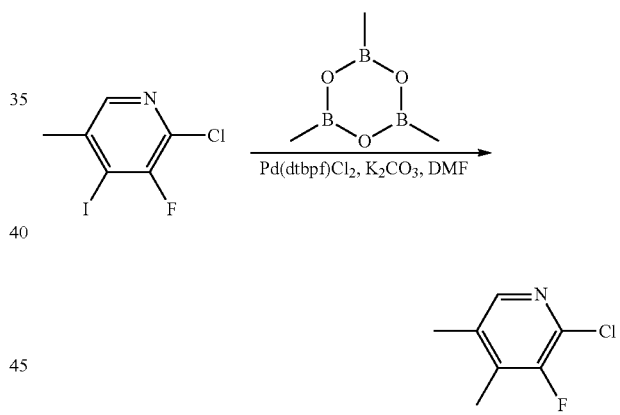

A mixture of 2-chloro-3-fluoro-4-iodo-5-methylpyridine (4.20 g, 15.5 mmol), 2,4,6-trimethyl-1,3,5,2,4,6-trioxatriborinane (4.27 g, 34.0 mmol), K$_2$CO$_3$ (4.28 g, 30.9 mmol) and pd(dtbpf)Cl$_2$ (1.01 g, 1.55 mmol) in dioxane (10 mL) was degassed by purging with N$_2$, and then the mixture was stirred at 80° C. under N$_2$ for 16 hours. Then additional 2,4,6-trimethyl-1,3,5,2,4,6-trioxatriborinane (4.27 g, 34.0 mmol) was added, and the resulting mixture was stirred at 80° C. for another 16 hours. Water (20 ml) was added to quench the reaction and extracted with EtOAc (20 mL×3). The combined organic layers were washed with brine (20 mL×2), dried over Na$_2$SO$_4$, filtered and concentrated. The residue was purified by Combi flash (silica gel, petroleum ether/EtOAc with EtOAc from 0~10%) to give 2-chloro-3-fluoro-4,5-dimethylpyridine (1.2 g).

$^1$H NMR (400 MHz, CDCl$_3$) δ 7.95 (s, 1H), 2.22-2.27 (m, 6H).

Step 3: 3-Fluoro-4,5-dimethyl-2-vinylpyridine

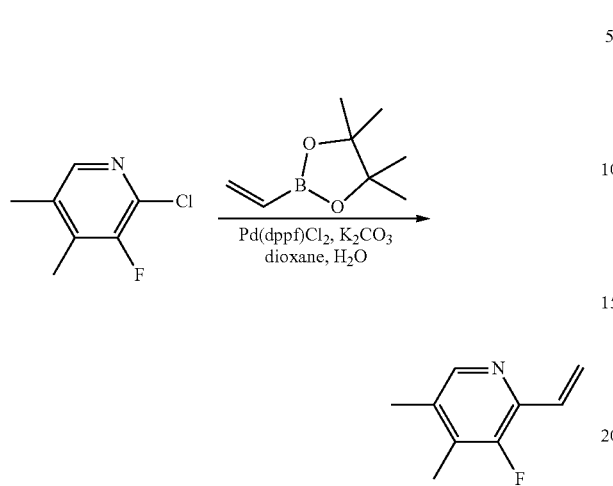

A mixture of 2-chloro-3-fluoro-4,5-dimethylpyridine (1.70 g, 10.7 mmol), 4,4,5,5-tetramethyl-2-vinyl-1,3,2-dioxaborolane (2.46 g, 15.9 mmol), Pd(dppf)Cl$_2$ (780 mg, 1.07 mmol) and K$_2$CO$_3$ (2.94 g, 21.3 mmol) in a mixture of dioxane (80 mL) and H$_2$O (8 mL) was degassed by purging with N$_2$, and then the mixture was stirred at 80° C. for 16 hours under N$_2$ atmosphere. H$_2$O (50 ml) was added and extracted with EtOAc (50 mL×3). The combined organic layers were washed with brine (50 mL×2), dried over Na$_2$SO$_4$, filtered and concentrated. The residue was purified by Combi flash (silica gel, petroleum ether/EtOAc with EtOAc from 0 to 30%) to give 3-fluoro-4,5-dimethyl-2-vinylpyridine (1.0 g).

$^1$H NMR (400 MHz, CDCl$_3$) δ 8.10 (s, 1H), 7.04-6.82 (m, 1H), 6.31 (dd, J=2.0 Hz, 17.6 Hz, 1H), 5.48 (dd, J=2.0 Hz, 11.2 Hz, 1H), 2.4 (s, 3H), 2.18 (d, J=2.0 Hz, 3H).

Step 4: 3-Fluoro-4,5-dimethylpicolinaldehyde

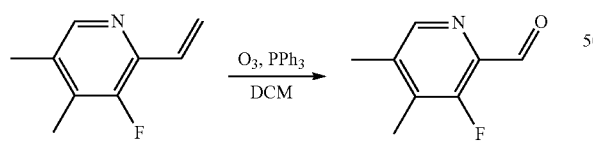

Ozone (15 psi) was bubbled through a solution of 3-fluoro-4,5-dimethyl-2-vinylpyridine (1.00 g, 6.61 mmol) in DCM (200 mL) at −70° C. for 15 min. Then PPh$_3$ (2.08 g, 7.94 mmol) was added at −70° C., the mixture was stirred at 25° C. for 2 hours. The mixture was concentrated in vacuo keeping the temperature below 40° C., and the resulting residue was purified by Combi Flash on silica gel (petroleum ether: EtOAc with EtOAc from 0 to 50%) to give 3-fluoro-4,5-dimethylpicolinaldehyde (600 mg).

$^1$H NMR (400 MHz, CDCl$_3$) δ 10.16 (s, 1H), 8.37 (s, 1H), 2.39 (s, 3H), 2.30 (s, 3H).

Step 5: Methyl 6,7-dimethylthieno[3,2-b]pyridine-2-carboxylate

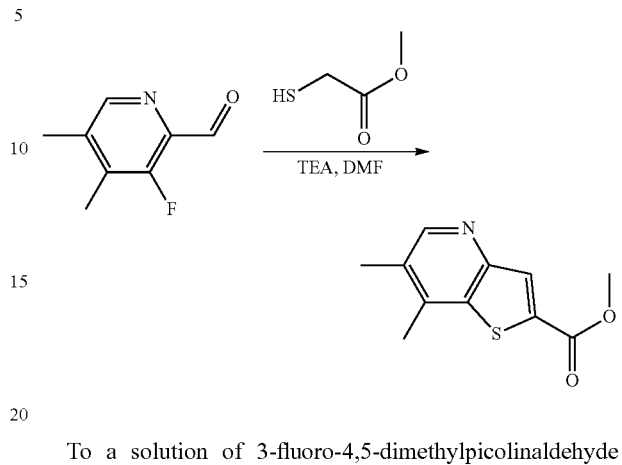

To a solution of 3-fluoro-4,5-dimethylpicolinaldehyde (550 mg, 3.59 mmol) in DMF (10 mL) was added TEA (1 mL, 7.18 mmol) and stirred at 25° C. for 30 min, then methyl 2-sulfanylacetate (460 mg, 4.33 mmol) was added slowly. The mixture was stirred at 100° C. for 3 hours. H$_2$O (10 ml) was added to quench the reaction and the mixture was extracted with EtOAc (10 mL×3). The combined organic layers were washed with brine (10 mL×2), dried over Na$_2$SO$_4$, filtered and concentrated to give methyl 6,7-dimethylthieno[3,2-b]pyridine-2-carboxylate (800 mg), which was used without any further purification.

$^1$H NMR (400 MHz, CDCl$_3$) δ 8.53 (s, 1H), 8.18 (s, 1H), 3.97 (s, 3H), 2.52 (s, 3H), 2.43 (s, 3H).

Step 6: 6,7-Dimethylthieno[3,2-b]pyridine-2-carboxylic acid

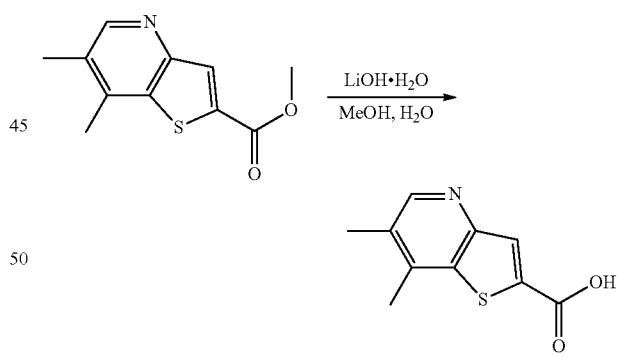

To a solution of methyl 6,7-dimethylthieno[3,2-b]pyridine-2-carboxylate (400 mg, crude) in MeOH (8 mL) was added a solution of LiOH.H$_2$O (160 mg, 3.81 mmol) in H$_2$O (2 mL) and the resulting mixture was stirred at 25° C. for 1 hour. The mixture was concentrated, and water (5 mL) was added, followed by extraction with EtOAc (5 mL×2). The organic layers were discarded and the aqueous layer was acidified with sat. KHSO$_4$ solution to pH 3. The solid was filtered and dried to give 6,7-dimethylthieno[3,2-b]pyridine-2-carboxylic acid (140 mg). $^1$H NMR (400 MHz, DMSO-d$_6$) δ 13.60 (brs, 1H), 8.55 (s, 1H), 8.05 (s, 1H), 2.50 (s, 3H), 2.39 (s, 3H).

Step 7: (R)-Benzyl 2-(((benzyloxy)carbonyl)amino)-3-(6,7-dimethylthieno[3,2-b]pyridine-2-carboxamido)propanoate

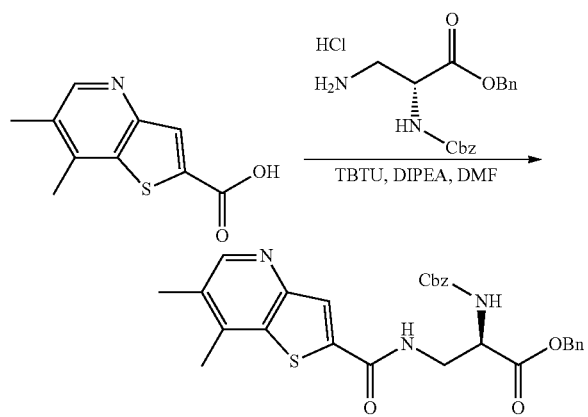

A mixture of 6,7-dimethylthieno[3,2-b]pyridine-2-carboxylic acid (70 mg, 338 μmol), (R)-benzyl 3-amino-2-(((benzyloxy)carbonyl)amino)propanoate (148 mg, 406 μmol, HCl salt), O-(Benzotriazol-1-yl)-N,N,N',N'-tetramethyluronium tetrafluoroborate (163 mg, 508 μmol) and N,N-diisopropylethylamine (88.0 mg, 677 μmol) in DMF (5 mL) was stirred at 25° C. for 16 hours. H$_2$O (5 ml) was added to quench the reaction and extracted with EtOAc (5 mL×3). The combined organic layers were washed with brine (5 mL×2), dried over Na$_2$SO$_4$, filtered and concentrated. The residue was purified by preparative TLC (SiO$_2$, Ethyl acetate:Petroleum ether=2:1) to give (R)-benzyl 2-(((benzyloxy)carbonyl)amino)-3-(6,7-dimethylthieno[3,2-b]pyridine-2-carboxamido)propanoate (100 mg).

$^1$H NMR (400 MHz, CDCl$_3$) δ 8.50 (s, 1H), 7.77 (s, 1H), 7.42-7.28 (m, 10H), 7.08 (br s, 1H), 6.01 (d, J=6.4 Hz, 1H), 5.22 (s, 2H), 5.12 (s, 2H), 4.63 (d, J=3.6 Hz, 1H), 4.00-3.81 (m, 2H), 2.51 (s, 3H), 2.42 (s, 3H).

Step 8: (R)-2-amino-3-[(6,7-dimethylthieno[3,2-b]pyridine-2-carbonyl)amino]propanoic acid

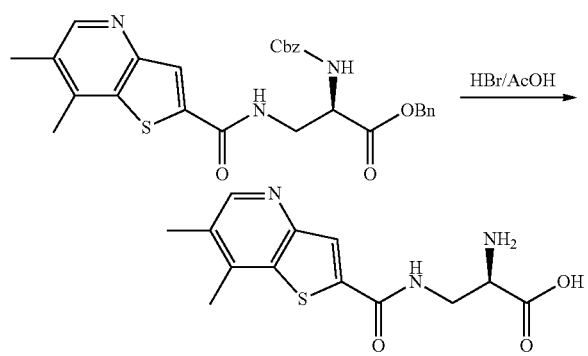

A mixture of (R)-benzyl 2-(((benzyloxy)carbonyl)amino)-3-(6,7-dimethylthieno[3,2-b]pyridine-2-carboxamido)propanoate (100 mg, 193 μmol) in 33% HBr in AcOH (5 mL) was stirred at 50° C. for 16 hours. The mixture was concentrated. The solid was suspended in AcOH (5 mL), filtered, and washed with additional AcOH (1 mL×2). The solvent was removed by lyophilization to give (R)-2-amino-3-(6,7-dimethylthieno[3,2-b]pyridine-2-carboxamido)propanoic acid (77 mg) as HBr salt.

$^1$H NMR (400 MHz, DMSO-d$^6$) δ 9.27 (t, J=5.2 Hz, 1H), 8.69 (s, 1H), 8.29-8.41 (m, 3H), 8.27 (s, 1H), 4.11-4.22 (m, 1H), 3.72-3.84 (m, 2H), 2.58 (s, 3H), 2.44 (s, 3H).

LCMS (MH+): m/z=294.2, t$_R$ (min, Method BB)=0.24. [α]$^{20}$D=−3.00 (c=6 mg/mL, MeOH).

e. In Vitro and In Vivo Characterization of Compounds of the Invention

Example 1

Affinity Data of the Exemplified Compounds of the Invention

Scintillation Proximity Assay (SPA):

To determine the affinity of the compounds of the present invention a SPA is used. The assay is run in a 384-plate format (OptiPlate-384) where each well contains a mix of 5 μL of test compound, 5 μL NR1s1s2 (ligand binding domains of the NMDA receptor, MW 35.6 kDa, 0.075 ug/well final), 5 μL [$^3$H]-MDL-105,519 (radiolabelled, high affinity N-methyl-D-aspartate (NMDA) glutamate receptor antagonist at the glycine site, final concentration 5 nM, Kd=1.3 nM), 5 μL streptavidin coated imaging beads (Perkin Elmer cat. No.: RPNQ0273, 8 ug/well). The assay buffer contains 100 mM HEPES-NaOH, 150 mM NaCl, 1 mM EDTA, 10% glycerol at pH 7.4 in ultra-pure water. Non-specific binding is defined by inclusion of 10 μM L-689,560 (highly potent NMDA antagonist) and total binding by 1% DMSO. Following 30 minutes incubation in the dark (shaker, Multi-microplate Genie), the SPA beads are allowed to settle for 3 hours after which the signal is read on a Viewlux instrument (Perkin Elmer). Normalized data are used to calculate Ki values.

TABLE 2

SPA Ki (nm) values of the compound of the invention

| Example | SPA Ki (nM) |
| --- | --- |
| 1a | 7400 |
| 1b | 270 |
| 1c | 170 |
| 1d | 140 |
| 1e | 96 |
| 1f | 220 |
| 1g | 860 |
| 1h | 690 |
| 1i | 360 |
| 1j | 870 |
| 1k | 220 |
| 1l | 63 |
| 1m | 3900 |
| 1n | 180 |
| 1o | 260 |
| 1p | 490 |

Table 2 shows that compounds of formula V have affinity to the glycine site of the NMDA receptor.

Example 2

In Vivo Exposure Data

In Vivo Procedure:

Brain disposition of test compound was evaluated in male Sprague Dawley rats (standard body weight range). Briefly, discrete (nominal dose: 2 mg/kg, 2 ml/kg) or cassetted (nominal dose: 1 mg/kg/compound, 2 ml/kg) test compounds were administered by intravenous bolus injection (formulated in 10% hydroxypropyl-β-cyclodextrin or 10-20% Captisol, pH=3).

Sample Collection:

Serial blood samples were collected from a lateral tail vein at designated time points (n=3 per time point) then rats were put under deep isoflurane induced anesthesia prior to removal of brains (n=3 per time point). Blood was collected into K3-EDTA-coated tubes and the samples were gently turned upside-down to ensure a homogenous sample. The tubes were centrifuged at 3300×g for 10 min. at max 4° C. and plasma samples were transferred to Micronic tubes. Brain samples were dissected once the animal had been sacrificed, slightly "dipped" on filter paper to remove blood overflow on the outside and transferred into Covaris AFA tubes. Plasma and brain samples were stored at −80° C. until analysis.

Sample Preparation:

Seven calibration standards and three QC samples were prepared in plasma and brain homogenate, respectively, in the concentration range 10-10000 ng/mL. Blank samples (control matrix with internal standard) were prepared and treated in the same way as calibration standards. Prior to analysis, the brain samples were homogenized with milliQ water 1:4 (w/v) using a Covaris focused-ultrasonicator. Study samples with expected concentration above upper limit of quantification were diluted with blank matrix.

Brain homogenate and plasma from study samples, calibration standards, quality controls and blank samples were subsequently treated with the same extraction procedure, i.e. protein precipitation by adding 150 μL acetonitrile with internal standard (Tolbutamide) to 25 μL of sample. Samples were centrifuged and the supernatant from each sample was diluted 1:1 with water to lower the content of organic solvent.

LC-MS/MS:

Samples were analyzed using an AB Sciex API4000 triple quadrupole (TQ) mass spectrometer operated in positive and negative electrospray ionization and MS/MS mode (multiple reaction monitoring, MRM). The mass spectrometer was coupled to a Waters Acquity UPLC equipped with a Waters Acquity UPLC HSS C18 SB (1.7 μm, 30 mm×2.1 mm) analytical column. Chromatographic separation was achieved by a 3-minute gradient starting with 98% mobile phase A (0.1% Formic Acid in water) and 2% mobile phase B (0.1% Formic Acid in Acetonitrile) increasing to 95% mobile phase B. Flow rate was 0.6 mL/min and the column temperature was 40° C. MRM transitions (m/z) were as follows: 380→248, 350→263, Tolbutamide: 269→106 (neg) and 271→155 (pos). Quantification was performed by linear regression, 1/x2 weighting.

The blood brain deposition data is shown in table 3 below.

TABLE 3 blood brain deposition data for compounds of the invention

| Example dosed | Dose mg/kg | Total Plasma concentration (ng/mL) 30 min post dose | Total Brain concentration (ng/mL) 30 min post dose |
|---|---|---|---|
| 1e | 2 | 270 | 8.4 |

Conclusion. The results show that brain exposure of the test compound post intravenous dosing is achieved.

Example 3

Resting State Electroencephalography (rsEEG) in Rats

On the day of surgery, rats (270-300 g) were anesthetized with a 0.25 ml/100 g subcutaneous (SC) injection of 1:1 hypnorm/Dormicum and mounted in a stereotaxic frame (David Kopf Instruments, Tujunga, Calif., USA) with blunt ear bars. Marcain (0.2 ml SC) was injected under the scalp, and gel (Neutral Opthta Eye Gel) put on the eyes to prevent the mucous membrane drying out. Holes were burred in the skull to allow for placement of three depth electrodes (E363-series; PlasticsOne, Roanoke, Va., USA) in medial prefrontal cortex (mPFC) (AP: 3.0 mm from the bregma suture, ML: −0.7 mm from the sagittal suture and DV: 3.0 mm from the dura), Nucleus accumbens (NAc): (AP+1.6 mm from the bregma suture, ML: −1.0 mm from the sagittal suture, DV: −6.7 mm from the dura) and thalamus (AP: −2.8 mm from the bregma suture, ML: +0.7 mm from the sagittal suture and DV: 4.4 mm from the dura) and three screw electrodes above the auditory cortex (A1) (AP: −4.8 mm from the bregma suture, ML: +6.4 mm from the sagittal suture), a reference electrode (AP: +8.0 mm and ML: −2.0 mm), and a ground electrode (AP: −5 mm, ML: +5 mm). During surgeries, nails were cut to prevent rats from scratching wounds following surgery. After completion of surgeries, rats were placed under warming lamps until recovery of consciousness (maximum 4 hours). Water soaked food pellets were placed in the home cage, so the rat easily and quickly could start feeding. Extra muesli was supplied to aid the recovery. Rats were treated with Norodyl and Noromox for 5 days in total and closely observed during a 10-14-day post-surgery recovery period. Animal bodyweights were recorded daily. No rats lost more than 10% of their pre-surgery bodyweight. Sutures were removed after 7-10 days. At the end of experiments electrical lesions were performed in all recording electrodes and brains were cut for visual microscopy inspection of electrode placement. The differences between depth- and screw-electrode impedances were handled by investigating relative power changes and common-mode noise sources were reduced from recording in shielded boxes and excluding power estimates around 50, 100, and 150 Hz from analyses.

Rats were handled daily and habituated to recording box the week before recording sessions. Recordings were performed during the dark phase of the light/dark cycle. At 8 AM, rats (400-500 g) were individually transferred to an acrylic chamber (30 cm wide 45 cm deep 55 cm high) placed within an electrically shielded sound-proof box (90 cm wide 55 cm deep 65 cm high) and were tethered to a six-pin wire suspended from a rotating swivel, allowing free movement within the recording box. There was a 2-hour habituation period followed by 45 minutes of baseline recording, where after rats were injected subcutaneously with 10% captisol (vehicle), 20 mg/kg compound 1e or and left in the box for two more hours. Rats only went through recording sessions once a week with at least six days between recordings to allow for wash-out of compounds. The analog LFP/ECoG signals were amplified and band-pass filtered at 0.01-300 Hz (Precision Model 440; Brownlee, Palo Alto, Calif., USA) and converted to a digital signal at a sampling rate of 1 kHz (CED Power 1401, Power 1 (625 kHz, 16 bit) and CED Expansion ADC16; CED, Cambridge, England). Video recordings were processed in EthoVision. The analysis of the locomotor behaviour was based on the recorded accelerometer signal. The accelerometer signal thresholds were validated to detect periods of locomotor activity (Active) and inactivity (Inactive).

The development of the locomotive state-detection algorithm and the state-specific pharmaco-EEG analyses were carried out in MATLAB R2017a (The MathWorks, Inc., Natick, Mass., USA) using functions from the sigTOOL toolbox.

As shown in FIG. 1, systemic administration of compound 1e (20 mg/kg, i.v.) shows a clear effect on High Frequency Oscillations (HFO) in the nucleus accumbens compared to vehicle (10% captisol).

Example 4

Microdialysis Studies in Rats

Male Sprague-Dawley rats, initially weighing 275-300 g, were used. The animals were housed under a 12-hr light/dark cycle under controlled conditions for regular in-door temperature (21±2° C.) and humidity (55±5%) with food and tap water available ad libitum.

Rats were anaesthetised with hypnorm/dormicum (2 ml/kg) and intracerebral guide cannulas.

(CMA/12) were stereotaxically implanted into the brain, aiming to position the dialysis probe tip in the ventral hippocampus (co-ordinates: 5.6 mm posterior to bregma, lateral −4.8 mm, 7.0 mm ventral to dura. Anchor screws and acrylic cement were used for fixation of the guide cannulas. The body temperature of the animals was monitored by rectal probe and maintained at 37° C. The rats were allowed to recover from surgery for 2 days, housed singly in cages.

On the day of the experiment a microdialysis probe (CMA/12, 0.5 mm diameter, 3 mm length) was inserted through the guide cannula. The probe was connected via a dual channel swivel to a microinjection pump. Perfusion of the microdialysis probe with filtered Ringer solution (145 mm NaCl, 3 mM KCl, 1 mM MgCl2, 1.2 mM CaCl2) was begun shortly before insertion of the probe into the brain and continued for the duration of the experiment at a constant flow rate of 1 μl/min. After 180 min of stabilisation, the experiments were initiated. Dialysates were collected every 20 min into polystyrene microvials containing trifluoroacetic acid (final concentration 0.25%) at 4° C. After the experiments the animals were sacrificed and the brains removed and the probe placement was verified.

In vitro recovery of the probes was determined by using stock solution of compound 1e at 1000 ng/ml. The experiments were performed at room temperature. For each compound three microdialysis probes (CMA/3) were inserted into tubes containing stock solutions. Perfusion of the microdialysis probe with filtered Ringer solution was begun shortly before insertion of the probe into the stock solutions and continued for the duration of the experiment at a constant flow rate of 1 μl/min. After 60 min of stabilisation 3 consecutive 20-min samples were sampled by each probe.

As shown in FIG. 2, considerable extracellular levels of compound 1e in the rat ventral hippocampus after systemic administration of compound 1e dosed at 30 mg/kg subcutaneously were observed.

The invention claimed is:

1. A compound of Formula I, or a pharmaceutically acceptable salt thereof, wherein:

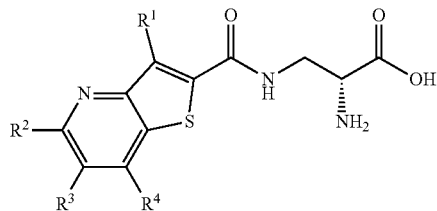

$R^1$ is selected from the group consisting of a hydrogen, halogen, $C_{1-4}$ haloalkyl, cyano, $C_{3-6}$ cycloalkyl, and $C_{1-4}$ alkyl;

$R^2$ is selected from the group consisting of hydrogen, halogen, $C_{1-4}$ haloalkyl, cyano, $C_{3-6}$ cycloalkyl, and $C_{1-4}$ alkyl;

$R^3$ is selected from the group consisting of hydrogen, halogen, $C_{1-4}$ haloalkyl, cyano, $C_{3-6}$ cycloalkyl, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $C_{1-4}$ hydroxyhaloalkyl, cyano, $OR^6$, L-($OR^6$), and $R^7$;

$R^6$ is selected from the group consisting of hydrogen, $C_{1-4}$ alkyl, $C_{1-4}$ haloalkyl, $C_{1-4}$ hydroxyalkyl, and $C_{1-4}$ hydroxyhaloalkyl;

L represents a $C_{1-3}$ alkylene; and $R^7$ is selected from the group consisting of $C_{3-6}$ cycloalkyl, phenyl, 4, 5, or 6 membered heterocycle, and 5 or 6 membered heteroaryl, wherein said cycloalkyl, phenyl, heterocycle or heteroaryl are independently unsubstituted or substituted with 1, 2 or 3 substituents independently selected from halogen, $C_{1-3}$ alkyl, and $C_{1-3}$ alkoxy, wherein said $C_{1-3}$ alkyl and $C_{1-3}$ alkoxy are independently unsubstituted or substituted with 1, 2 or 3 F.

2. The compound according to claim 1, or a pharmaceutically acceptable salt thereof, wherein:

$R^1$ is selected from the group consisting of a hydrogen, halogen, and $C_{1-4}$ alkyl;

$R^2$ is selected from the group consisting of hydrogen, halogen, and $C_{1-4}$ alkyl;

$R^3$ is selected from the group consisting of hydrogen, halogen, and $C_{1-4}$ alkyl;

$R^4$ is selected from the group consisting of hydrogen, halogen, $C_{1-4}$ alkyl, $C_{1-4}$ haloalkyl, $C_{1-4}$ hydroxyalkyl, $OR^6$, and $R^7$;

$R^6$ is selected from the group consisting of $C_{1-4}$ alkyl, and $C_{1-4}$ haloalkyl; and $R^7$ is selected from the group consisting of a $C_{3-6}$ cycloalkyl and phenyl, wherein said cycloalkyl and phenyl is independently unsubstituted or substituted with 1, 2 or 3 substituents independently selected from halogen, $C_{1-3}$ alkyl, $C_{1-3}$ alkoxy, wherein said $C_{1-3}$ alkyl and $C_{1-3}$ alkoxy are independently unsubstituted or substituted with 1, 2 or 3 F.

3. The compound according to claim 1, or a pharmaceutically acceptable salt thereof, wherein $R^1$ is hydrogen.

4. The compound according to claim 1, or a pharmaceutically acceptable salt thereof, wherein $R^2$ is hydrogen.

5. The compound according to claim 1, or a pharmaceutically acceptable salt thereof, wherein $R^3$ is selected from the group consisting of hydrogen, $C_{1-4}$ alkyl, and halogen.

6. The compound according to claim 5, or a pharmaceutically acceptable salt thereof, wherein $R^3$ is selected from the group consisting of hydrogen, fluoro, and methyl.

7. The compound according to claim 6, or a pharmaceutically acceptable salt thereof, wherein $R^3$ is hydrogen.

8. The compound according to claim 1, or a pharmaceutically acceptable salt thereof, wherein $R^1$, $R^2$, and $R^3$ are hydrogen.

9. The compound according to claim 1, or a pharmaceutically acceptable salt thereof, wherein $R^4$ is $C_{1-4}$ alkyl.

10. The compound according to claim 1, or a pharmaceutically acceptable salt thereof, wherein $R^4$ is methyl.

11. The compound according to claim 1, or a pharmaceutically acceptable salt thereof, wherein $R^4$ is $C_{1-4}$ fluoroalkyl.

12. The compound according to claim 1, or a pharmaceutically acceptable salt thereof, wherein $R^4$ is halogen.

13. The compound according to claim 1, or a pharmaceutically acceptable salt thereof, wherein $R^4$ is phenyl unsubstituted or substituted with $C_{1-3}$ alkyl.

14. The compound according to claim 1, or a pharmaceutically acceptable salt thereof, wherein $R^4$ is $C_{1-4}$ alkoxy.

15. The compound according to claim 1, or a pharmaceutically acceptable salt thereof, wherein $R^4$ is selected from the group consisting of $C_{1-4}$ alkyl, $C_{1-4}$ fluoroalkyl, $C_{3-6}$ cycloalkyl, $C_{1-4}$ hydroxyalkyl, $C_{1-4}$ alkoxy, halogen, and phenyl unsubstituted or substituted with ethyl.

16. The compound according to claim 1, or a pharmaceutically acceptable salt thereof, wherein $R^4$ is selected from the group consisting of methyl, ethyl, isopropyl, fluoromethyl, difluoromethyl, trifluoromethyl, hydroxymethyl, isopropoxy, ethoxy, methoxy, cyclopropyl, fluoro, bromo, and ethylphenyl.

17. The compound, or a pharmaceutically acceptable salt thereof, according to claim 1, selected from the group consisting of:
- (R)-2-amino-3-[[7-thieno[3,2-b]pyridine-2-carbonyl]amino]propanoic acid;
- (R)-2-amino-3-[(7-ethylthieno[3,2-b]pyridine-2-carbonyl)amino]propanoic acid;
- (R)-2-amino-3-[[7-(difluoromethyl)thieno[3,2-b]pyridine-2-carbonyl]amino]propanoic acid;
- (R)-2-amino-3-[(7-cyclopropylthieno[3,2-b]pyridine-2-carbonyl)amino]propanoic acid;
- (R)-2-amino-3-[(7-methylthieno[3,2-b]pyridine-2-carbonyl)amino]propanoic acid;
- (R)-2-amino-3-[(7-isopropylthieno[3,2-b]pyridine-2-carbonyl)amino]propanoic acid;
- (R)-2-amino-3-[[7-(2-ethylphenyl)thieno[3,2-b]pyridine-2-carbonyl]amino]propanoic acid;
- (R)-2-amino-3-[(7-methoxythieno[3,2-b]pyridine-2-carbonyl)amino]propanoic acid;
- (R)-2-amino-3-[[7-(trifluoromethyl)thieno[3,2-b]pyridine-2-carbonyl]amino]propanoic acid;
- (R)-2-amino-3-[(7-ethoxythieno[3,2-b]pyridine-2-carbonyl)amino]propanoic acid;
- (R)-2-amino-3-[(7-isopropoxythieno[3,2-b]pyridine-2-carbonyl)amino]propanoic acid;
- (R)-2-amino-3-[(7-bromothieno[3,2-b]pyridine-2-carbonyl)amino]propanoic acid;
- (R)-2-amino-3-[(7-hydroxymethylthieno[3,2-b]pyridine-2-carbonyl)amino]propanoic acid;
- (R)-2-amino-3-[[7-(fluoromethyl)thieno[3,2-b]pyridine-2-carbonyl]amino]propanoic acid;
- (R)-2-amino-3-[(6-fluoro-7-methyl-thieno[3,2-b]pyridine-2-carbonyl)amino]propanoic acid; and
- (R)-2-amino-3-[(6,7-dimethylthieno[3,2-b]pyridine-2-carbonyl)amino]propanoic acid; or a pharmaceutically acceptable salt thereof.

18. The compound, or a pharmaceutically acceptable salt thereof, according to claim 1 wherein the compound is
- (R)-2-amino-3-[(7-methylthieno[3,2-b]pyridine-2-carbonyl)amino]propanoic acid, or a pharmaceutically acceptable salt thereof.

19. A pharmaceutical composition comprising a compound, or a pharmaceutically acceptable salt thereof, according to claim 1, and one or more pharmaceutically acceptable carriers or diluents.

* * * * *